(12) United States Patent
Brossmer et al.

(10) Patent No.: US 9,539,336 B2
(45) Date of Patent: Jan. 10, 2017

(54) SIALIC ACID DERIVATIVES

(71) Applicants: Reinhard Brossmer, Heidelberg (DE); Horst Prescher, Basel (CH)

(72) Inventors: Reinhard Brossmer, Heidelberg (DE); Horst Prescher, Basel (CH)

( * ) Notice: Subject to any disclaimer, the term of this patent is extended or adjusted under 35 U.S.C. 154(b) by 0 days.

(21) Appl. No.: 14/409,704

(22) PCT Filed: Jun. 21, 2013

(86) PCT No.: PCT/EP2013/063020
§ 371 (c)(1),
(2) Date: Dec. 19, 2014

(87) PCT Pub. No.: WO2013/190103
PCT Pub. Date: Dec. 27, 2013

(65) Prior Publication Data
US 2015/0174262 A1    Jun. 25, 2015

(30) Foreign Application Priority Data
Jun. 21, 2012 (EP) ..................... 12172939

(51) Int. Cl.
| | | |
|---|---|---|
| A01N 43/04 | (2006.01) | |
| A61K 31/70 | (2006.01) | |
| A61K 47/48 | (2006.01) | |
| C07H 15/12 | (2006.01) | |
| C07H 15/18 | (2006.01) | |
| A61K 31/167 | (2006.01) | |
| A61K 31/407 | (2006.01) | |
| A61K 31/704 | (2006.01) | |
| C07H 15/26 | (2006.01) | |
| A61K 31/7012 | (2006.01) | |
| A61K 31/7008 | (2006.01) | |

(52) U.S. Cl.
CPC ....... *A61K 47/48092* (2013.01); *A61K 31/167* (2013.01); *A61K 31/407* (2013.01); *A61K 31/704* (2013.01); *C07H 15/12* (2013.01); *C07H 15/18* (2013.01); *C07H 15/26* (2013.01); *A61K 31/7008* (2013.01); *A61K 31/7012* (2013.01)

(58) Field of Classification Search
None
See application file for complete search history.

(56) References Cited

FOREIGN PATENT DOCUMENTS

| WO | 03000709 A2 | 1/2003 |
|---|---|---|
| WO | 2007056525 A2 | 5/2007 |
| WO | 2007056870 A1 | 5/2007 |
| WO | 2012018377 A2 | 2/2012 |
| WO | 2012018380 A2 | 2/2012 |
| WO | 2013/190103 A1 | 12/2013 |

OTHER PUBLICATIONS

Abdu-Allah et al. Bioorganic & Medicinal Chemistry Letters (2009), vol. 19, pp. 5573-5575.*
Abdu-Allah et al., Design and Synthesis of a Multivalent Heterobifunctional CD22 Ligand as a Potential Immunomodulator, Synthesis, vol. 2011, No. 18, Sep. 2011, pp. 2968-2974.
Bräse et al., Organic Azides: An Exploding Diversity of a Unique Class of Compounds, Angewandte Chemie, No. 44, 2005, pp. 5188-5240.
Buskas et al., Use of n-Pentenyl Glycosides as Precursors to Various Spacer Functionalities, J. Org. Chem., vol. 65, No. 4, Jan. 28, 2000, pp. 958-963.
Chen et al., In vivo targeting of B-cell lymphoma with glycan ligands of CD22, Blood, vol. 115, No. 23, Jun. 2010, pp. 4778-4786.
Collins et al., High-affinity ligand probes of CD22 overcome the threshold set by cis ligands to allow for binding, endocytosis, and killing of B cells, J. Immunol., vol. 177, No. 5, Sep. 2006, pp. 2994-3003.
Courtney et al., Sialylated multivalent antigens engage CD22 in trans and inhibit B cell activation, PNAS, vol. 106, No. 8, Feb. 2009, pp. 2500-2505.

(Continued)

*Primary Examiner* — Patrick Lewis
(74) *Attorney, Agent, or Firm* — Kilpatrick Townsend & Stockton LLP

(57) ABSTRACT

A sialic acid derivative of the formula (I),

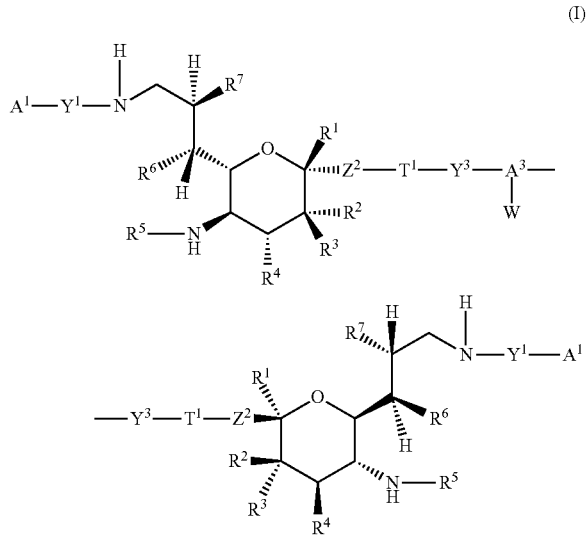

where the symbols are as defined in the description, is suitable for linking with a cargo for regulating metabolic processes, immune reactions, immunizations or desensitizations of the target organism.

15 Claims, No Drawings

(56) References Cited

OTHER PUBLICATIONS

Duong et al., Decoration of T-independent antigen with ligands for CD22 and Siglec-G can suppress immunity and induce B cell tolerance in vivo, J. Exp. Medicine, vol. 207, No. 1, Jan. 2010, pp. 173-187.

El-Faham et al., COMU: A Safer and More Effective Replacement for Benzotriazole-Based Uronium Coupling Reagents, Chem. Eur. J., vol. 15, No. 37, Sep. 21, 2009, pp. 9404-9416.

Fiorina et al., Targeting CD22 reprograms B-cells and reverses autoimmune diabetes, Diabetes, vol. 57, No. 11, Nov. 2008, pp. 3013-3024.

Isidro-Llobet et al., Amino Acid-Protecting Groups, Chemical Reviews, vol. 109, No. 6, Apr. 13, 2009, pp. 2455-2504.

Kaltgrad et al., On-Virus Construction of Polyvalent Glycan Ligands for Cell-Surface Receptors, J. Am. Chem. Soc., vol. 130, No. 14, Mar. 15, 2008, pp. 4578-4579.

Kelm et al., The ligand-binding domain of CD22 is needed for inhibition of the B cell receptor signal, as demonstrated by a novel human CD22-specific inhibitor compound, J. Exp. Med., vol. 195, No. 9, May 2002, pp. 1207-1213.

Lehmann et al., Sialic acid-specific lectins: occurrence, specificity and function, Cell Mol. Life Sci., vol. 63, No. 12, Jun. 2006, pp. 1331-1354.

Magesh et al., High-Affinity Ligands of Siglec Receptors and their Therapeutic Potentials, Current Medicinal Chemistry, vol. 18, No. 23, 2011, pp. 3537-3550.

Mihaylova et al., Simultaneous engagement of FcgammaIIb and CD22 inhibitory receptors silences targeted B cells and suppresses autoimmune disease activity, Mol. Immunol., vol. 47, No. 1, Nov. 2009, pp. 123-130.

Montalbetti et al., Amide bond formation and peptide coupling, Tetrahedron, vol. 61, No. 46, Nov. 2005, pp. 10827-10852.

O'Donnell et al., Development and characterization of CD22-targeted pegylated-liposomal doxorubicin (IL-PLD), Investigational New Drugs, vol. 28, No. 3, Jun. 2010, pp. 260-267.

O'Reilly et al., Bifunctional CD22 ligands use multimeric immunoglobulins as protein scaffolds in assembly of immune complexes on B cells, J. Am. Chem. Soc., vol. 130, No. 24, Jun. 2008, pp. 7736-7745.

O'Reilly et al., CD22 is a recycling receptor that can shuttle cargo between the cell surface and endosomal compartments of B cells, J. Immunol., vol. 186, No. 3, Feb. 2011, pp. 1554-1563.

O'Reilly et al., Siglecs as targets for therapy in immune-cell-mediated disease, Trends Pharmacol. Sci., vol. 30, No. 5, May 2009, pp. 240-248.

Rhee et al., Colorful Virus-like Particles: Fluorescent Protein Packaging by the Qβ Capsid, Biomacromolecules, vol. 12, No. 11, Oct. 13, 2011, pp. 3977-3981.

Roy et al., N-Acetylneuraminic Acid: Neoglycoproteins and Pseudopolysaccharides, J. Carbohydrate Chemistry, vol. 6, No. 1, 1987, pp. 161-165.

Schauer, Sialic acids: fascinating sugars in higher animals and man, Zoology, vol. 107, No. 1, Mar. 2004, pp. 49-64.

Scriven et al., Azides: their preparation and synthetic uses, Chemical Reviews, vol. 88, No. 2, Mar. 1988, pp. 297-368.

Steirer et al., The asialoglycoprotein receptor regulates levels of plasma glycoproteins terminating with sialic acid alpha2,6-galactose, J. Biol. Chem., vol. 284, No. 6, Feb. 2009, pp. 3777-3783.

Tedder et al., CD22: a multifunctional receptor that regulates B lymphocyte survival and signal transduction, Adv. Immunol., vol. 88, 2005, pp. 1-50.

Varki, Sialic acids in human health and disease, Trends in Mol. Med., vol. 48, No. 8, Jul. 2008, pp. 351-360.

International Application No. PCT/EP2013/063020, International Search Report mailed on Jul. 24, 2013, 7 pages (4 pages for the original document and 3 pages for the English translation).

International Application No. PCT/EP2013/063020, Written Opinion of the International Searching Authority mailed on Dec. 21, 2014, 8 pages.

* cited by examiner

SIALIC ACID DERIVATIVES

PRIORITY CLAIM

This application is a national stage application of PCT/EP2013/063020, filed Jun. 21, 2013, which claims priority to European Patent Application No. 12 172 939.6, filed on Jun. 21, 2012, the entireties of which are incorporated herein by reference.

The invention relates to derivatives of sialic acid, to methods for the preparation thereof and to use thereof for preparing conjugates.

Sialic acid is the generic term for a family of 9-carbon atom sugars, which are all derivatives of neuraminic acid (Neu) and ketodesoxynonulosonic acid (KDN). Typically, these are located on the exposed non-reducing ends of oligosaccharide chains. Sialic acids play numerous roles in mammals and in the human organism (Schauer (2004) Zoology, 107, 49-64; Varki (2008) Trends in Mol Med, 14, 8, 351-360). Furthermore, they are used by many pathogens, for example, to achieve an efficient infection or to evade the host immune system (Glycoconjugate J. 2006, vol. 23, issue 1-2, all articles). Many of these functions are regulated by proteins that recognize sialic acids (Lehmann et al (2006) Cell-Mol. Life Sci. 63, 1331-1354).

A subset of such proteins are the Siglecs. They are lectins of the Ig type, which are characterized by an N-terminal V-set domain, which enables specific recognition of sialic acids. An overview of the types of Siglec proteins known to date and of diseases potentially treatable with Siglec inhibitors can be found in Trends in "Pharmacological Sciences 2009, 30 (5), 240-248" and "Current Medicinal Chemistry 2011, 18, 3537-3550" and the references contained therein.

CD22 (Siglec-2) is highly expressed on B cells. It is known that B cell-based diseases, particularly lymphomas and autoimmune diseases can be treated with CD22 ligands (Tedder et al (2005) Advances in Immunology 88, 1-50; Fiorina et al (2008) Diabetes 57, 3013-3024).

It is also known that conjugates for the treatment of CD22 and B cell-mediated diseases may be prepared by linking a CD22 ligand with a pharmacologically active molecule. Sialic acid-containing Siglec trisaccharide ligands have already been developed, for example, for preparing cargo-bearing polymers (Collins et al (2006) Journal of Immunology 177, 2994-3003 and WO 2007056525). It is also known that monovalent sialic acid-containing Siglec trisaccharide ligands and anti-Siglec antibodies are suitable for preparing Siglec-specific transport vehicles, particularly liposomes and virus capsids (O'Donnell et al. (2010) Invest. New Drugs 28, 260-267; Chen et al. (2010) Blood 115, 23 4778-4786; Kaltgrad et al. (2008) J. Am. Chem Soc. 130, 4578-4579; Rhee (2011) Biomacromolecules 12, 3977-3981; WO 2012018377). Furthermore, sialic acid-containing trisaccharide Siglec ligands for linking with a cargo have been developed for preparing non-covalently linked oligomers (O'Reilly (2011) J. Immunol. 186, 1554-1563). Furthermore, a cargo has been linked to sialic acid-containing Siglec trisaccharide ligands, which triggers an immune reaction on the cell surface to the cargo and the Siglec-bearing cell (O'Reilly (2008) J. Am. Chem Soc. 130, 7736-7745; WO 2007056870).

Furthermore, polymeric CD22 ligands have been linked with an antigen, in order to achieve tolerance to the antigen (Mihaylova et al. (2009), Mol. Immunol. 47, 1, 123-130; Courtney et al. (2009) PNAS 106, 8, 2500-2505; Duong et al. (2010) J. Exp. Medicine 207, 1, 173-187). Liposomes have also been occupied simultaneously with CD22 ligands or anti-CD22 antibodies and antigens in order to induce tolerance to the antigen (WO 2012018380).

The derivatives of sialic acid described all comprise galactose, which renders them as potential ligands for the asialoglycoprotein receptor and for galectins (Steirer et al. (2009) J. Biol. Chem. 284, 6, 3777-3783).

Although the known derivatives are suitable for linking with a cargo and the conjugates produced have the desired properties, there is still considerable room for improvement, particularly relating to affinity and selectivity. Furthermore, there is room for improvement with respect to the required number of ligands per cargo in order to obtain a conjugate with desired properties. There is also room for improvement with respect to the potential linking possibilities with a cargo. Furthermore, there is room for improvement with respect to pharmacological compatibility and administration forms and also the stability in plasma and liver.

The object of the invention is to provide compounds with which advantages in the areas mentioned, at least in some areas, are achieved.

It has been found that certain dimeric sialic acid derivatives have an increased affinity for CD22 and at the same time are suitable for linking with a cargo.

The invention therefore relates to a sialic acid derivative of the formula (I),

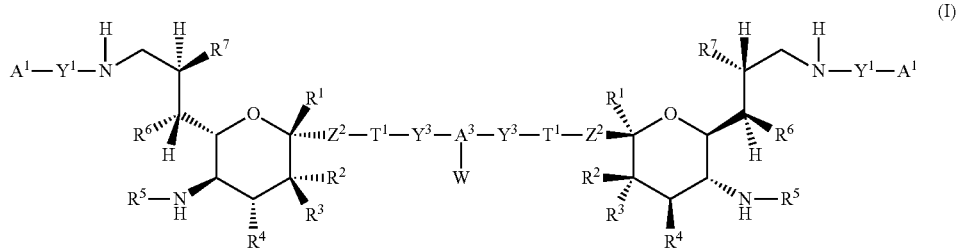

(I)

where the symbols are defined as follows:

$A^1$ is equal to 4-biphenyl, 4-(2-thienyl)benzoyl, 4-(3-thienyl)benzoyl, 1-naphthyl and 2-naphthyl, in which the residues mentioned are unsubstituted or mono- or poly-substituted by a group $X^1$;

$X^1$ is identically or differently fluorine, chlorine, hydroxyl, carboxy, $SO_3M$, $OSO_3M$, $SO_2NH_2$, $SO_2CF_3$, alkyl, cycloalkyl, haloalkyl, alkyloxy, haloalkyloxy, alkylcarbonyloxy, alkylcyclocarbonyloxy, aminocarbonyl, alkylaminocarbonyl, cycloalkylaminocarbonyl, alkylcarbonylamino, cycloalkylcarbonylamino, alkylamino, cycloalkylamino, dialkylamino, dicycloalkylamino or alkylcycloalkylamino, in which the alkyl groups in these residues comprise 1 to 4, and the cycloalkyl groups 3 or 4, carbon atoms;

$Y^1$ is equal to ~($C_1$-$C_2$-alkyl)-, ~C(O)— or ~$CH_2$C(O)—, in which ~ denotes the bond to the group $A^1$;

$Z^2$ is equal to —O—, —S— or —$CH_2$—;

$T^1$ is equal to a straight-chain or branched alkanediyl group having 3 to 10 C atoms, in which
  (i) optionally one or more non-terminal $CH_2$ groups are replaced by —O— and/or —S— and/or
  (ii) optionally one or more H atoms are replaced by F and/or Cl and/or
  (iii) optionally one non-terminal —$CH_2CH_2$— group is replaced by —NHCO—;

$Y^3$ is equal to —C(O)—, ~C(O)—NH— or ~NH—C(O)—, in which ~ denotes the bond to group $A^3$;

$A^3$ is
  a) a $C_1$-$C_8$-alkanetriyl, in which optionally more than one non-terminal $CH_2$ groups are replaced by O, S, S(O), $S(O)_2$, $NR^x$ and/or C(O) and wherein optionally one or more H atoms in the groups mentioned are replaced by a group $X^2$,
  b) is a saturated, partially unsaturated or aromatic, mono- or polycyclic hydrocarbon residue having 3 to 14 C atoms or one three- to eight-membered, aromatic, partially unsaturated or saturated mono- or polycyclic heterocyclic residue, in which the groups mentioned are optionally substituted in each case by one or more groups $X^2$,
  c) a tertiary nitrogen;

$X^2$ is equal to fluorine, chlorine, alkyl, haloalkyl or alkyloxy, in which the alkyl groups in these residues comprise 1 to 2 carbon atoms;

W is —$Y^5$-$T^2$-V or —V;

V is ~C(O)O-4-nitrophenyl, ~C(O)O-pentafluorophenyl, maleic-2-yl anhydride, ~C(O)—1-azetidin-2-one, ~4-O-phenyl-C(O)— 1-azetidin-2-one, ~N═C═O, ~N═S═O, ~C(O)$N_2$, ~$S(O)_2$Cl, ~C($NH_2$)$OR^y$, ~P($CH_2OH)_3$, ~SH, ~SC(O)$CH_3$, ~$NH_2$, ~OH, ~CH═$CH_2$, ~C≡CH, ~COOM, ~C(O)H, ~C(O)$CH_3$, ~C(O)C(O)H, ~I, ~$N_3$, ethyl-2-(3-indol)amine-1~, ~$S(O)_2$ $N_3$, phenyl-CH═CH—C($N_2$)—C(O)O~, ~CH═$CHCH_2$OC(O)$R^y$, ~CH═CHCH$OC(O)NHR^y$, ~OC(O)$OR^y$, ~C(O)$NHNH_2$, ~N-maleimide, aziridine-2~, pyridine-2-S—S~, phenyl-1-carboxy-2-nitro-5-S—S~, ~$S(O)_2$CH═$CH_2$, ~C(O)—S-phenyl, ~C(O)CH═$N_2$, ~C(O)O—N-succinimidyl, or C(O)O—N-sulphosuccinimidyl;

$Y^5$ is a bond, —O—, —S—, —$NR^x$—, —C(O)—, ~C(O)—$NR^x$— or ~$NR^x$—C(O)—, in which ~ denotes the bond to group $A^3$;

$T^2$ is a straight-chain or branched alkanediyl group having 1 to 200 C atoms, in which
  (i) optionally one or more non-terminal $CH_2$ groups are replaced by —O—, NH and/or —S— and/or
  (ii) optionally one or more non-terminal H atoms are replaced by F, Cl, (═O), $NR^z$ and/or $NR^y$ and/or
  (iii) optionally one or more non-terminal —$CH_2CH_2$— group is replaced by —NHCO— or —S—S—;

$R^1$ is equal to C(O)OM;

$R^2$, $R^3$ are equal to H;

$R^4$, $R^6$, $R^7$ are identically or differently OH or $OR^z$;

$R^5$ is equal to C(O)$CH_3$ or C(O)$CH_2$OH;

M is equal to a $C_1$-$C_4$-alkyl, $C_3$-$C_4$-cycloalkyl or a cation;

$R^x$ is identically or differently H, $R^y$ or $R^z$;

$R^y$ is identically or differently $C_1$-$C_4$-alkyl, $C_3$-$C_4$-cycloalkyl, phenyl or benzyl and $R^z$ is identically or differently —C(O)—$C_1$-$C_4$-alkyl, —C(O)—$C_3$-$C_4$-cycloalkyl, —C(O)— phenyl or C(O)—$CH_2$-phenyl.

The invention also relates to the use of a sialic acid derivative of the formula (I) in a method for linking with a cargo. For example, low molecular weight active ingredients (low molecular weight pharmacologically active substances), radioactively labeled substances, cytostatics, RNA, DNA, proteins, or another therapeutically applicable cargo are linked. Preference is given to a low molecular weight pharmacologically active substance, a cytostatic, a protein, an antigenic protein, an enzyme, an antigen, a low molecular weight antigen, a DNA, an RNA, an oligonucleotide, a radioactive substance, an organometallic complex or a peptide. For example, the conjugates can be used in a method for modulating the immune system, for example in vaccinations or transplants and for the treatment of diseases, especially allergies, autoimmune diseases, chronic inflammation, paraplegia, multiple sclerosis, viral diseases such as AIDS, bacterial diseases, parasitic diseases, diseases in which the immune response is impaired in the context of B-cell activation such as common variable immunodeficiency (CVID) and IgA deficiency, in diseases of the blood-forming organs and of the blood as well as in cancer, for example, lymphomas and myelomas.

The invention further relates also to the use of a sialic acid derivative of the formula (I) in a method for linking with a cargo, preferably a cargo selected from the group consisting of RNA, DNA, peptides, low molecular weight antigens, antigenic proteins, enzymes and low molecular weight pharmacologically active substances, particularly for regulating metabolic processes, immune reactions, immunizations or desensitizations of the target organism.

The invention further relates to the use of a pharmacologically active conjugate of a sialic acid derivative of the formula (I) according to the invention and of a cargo, preferably selected from the group consisting of RNA, DNA, peptides, cytostatics, enzymes, organometallic complexes and low molecular weight pharmacologically active substances, in a method for the treatment of infections, tumours or allergies.

The invention further relates also to the use of a sialic acid derivative of the formula (I) in a method for linking with a cargo, preferably selected from the group consisting of RNA, DNA, peptides, enzymes, organometallic complexes and low molecular weight pharmacologically active substances, for the treatment of allergies and immune reactions.

The invention further relates also to the use of a pharmacologically active conjugate of a sialic acid derivative of the formula (I) and of a cargo, preferably selected from the group consisting of RNA, DNA, peptides, enzymes, organometallic complexes and low molecular weight pharmacologically active substances, in a method for the treatment of allergies and immune reactions.

The invention likewise also relates to the use of a sialic acid derivative of the formula (I) in a method for linking with liposomes, nanoparticles, organometallic complexes, metal nanoparticles such as gold nanoparticles, micromicelles, carbon nanotubules and other transport vehicles. The vehicle may include pharmacologically active substances, proteins, antigens or vaccines and vaccine adjuvants.

The invention likewise also relates to the use of a sialic acid derivative of the formula (I) in a method for preparing liposomes, nanoparticles, micromicelles, carbon nanotubules and other transport vehicles.

The invention likewise also relates to the use of a sialic acid derivative of the formula (I) in a method for linking with molecules for diagnostic purposes. For example, a sialic acid derivative of formula (I) may be linked with a fluorescent molecule, a positron emitter, or another diagnostically usable cargo.

The invention likewise also relates to the use of a sialic acid derivative of the formula (I) in a method for preparing polyvalent ligands. By linking with a polyvalent carrier molecule, active substances can be prepared having improved properties. These substances can be used for use in a method for modulating the immune system, for example in vaccinations and also for the treatment of diseases whose course or activity can be positively influenced by the Siglec inhibitors, especially allergies, autoimmune diseases, chronic inflammation, paraplegia, multiple sclerosis, cancer, viral diseases such as AIDS, bacterial diseases, for example streptococci, parasitic diseases such as Chagas disease, diseases in which the immune response is impaired in the context of B cell activation such as common variable immunodeficiency (CVID) and IgA deficiency, in diseases of the blood-forming organs and of the blood as well as in cancer, such as lymphomas and myelomas.

Furthermore, the invention relates to the use of a sialic acid derivative of the formula (I) according to the invention for linking with a cargo-bearing polymer, wherein the cargo is preferably selected from the group consisting of RNA, DNA, cytostatics, peptides, low molecular weight antigens, antigenic proteins, enzymes, organometallic complexes and low molecular weight pharmacologically active substances.

In the context of the invention, "cargo" refers to a low molecular weight pharmacologically active substance, a cytostatic, a protein, an antigenic protein, an enzyme, an antigen, a low molecular weight antigen, a DNA, an RNA, an oligonucleotide, a radioactive substance, an organometallic complex or a peptide, preferably a low molecular weight pharmacologically active substance, a protein, an antigen, an oligonucleotide, a radioactive substance or a peptide, wherein said cargo is bound to the group W of the compound of the formula (I).

The sialic acid derivatives of the formula (I) have surprisingly high affinity for CD22. Apart from sialic acid, they contain no other carbohydrates. They contain a reactive group that is easy to vary, thus enabling conjugation with numerous cargo molecules. Other novel reactive groups can also be introduced for linking to a cargo via the reactive group. They optionally include a cleavable group. In contrast to antibodies, a chemical preparation without the use of cell cultures is possible. The sialic acid derivatives of the formula (I) may be linked by cleavable or non-cleavable linkers depending on the cargo. The ligands may be linked to the cargo such that the activity of the cargo is not affected, or is re-prepared only in the target cell. Conjugates of sialic acid derivatives of the formula (I) can be prepared uniformly and definably in terms of their structure.

The term "sialic acid derivative of formula (I)" includes all stereoisomeric forms of the compound of the formula (I), in particular the E/Z or cis/trans isomers of substituted double bonds or rings, and also stereoisomers resulting from the chiral centres of the compounds of the formula (I), in particular enantiomers and diastereoisomers, in pure form or in the form of mixtures of any composition, in which the individual chiral centres are present in each case in the (S) or (R) form.

The individual stereoisomers can be prepared, for example, by the enrichment of the isomeric mixture by customary methods, such as chromatography or crystallization, or by using isomerically pure starting materials. The enrichment of the isomers may take place at the level of the reactants, intermediates or end products of the formula (I). Isomers included in accordance with the invention also include all tautomeric forms of compounds of the formula (I) and all mesomorphic forms.

In general, the salts of those cations or the acid addition salts of those acids, whose cations or anions do not impair use in the preparation of conjugates with the compounds (I), are suitable.

Suitable cations are in particular ions of the alkali metals, preferably lithium, sodium and potassium, the alkaline earth metals, preferably calcium and magnesium, and the transition metals, preferably manganese, copper, zinc and iron, and also ammonium, where, if desired, one to four hydrogen atoms can be replaced by $R^Y$ in this case, preferably ammonium, dimethylammonium, diisopropylammonium, tetramethylammonium, triethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulphonium ions, preferably tri($C_1$-$C_4$-alkyl)sulphonium and sulphoxonium ions, preferably tri($C_1$-$C_4$-alkyl)sulphoxonium. Preferred are Na, Li, K, Ca, Mg and ammonium (optionally substituted), particularly preferred are Na, Li and K, while Na is especially preferable.

Anions of acid addition salts are, for example, chloride, bromide, fluoride, hydrogen sulphate, sulphate, dihydrogen phosphate, hydrogen phosphate, nitrate, hydrogen carbonate, carbonate, hexafluorosilicate, hexafluorophosphate, benzoate, the anions of $C_1$-$C_4$-alkanoic acids, preferably formate, acetate, propionate and butyrate, and other organic acids such as pivalic acid, maleic acid, succinic acid, pimelic acid, fumaric acid, malic acid, sulphamic acid, phenylpropionic acid, gluconic acid, ascorbic acid, nicotinic acid, citric acid and adipic acid.

Furthermore, the term "sialic acid derivative of the formula (I)" comprises solvates, for example hydrates or adducts with alcohols, and also all crystal modifications.

Unless otherwise stated, symbols which are used more than once, may independently have the same or different meanings.

Definitions of the symbols stated in the formula (I) signify:

Halogen: fluorine, chlorine;

Alkyl: saturated, straight-chain or branched hydrocarbon residues having, for example, 1 to 4 carbon atoms, such as methyl, ethyl, propyl, 1-methylethyl, butyl, 1-methylpropyl, 2-methylpropyl or 1,1-dimethylethyl;

Cycloalkyl: saturated cyclic hydrocarbons having 3 or 4 carbon atoms, such as cyclopropyl, cyclobutyl and 1-methylcyclopropyl;

Haloalkyl: an alkyl group, preferably methyl group, where, in this group, hydrogen atoms are partially or completely replaced by halogen atoms: such as chloromethyl, fluoromethyl or trifluoromethyl;

Alkyloxy: alkyloxy groups with saturated alkyl residue, where this is from the aforementioned group of alkyls and contains 1 to 2 carbon atoms;

Haloalkyloxy: haloalkyloxy groups with haloalkyl residue, where this is from the aforementioned group of haloalkyls;

Alkylcarbonyloxy: alkylcarbonyloxy groups with saturated, straight-chain, branched or cyclic alkyl residue, where this is from the aforementioned group of alkyls and contains 1 to 4 carbon atoms;

Alkylaminocarbonyl: alkylaminocarbonyl groups with saturated, straight-chain, branched or cyclic alkyl residue, where this is from the aforementioned group of alkyls and contains 1 to 4 carbon atoms;

Alkylamino: alkylamino groups with saturated, straight-chain, branched or cyclic alkyl residue, where this is from the aforementioned group of alkyls and contains 1 to 4 carbon atoms;

Dialkylamino: dialkylamino groups with saturated, straight-chain, branched or cyclic alkyl residues, where this is from the aforementioned group of alkyls and contains 1 to 4 carbon atoms;

Alkylcarbonylamino: alkylcarbonylamino groups with saturated, straight-chain, branched or cyclic alkyl residue, where this is from the aforementioned group of alkyls and contains 1 to 4 carbon atoms;

Alkanetriyl denotes for residue $A^3$: saturated, straight-chain alkanetriyl group having, for example, 1 to 6 carbon atoms, such as methane-1,1,1-triyl, ethane-1,1,2-triyl, propane-1,2,3-triyl, propane-1,1,3-triyl, butane-1,2,4-triyl, butane-1,1,4-triyl, pentane-1,1,5-triyl, pentane-1,2,5-triyl, pentane-1,3,5-triyl, hexane-1,1,6-triyl, hexane-1,2,6-triyl or hexane-1,3,6-triyl;

Alkanediyl signifies for residue $T^1$: saturated, straight-chain or branched alkanediyl group having, for example, 3 to 10 carbon atoms, such as propane-1,3-diyl, butane-1,4-diyl, pentane-1,5-diyl, hexane-1,6-diyl, heptane-1,7-diyl, octane-1,8-diyl, nonane-1,9-diyl or decane-1,10-diyl;

Alkanediyl signifies for residue $T^2$: saturated, straight-chain alkanediyl group having, for example, 1 to 200 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl;

Mono- or polycyclic, aromatic, partially unsaturated or saturated $C_3$-$C_{14}$-hydrocarbon residue denotes for $A^3$, for example:
a) identically or differently $C_6$-$C_{14}$-aryltriyl, particularly phenylene-1,2,4-triyl, phenylene-1,3,5-triyl and naphthalene-1,2,4-triyl;
b) $C_3$-$C_8$-cycloalkyltriyl, for example cyclopropane-1,2,3-triyl, cyclohexane-1,2,4-triyl and cyclohexane-1,3,5-triyl;

Three- to eight-membered saturated, partially unsaturated or aromatic heterocyclic residue denotes for $A^3$, for example:
a) 5-membered heteroaryltriyl, comprising one to four nitrogen atoms or one to three nitrogen atoms and/or one sulphur or oxygen atom, particularly thiophene-2,3,5-triyl and 1H(1,2,3)triazole-1,4,5-triyl;

The symbols in the formula (I) are advantageously defined as follows:
$A^1$ is advantageously equal to a group 4-biphenyl, 1-naphthyl and 2-naphthyl, in which the groups mentioned are unsubstituted or are substituted by one or more groups $X^1$.
$X^1$ is advantageously identically or differently fluorine, chlorine, hydroxyl, alkyl, haloalkyl, alkyloxy, haloalkyloxy, alkylcarbonyloxy, in which the alkyl groups in these residues comprise 1 to 2 carbon atoms.
$Y^1$ is advantageously equal to —C(O)— or ~CH$_2$C(O)—, in which ~ denotes the bond to group $A^1$.
$Z^2$ is advantageously equal to —O—.
$T^1$ is advantageously equal to a straight-chain or branched alkanediyl group having 4 to 8 C atoms, in which
  (i) optionally one or more non-terminal CH$_2$ groups are replaced by —O— and/or —S— and/or
  (ii) optionally one non-terminal —CH$_2$CH$_2$— group is replaced by —NHCO—.

$Y^3$ is advantageously equal to a bond, ~C(O)—NH— or ~NH—C(O)—, in which ~ denotes the bond to group $A^3$.
$A^3$ is advantageously a
  a) $C_1$-$C_5$-alkanetriyl, in which optionally one or more non-terminal CH$_2$ groups are replaced by O, S, NR$^x$ and/or C(O) and wherein optionally one or more H atoms in the groups mentioned are replaced by a group $X^2$,
  b) phenylene-1,2,4-triyl or 1H(1,2,3)triazole-1,4,5-triyl, in which the groups mentioned are in each case optionally substituted by one or more groups $X^2$,
  c) tertiary nitrogen.
$X^2$ is advantageously equal to fluorine, chlorine, methyl, methyloxy.
W is advantageously —$Y^5$-$T^2$-V or —V.
V is advantageously ~C(O)O-4-nitrophenyl, ~C(O)O-pentafluorophenyl, maleic-2-yl anhydride, ~N═C═O, ~N═S═O, ~C(O)N$_2$, ~P(CH$_2$OH)$_3$, ~SH, ~NH$_2$, ~OH, ~CH═CH$_2$, ~C≡CH, ~COOM, ~C(O)H, ~C(O)CH$_3$, ~C(O)C(O)H, ~I, ~N$_3$, ~C(O)NHNH$_2$, ~N-maleimide, aziridine-2~, pyridine-2-S—S~, phenyl-1-carboxy-2-nitro-5-S—S~, —C(O)O—N-succinimidyl.
$Y^5$ is advantageously a bond, —O—, —NH—, —C(O)—, ~C(O)—NH— or ~NH—C(O)—, in which ~ denotes the bond to group $A^3$.
$T^2$ is advantageously a straight-chain or branched alkanediyl group having 1 to 200 C atoms, in which
  (i) optionally one or more non-terminal CH$_2$ groups are replaced by —O— or —NH— and/or
  (ii) optionally one or more non-terminal H atoms are replaced by F or (═O) and/or
  (iii) optionally one or more non-terminal —CH$_2$CH$_2$— group is replaced by —NHCO— or —S—S—.
$R^1$ is advantageously equal to C(O)OM.
$R^2$, $R^3$ are advantageously equal to H.
$R^4$, $R^6$, $R^7$ are advantageously identically or differently OH or OR$^z$.
$R^5$ is advantageously equal to C(O)CH$_3$.
M is advantageously equal to a $C_1$-$C_2$-alkyl or a cation.
$R^x$ is advantageously identically or differently H, R$^y$ or R$^z$.
$R^y$ is advantageously identically or differently $C_1$-$C_3$-alkyl, cyclopropyl, phenyl or benzyl.
$R^z$ is advantageously identically or differently —C(O)—$C_1$-$C_4$-alkyl, —C(O)-phenyl or —C(O)—CH$_2$-phenyl.

Definitions of the symbols stated in the formula (I) advantageously signify:
Halogen: fluorine, chlorine;
Alkyl: saturated, straight-chain or branched hydrocarbon residues having, for example, 1 to 3 carbon atoms, such as methyl, ethyl, propyl and 1-methylethyl;
Cycloalkyl: cyclopropyl;
Haloalkyl: chloromethyl, fluoromethyl and trifluoromethyl;
Alkyloxy: alkyloxy groups with saturated alkyl residue, where this is from the aforementioned group of alkyls and contains 1 to 2 carbon atoms;
Haloalkyloxy: haloalkyloxy groups with haloalkyl residue, where this is from the aforementioned group of haloalkyls;
Alkylcarbonyloxy: alkylcarbonyloxy groups with saturated, straight-chain or branched alkyl residue, where this is from the aforementioned group of alkyls and contains 1 to 3 carbon atoms;
Alkanetriyl denotes for residue $A^3$: saturated, straight-chain alkanetriyl group having, for example, 1 to 5 carbon atoms, such as methane-1,1,1-triyl, ethane-1,1,2-triyl, propane-1,2,3-triyl, propane-1,1,3-triyl, butane-1,2,4-triyl, butane-1,1,4-triyl, pentane-1,1,5-triyl, pentane-1,2,5-triyl or pentane-1,3,5-triyl;

Alkanediyl signifies for residue $T^1$: saturated, straight-chain or branched alkanediyl group having, for example, 4 to 8 carbon atoms, such as butane-1,4-diyl, pentane-1,5-diyl, hexane-1,6-diyl, heptane-1,7-diyl or octane-1,8-diyl;

Alkanediyl signifies for residue $T^2$: saturated, straight-chain alkanediyl group having, for example, 1 to 200 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl;

Compounds of the formula (I), in which all symbols, definitions and indices have the advantageous definitions, are advantageous.

The symbols in the formula (I) are preferably defined as follows:

$A^1$ is preferably equal to 4-biphenyl, in which the group mentioned is unsubstituted or is substituted by one or more hydroxyl groups.

$Y^1$ is preferably equal to —C(O)—, in which ~ denotes the bond to group $A^1$.

$Z^2$ is preferably equal to —O—.

$T^1$ is preferably equal to hexane-1,6-diyl, in which optionally one non-terminal $CH_2$ group is replaced by —S—.

$Y^3$ is preferably equal to ~C(O)—NH—, in which ~ denotes the bond to group $A^3$.

$A^3$ is preferably propane-1,1,3-triyl or phenyl-1,2,4-triyl.

W is preferably —$Y^5$-$T^2$-V or —V.

V is advantageously ~SH, ~$NH_2$, ~CH=$CH_2$, ~C≡CH, ~COOM, ~I, ~$N_3$, ~C(O)$NHNH_2$, ~N-maleimide, ~C(O)O—N-succinimidyl.

$Y^5$ is preferably a bond, —O— or ~NHCO—, in which ~ denotes the bond to group $A^3$.

$T^2$ is preferably a straight-chain or branched alkanediyl group having 1 to 200 C atoms, in which
 (i) optionally one or more non-terminal $CH_2$ groups are replaced by —O— and/or
 (ii) optionally one or more non-terminal —$CH_2CH_2$— groups are replaced by —NHCO— or —S—S—.

$R^1$ is preferably equal to C(O)OM.

$R^2$, $R^3$ are preferably equal to H.

$R^4$, $R^6$, $R^7$ are preferably equal to OH or OC(O)$CH_3$.

$R^5$ is preferably equal to C(O)$CH_3$.

M is preferably $CH_3$ or sodium.

Definitions of the symbols stated in the formula (I) preferably signify:

Alkanediyl preferably signifies for residue $T^2$: saturated, straight-chain alkanediyl group having, for example, 1 to 200 carbon atoms, such as methane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl.

Preferred compounds of the formula (I) are those in which all symbols, definitions and indices have the preferred definitions.

Furthermore, preferred sialic acid derivatives of the formula (I) are those of the formulae (Ia)-(Ib), in which the symbols have the definitions and preferences stated in the formula (I).

Particularly preferred are, furthermore, sialic acid derivatives of the formulae (Iaa)-(Iba), in which the symbols are defined as stated in the formula (I):

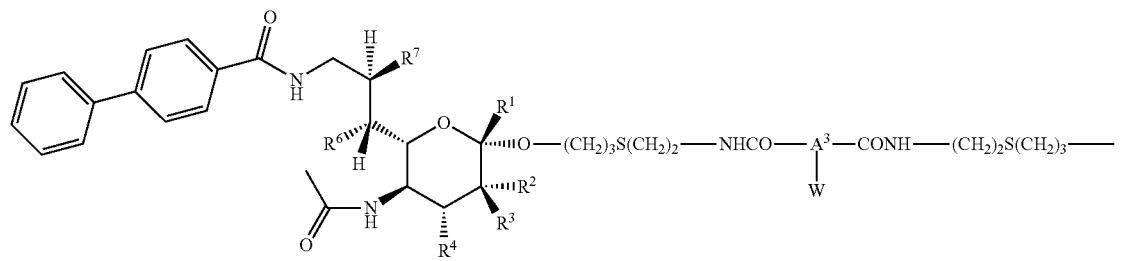
Iaa
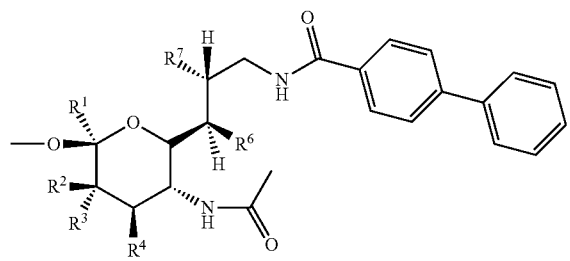
Iab
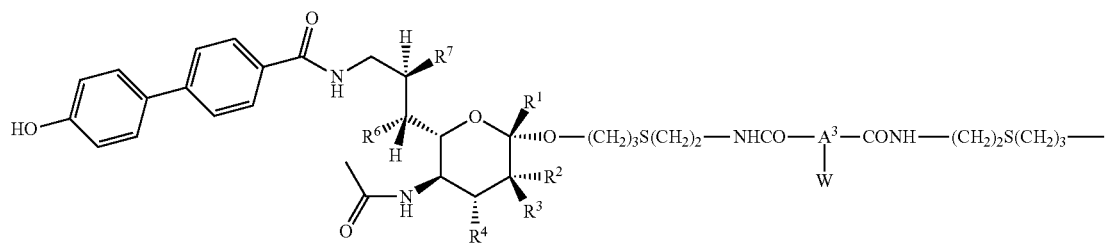
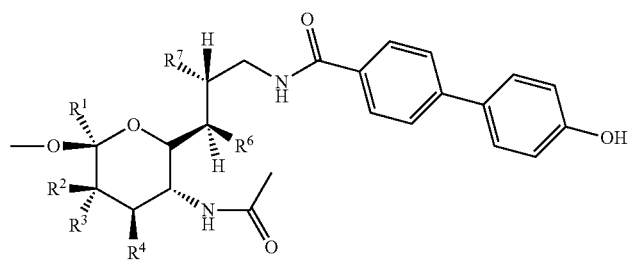
Also particularly preferred are sialic acid derivatives of the formulae (Iac)-(Iaf), in which the symbols are defined as stated in the formula (I):
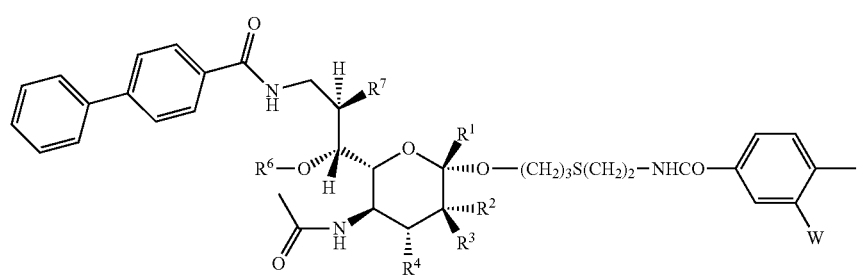
Iac -continued
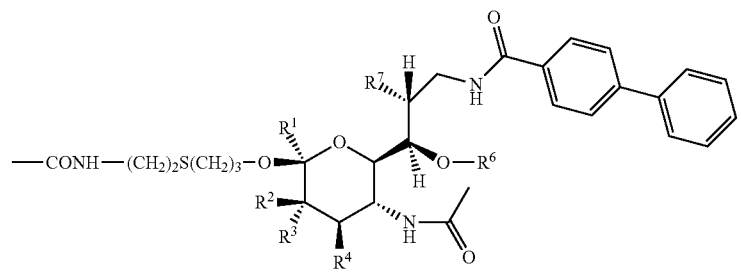
Iad
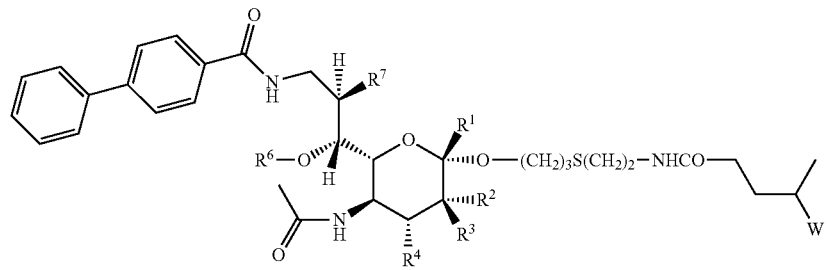
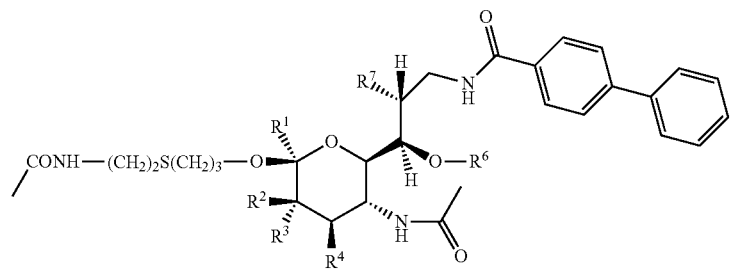
Iae
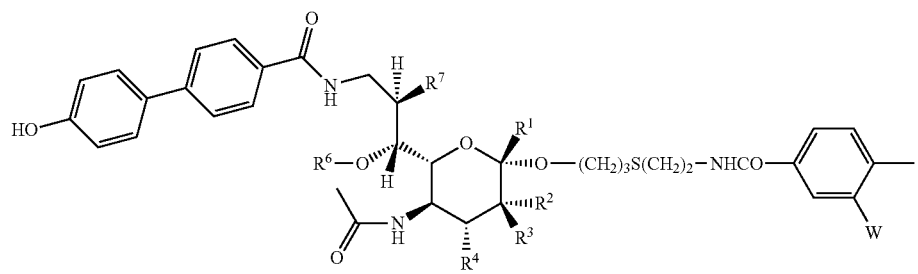
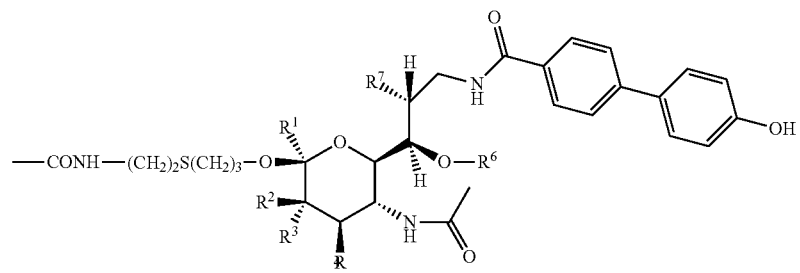
Iaf
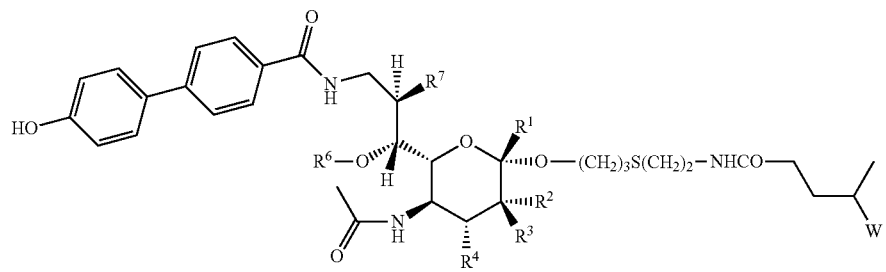

-continued

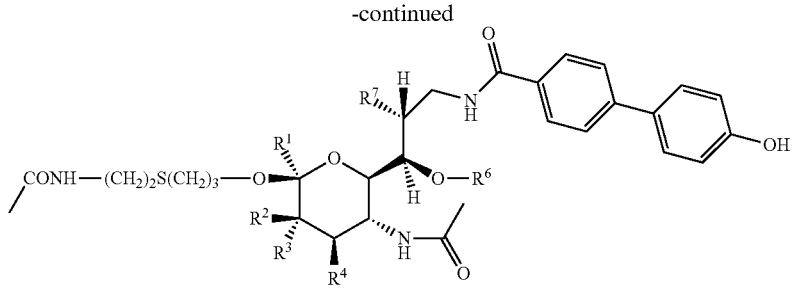

The sialic acid derivatives (I) according to the invention are obtainable in principle using known synthetic methods. The compounds are preferably obtained by the preparation methods according to the invention illustrated in detail below, particularly the synthetic Schemes I-IX:

Scheme I

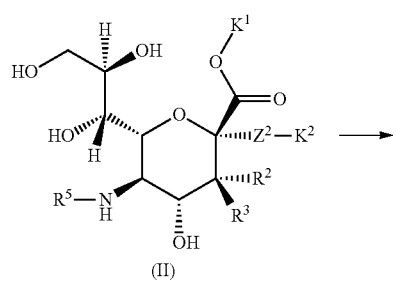

(II)

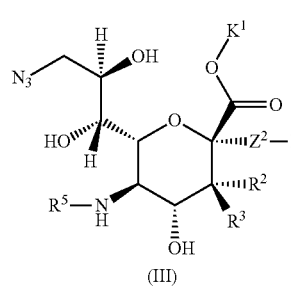

(III)

$K^1$ is alkyl, particularly $C_1$-$C_3$-alkyl $K^2$ is alkenyl, protected aminoalkyl $Z^2$ is equal to O, S or $CH_2$ Compounds of the formula (III) can be prepared from the compounds of the formula (II) by introduction of an azido group (Scheme I). The introduction of azido groups is described, for example, in Angewandte Chemie 2005, 117, 5320-5374 and Chem Rev 1988, 88 (2), 297-368. Exemplary compound 6 was prepared.

Scheme II

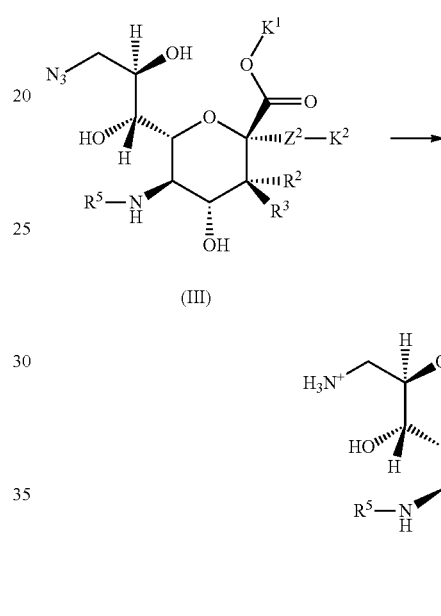

(III)

(IV)

$K^1$ is alkyl, particularly $C_1$-$C_3$-alkyl $K^2$ is e.g.: alkenyl, protected aminoalkyl $Z^2$ is equal to O, S or $CH_2$ Compounds of the formula (IV) can be prepared by reducing the azido group in the compounds of the formula (III) (Scheme II). The reduction of azido groups is described, for example, in Angewandte Chemie 2005, 117, 5320-5374 and Chem Rev 1988, 88 (2), 297-368.

Exemplary compound 7 was prepared.

Scheme III

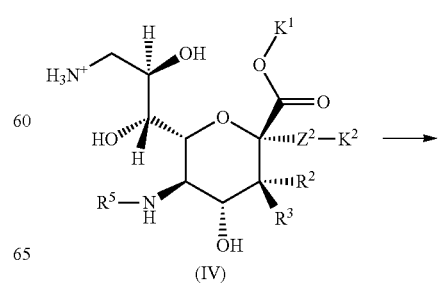

(IV)

-continued

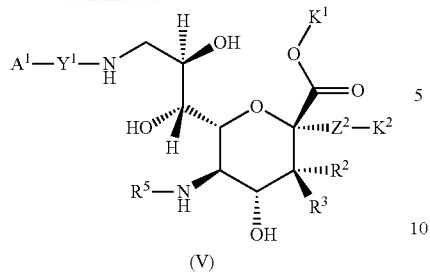

(V)

$K^1$ is an alkyl, particularly $C_1$-$C_3$-alkyl
$K^2$ is e.g.: alkenyl, protected aminoalkyl
$Z^2$ is equal to O, S or $CH_2$ Compounds of the formula (V) can be prepared from the amine in compounds of the formula (IV) by formation of an amide bond (Scheme III). Reactions of amines to amides are described, for example, in Tetrahedron 2005, 61, 10827-10852.

Exemplary compounds 8 and 30 were prepared.

Scheme IV

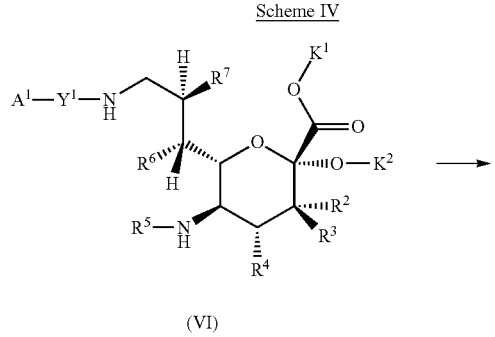

(VI)

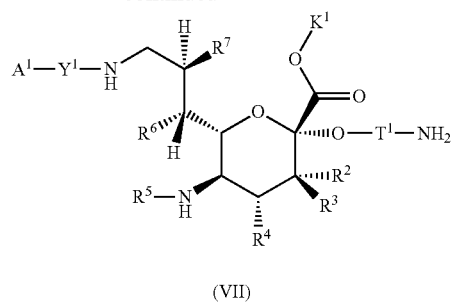

(VII)

$K^1$ is alkyl, particularly $C_1$-$C_3$-alkyl $K^2$ is an alkenyl, protected aminoalkyl Compounds of the formula (VII) can be prepared by reacting a terminal double bond of the compounds of the formula (VI) with a reactive group (Scheme IV). Reactions of double bond are described, for example, in J. Org. Chem. 2000, 65, 958-963. Compounds of the formula (VII) can also be prepared by deprotecting the amino group in compounds of the formula (IV) (Scheme VI). Protecting groups and reactions for deprotecting amino groups are described, for example, in "Protecting Groups" Philip J. Kocienski, 3rd Edition, Thieme 2005 and Chem. Rev. 2009, 109, 2455-2504.

Exemplary compounds 9 and 31 were prepared.

The preparation of dimeric starting products is described, for example, in Scheme V.

Scheme V

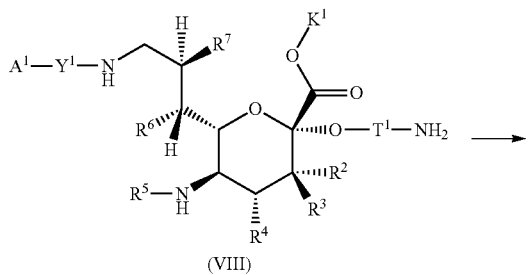

(VIII)

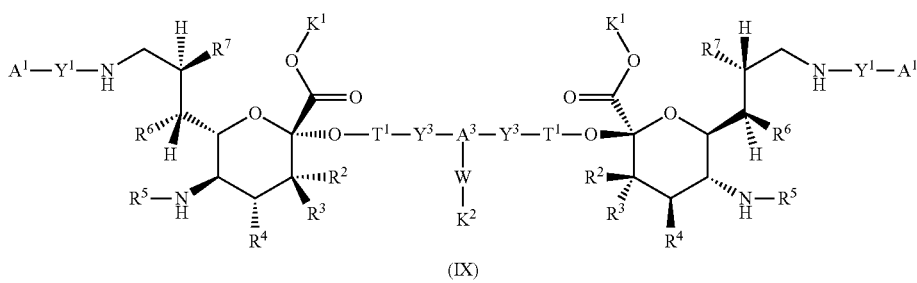

(IX)

$K^1$ is alkyl, particularly methyl
$K^2$ is equal to a protecting group for W

Compounds of the formula (IX) can be prepared by reacting the amino group in compounds of the formula (VIII) with divalent, reactive compounds (Scheme V). Reactions of amines with reactive compounds are described in Tetrahedron 2005, 61, 10827-10852 and Chem. Eur. J. 2009, 15, 9404-9416. The reaction may also be carried out using coupling reagents or by in situ activations of a divalent compound. Coupling reagents and their reactions are described in Tetrahedron 2005, 61, 10827-10852 and Chem. Eur. J. 2009, 15, 9404-9416.

Exemplary compounds 10, 14, 17, 20 and 21 were prepared.

The preparation of sialic acid derivatives of the formula (I) is described, for example, in Schemes VI to VIII.

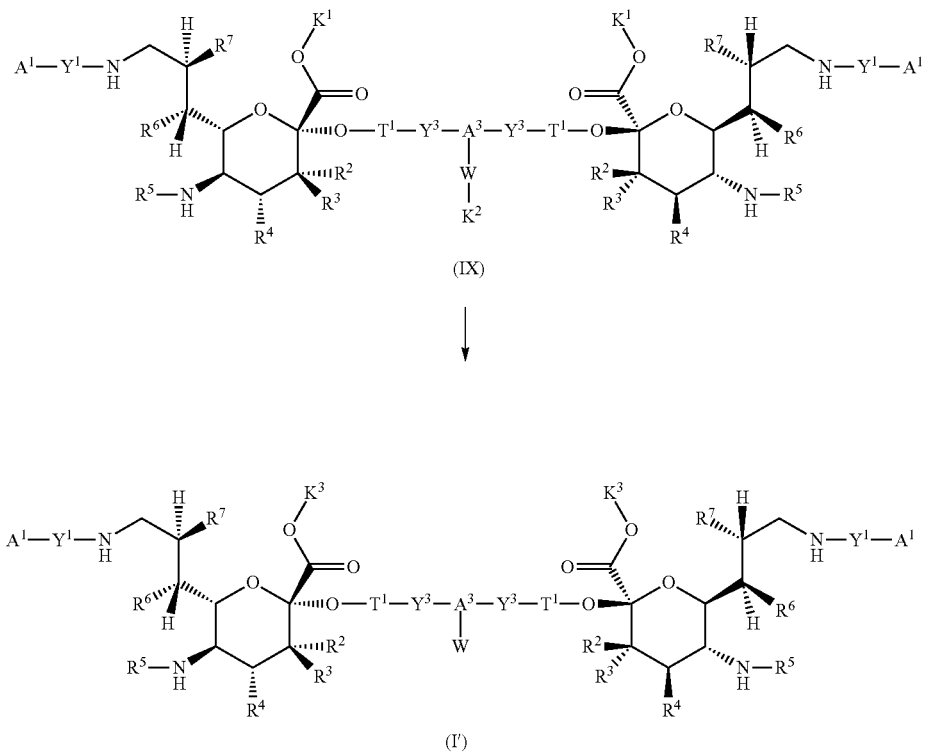

Scheme VI $K^1$ is alkyl, particularly methyl
$K^2$ is a protecting group for W
$K^3$ is $K^1$ or M Compounds of the formula (I') can be prepared by deprotecting the groups W in compounds of the formula (IX) (Scheme VI). Protecting groups and reactions for deprotecting are described, for example, in "Protecting Groups" Philip J Kocienski, 3rd Edition, Thieme 2005 and Chem. Rev. 2009, 109, 2455-2504.

Exemplary compounds 15, 11, 28 and 29 were prepared.

Scheme VII

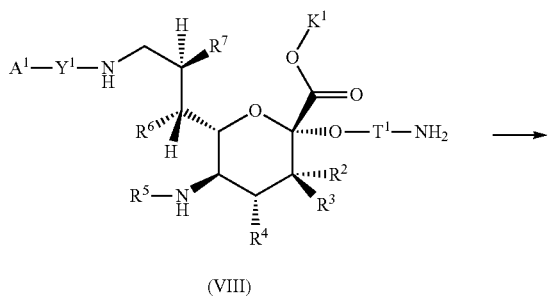

(VIII)

-continued

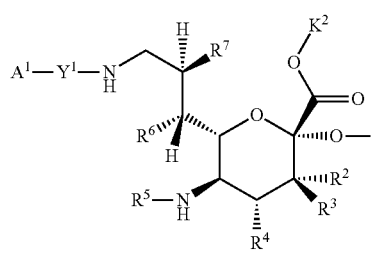
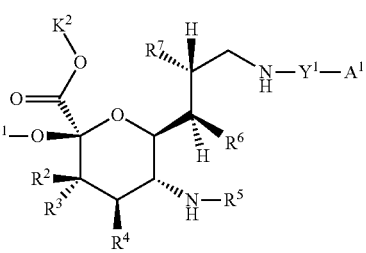

(I″)

$K^1$ is alkyl, particularly methyl
$K^2$ is $K^1$ or M

Compounds of the formula (I″) can be prepared by reacting the amino group in compounds of the formula (VIII) with divalent, reactive compounds (Scheme VII). Reactions of amines with reactive compounds are described, for example, in Tetrahedron 2005, 61, 10827-10852 and Chem. Eur. J. 2009, 15, 9404-9416. The reaction may also be carried out using coupling reagents or by in situ activations of a divalent compound. Coupling reagents and their reactions are described in Tetrahedron 2005, 61, 10827-10852 and Chem. Eur. J. 2009, 15, 9404-9416.

Exemplary compounds 13, 18, and 32 were prepared.

$K^1$ is alkyl or M
$V^1$ is a reactive group, particularly an amine
$V^2$ is another reactive group Compounds of the formula (I‴) can be prepared by reacting the group $V^1$ in compounds of the formula (I″) with a substance comprising a group $V^2$ (Scheme VIII). The group $V^1$ forms a part of $T^2$ following the reaction. The group $V^2$ may also be formed during the reaction or be furnished with a protecting group which can be subsequently deprotected. Protecting groups and reactions for deprotecting are described, for example, in "Protecting Groups" Philip J Kocienski, 3rd Edition, Thieme 2005 and Chem. Rev. 2009, 109, 2455-2504.

Scheme VIII

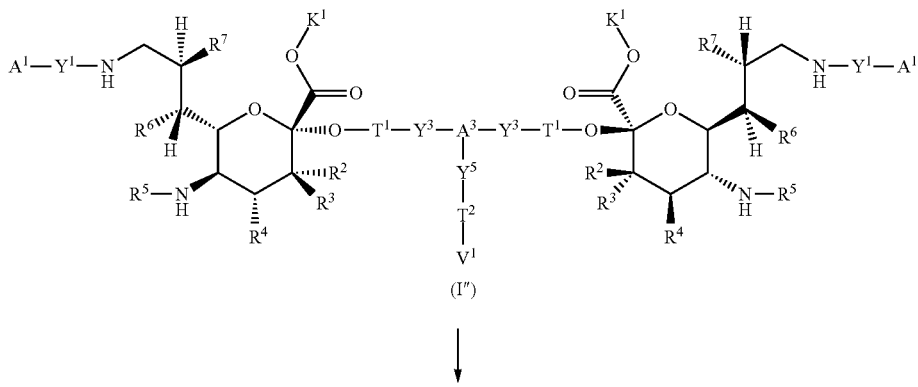

(I″)

↓

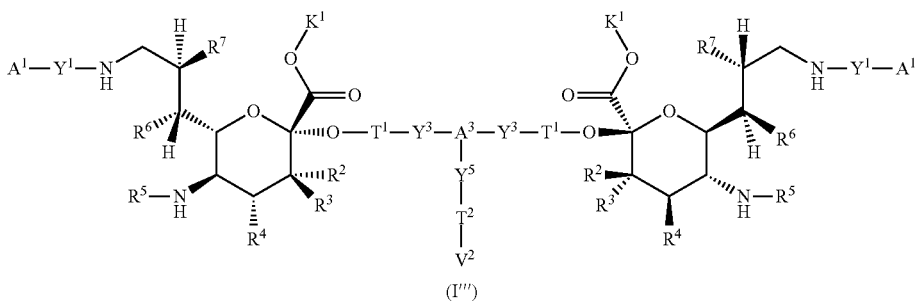

(I‴)

Exemplary compounds 23, 24, 26, 27, 28 and 41 were prepared.

The preparation of conjugates with sialic acid derivatives of the formula (I) is described, for example, in Scheme IX.

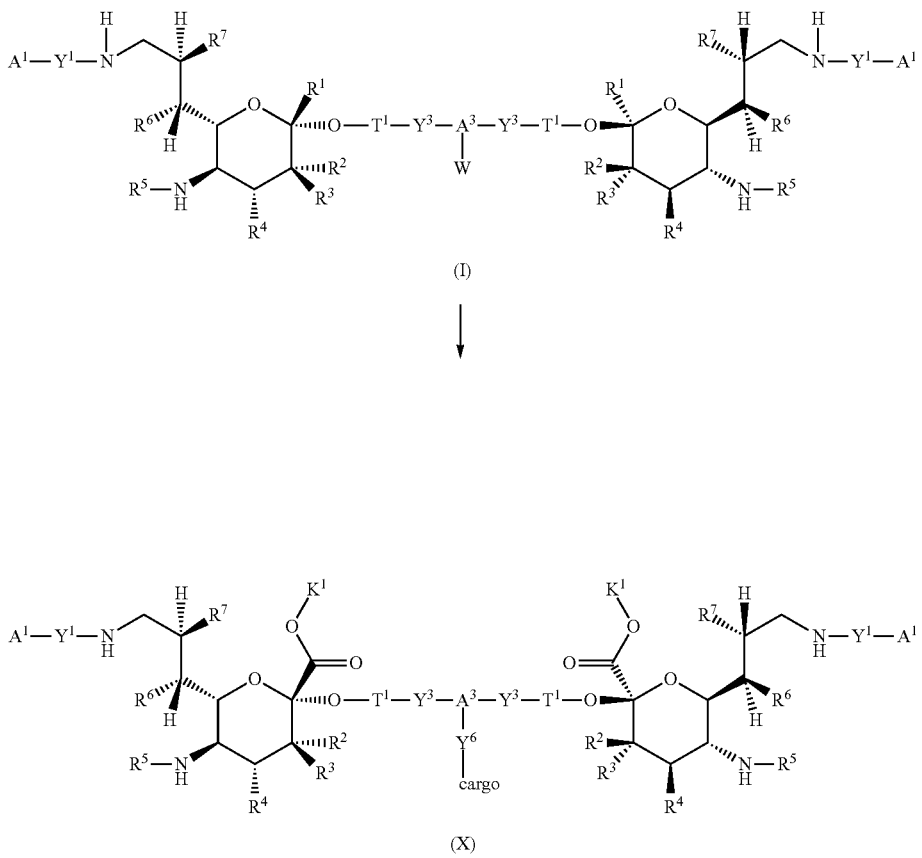

Scheme IX $Y^6$ is the linker formed by the linking

Compounds of the formula (X) can be prepared by reacting the group W in compounds of the formula (I) with a cargo (Scheme IX). Here, the cargo can react one or more times with a compound of the formula (I).

Exemplary compounds 35, 36, 37, 38, 39 and 40 were prepared.

The sialic acid derivatives of the formula (I) are suitable for the preparation of pharmacologically active compounds and active ingredients for medicament formulations.

Pharmacologically active compounds and active ingredients prepared from sialic acid derivatives of the formula (I) are effective for the treatment of diseases whose course or activity are affected by Siglec-bearing cells, in particular allergies, autoimmune diseases, chronic inflammation, paraplegia, multiple sclerosis, cancer, viral diseases such as AIDS, and also in bacterial diseases, for example streptococci, parasitic diseases, diseases in which the immune response is impaired in the context of B cell activation such as common variable immunodeficiency (CVID) and IgA deficiency.

Preferred indications are allergies, cancer, autoimmune diseases and vaccinations.

In the context of the invention, treatment signifies a therapeutic treatment, both for curing and for alleviating symptoms, and also a preventative treatment.

Pharmacologically active compounds and active ingredients prepared from sialic acid derivatives of the formula (I) may be used in combination with other pharmacologically active substances, particularly those which enhance the efficacy of the pharmacologically active compounds and active ingredients prepared from the sialic acid derivatives of the formula (I).

The invention also relates to a method for the treatment of a B cell-mediated disease, particularly from the group of allergies, autoimmune diseases, chronic inflammation, paraplegia, multiple sclerosis, cancer, viral diseases such as AIDS, diseases in which the immune response is impaired in the context of B cell activation such as common variable immunodeficiency (CVID) and IgA deficiency, in which a person affected by the disorder is administered a preferably therapeutically effective amount of a pharmacologically active compound prepared from one of the sialic acid derivatives of the formula (I).

The sialic acid derivatives of the formula (I) may also be used for preparing a conjugate for purposes other than those mentioned, for example, as diagnostics, in methods for determining the activity of Siglec ligands, as biochemical probes or as intermediates for preparing further, particularly pharmacologically active, compounds.

The invention is illustrated in detail by the examples without being restricted thereto.

EXAMPLES
A. Synthesis examples are presented in Schemes 1 to 6.
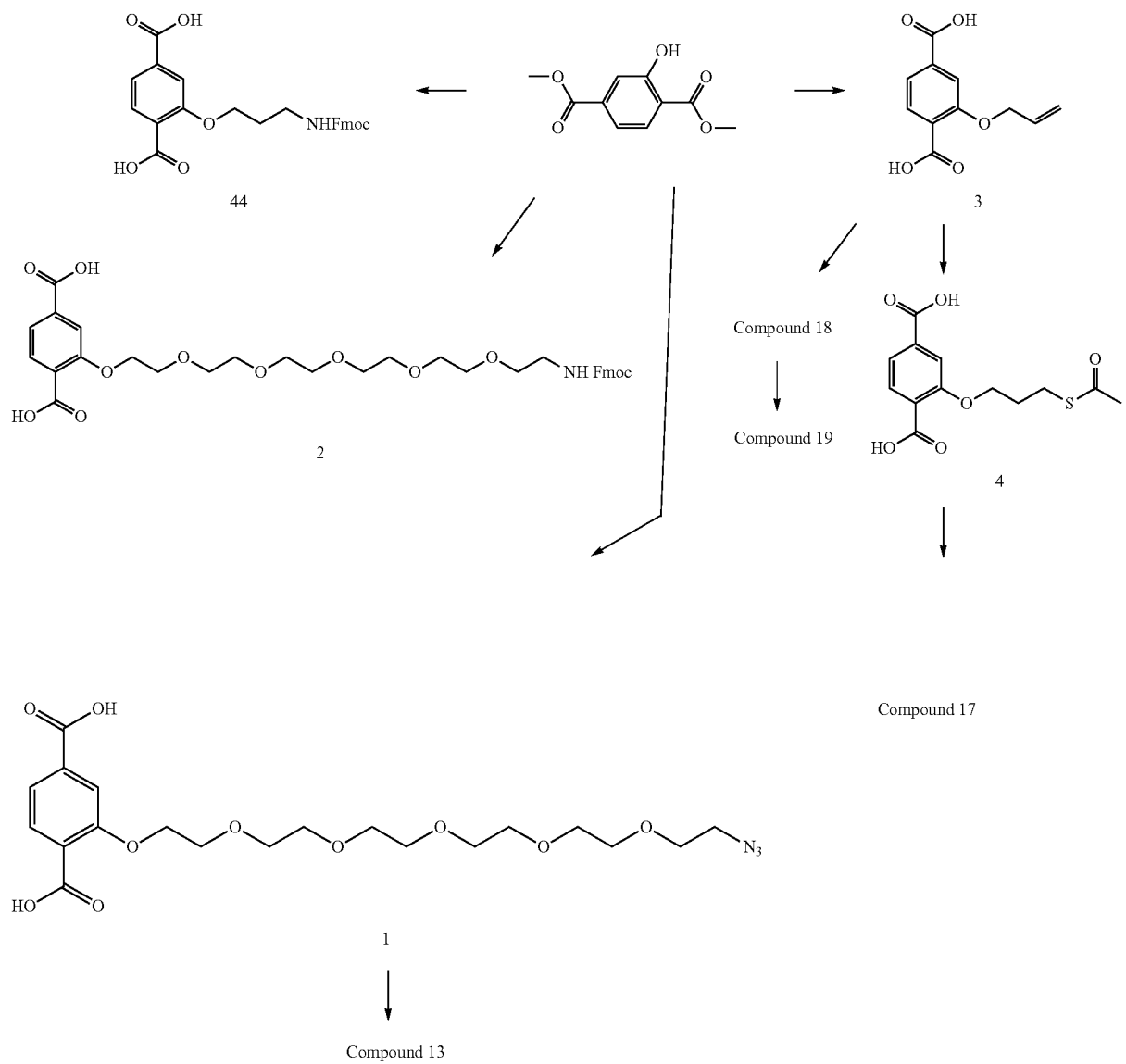
Scheme 1
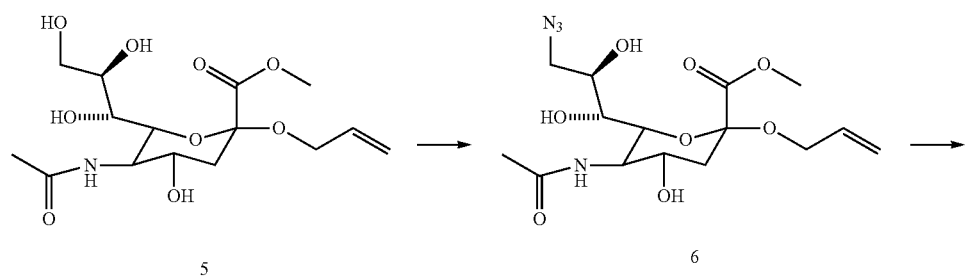
Scheme 2

-continued
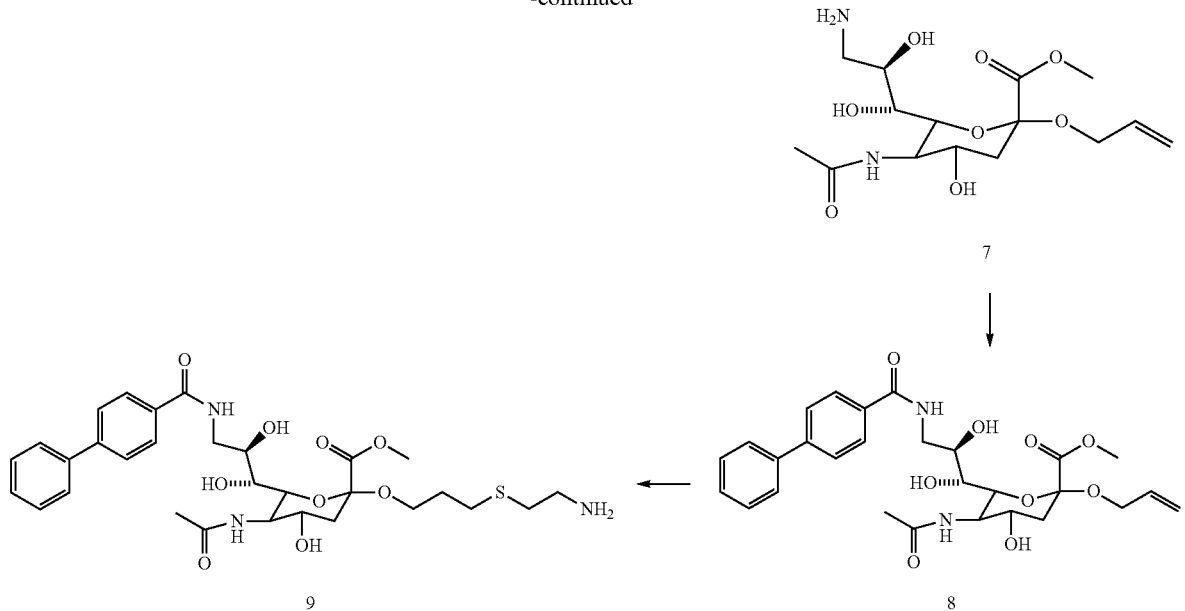

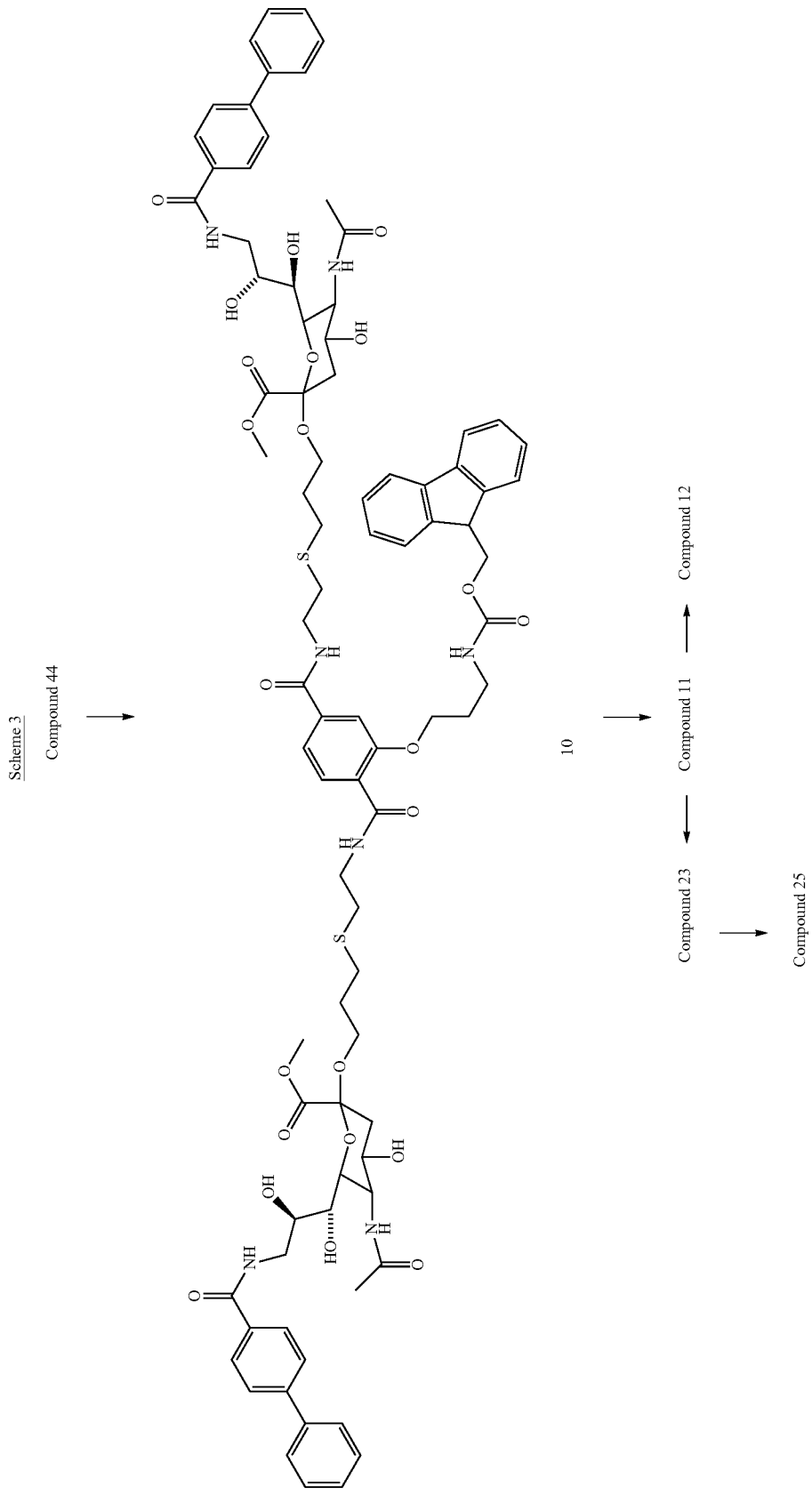

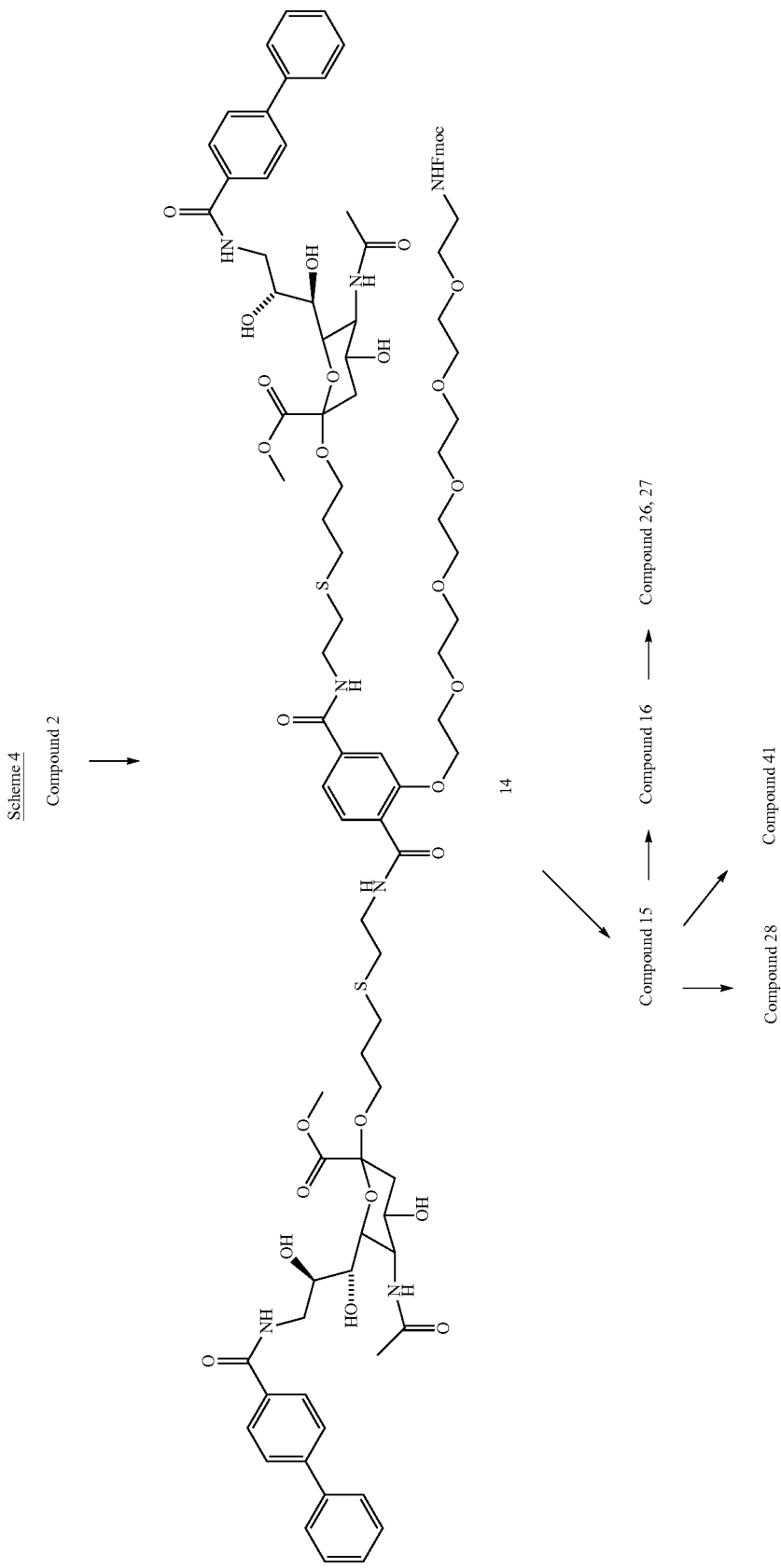

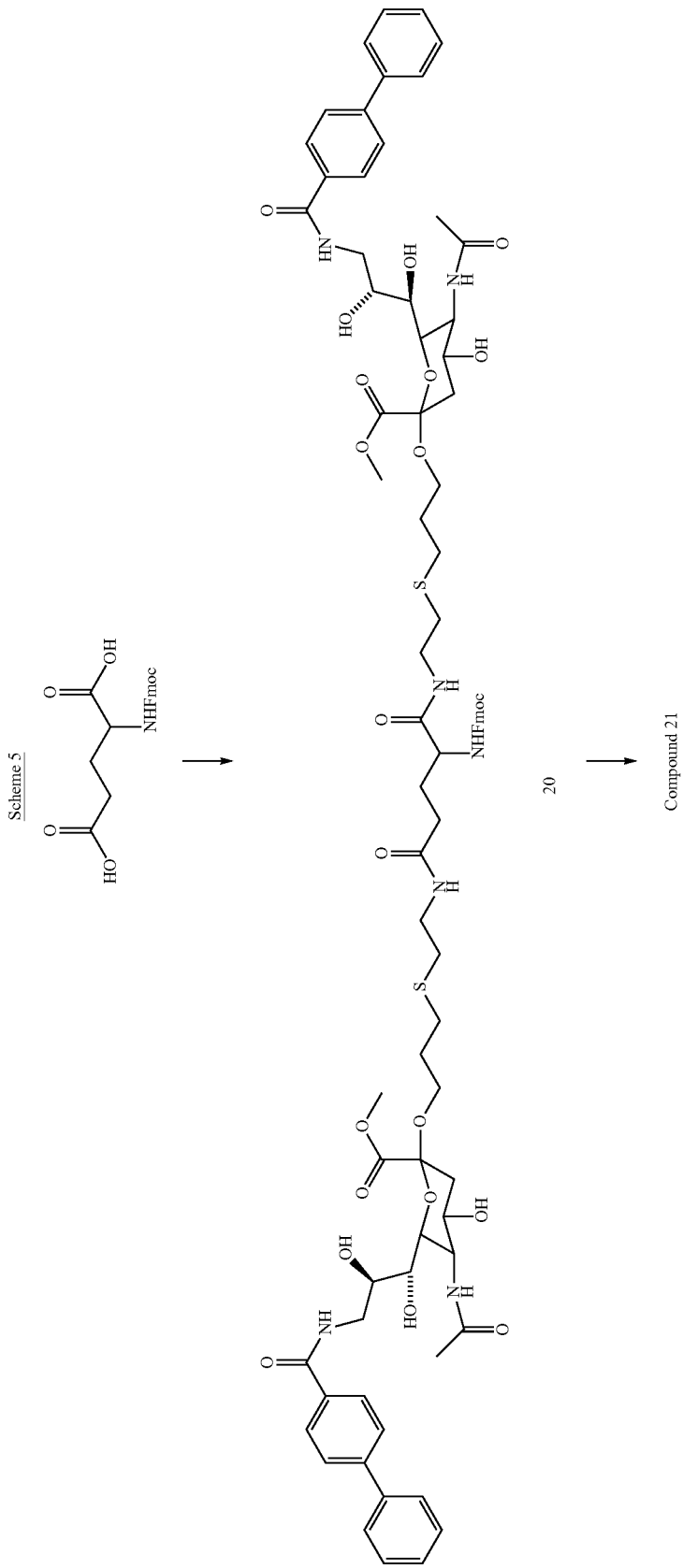

Scheme 6

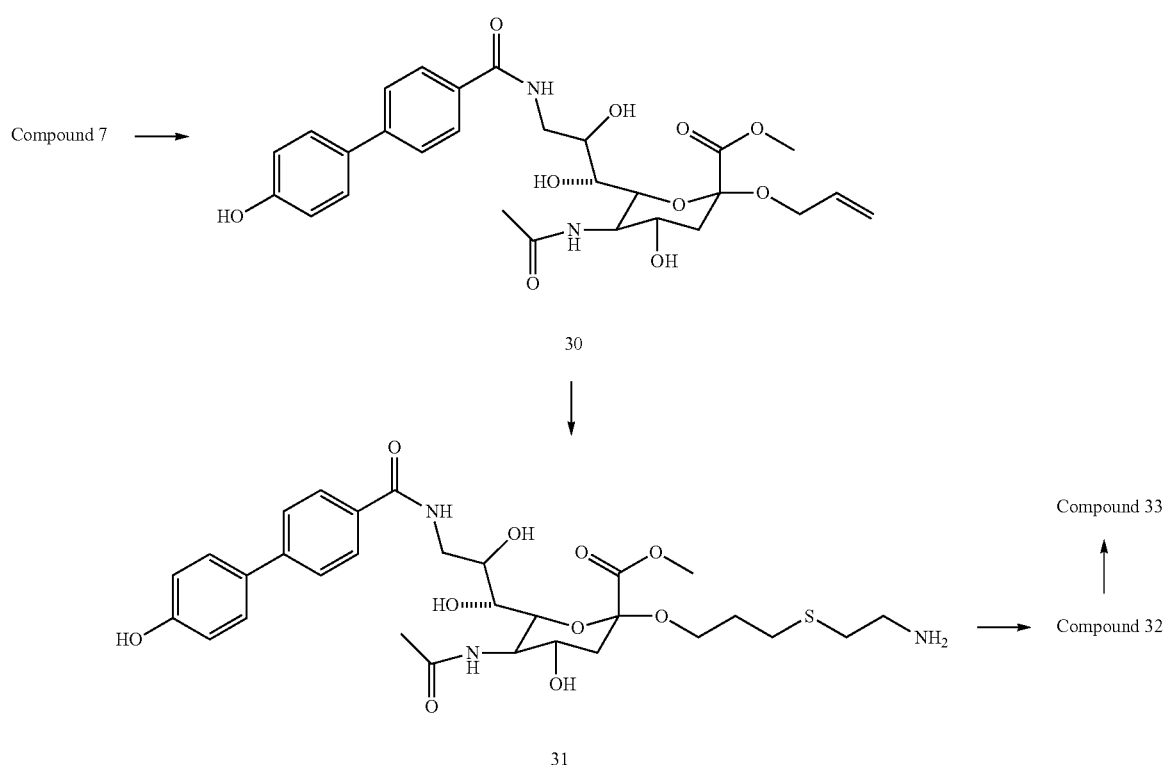

The compounds were obtained as described below:

All compounds used but not described were purchased or prepared by known literature methods.

For purifications with silica gel, silica gel Si60 43-60 μm was used. Approximately 100 g of silica gel were used per gramme of substance.

For purifications on RP-18 silica gel (YMC CO LTD., YMC ODS-AQ), the latter was suspended in ethanol, filled into a column, prewashed with water and the substance applied as a solution or suspension with water. The column volume was approximately 5 cm in height and approximately 1 cm in diameter. The solvent was pushed through the column under low pressure, generated by a hand-operated pressure bulb. Eluents are indicated in paranthesis. Gradients are expressed with the symbol >>, e.g.: "(H2O>>EtOH)" signifies that a gradient of water to ethanol was used.

Solvents were removed fully by means of a vacuum rotary evaporator under reduced pressure and at a bath temperature of 40° C. In the following syntheses, this operation is identified as "removal of the solvent" or "concentration".

Lyophilization was performed from water or a water-dioxane mixture unless otherwise stated.

Photochemical reactions were carried out using the Photochemical Reactor Model #RPR-100 from The Southern New England Ultraviolet Company.

The reactions and substances were monitored by thin-layer chromatography. For this purpose, silica gel-coated aluminium plates with fluorescence indicator were used (Merck TLC Silica gel 60 $F_{254}$). Substances were detected under UV light at 366 and 254 nm. The chromatograms were subsequently sprayed with dilute sulphuric acid and heated in order to detect the carbohydrates. For detection purposes, amines were sprayed with ninhydrin solution and heated and thiols with nitroprusside solution. Details and other detection methods are elucidated in "Anfärbereagenzien für Dünnschicht- and Papierchromatographie" [Colour reagents for thin-layer and paper chromatography] Merck, 1970.

All substances were checked by mass spectrometry.

| | |
|---|---|
| Maldi-TOF: | Matrix: 2,5-dihydroxybenzoic acid Method: dried droplet Instrument: Bruker BIFLEX III |
| ESI: | Bruker ApexQe hybrid 9.4 T FT-ICR (ESI) |
| NMR: | Varian 500 MHz or 300 MHz system |

ABBREVIATIONS abs. absolute (anhydrous)
AIBN Azaisobutyronitrile
CH3CN Acetonitrile
DMAP Dimethylaminopyridine
DMF N,N-Dimethylformamide
DIAD Diisopropyl azodicarboxylate
DIPEA N,N-Diisopropylethylamine
EE Ethyl acetate
EtOH Ethanol
Fmoc Fluorenylmethyloxycarbonyl
HAc Acetic acid
HATU O-(7-Azabenzotriazol-1-yl)-N,N,N',N'-tetramethyluronium
Fmoc (9H-Fluoren-9-ylmethoxy)carbonyl
MeOH Methanol
RT Room temperature
RF Reflux TEA Triethylamine
Z Benzyloxycarbonyl
>> Gradient
eq Equivalents 2-(18-azido-1,4,7,10,13,16-hexaoxaoctadecyl)terephthalic acid (Compound 1)

300 mg (1 eq) of dimethyl terephthalate and 658 mg (1 eq) of 1-tosyl-17-azido-3,6,9,12,15-pentaoxaheptadecyl were dissolved in 5 ml abs. DMF, 1971 mg (10 eq) of $K_2CO_3$ were added and the mixture stirred overnight at 65° C. 2M citric acid were added while stirring, the acidic solution shaken with $CH_2Cl_2$, the org. phase dried over $MgSO_4$, filtered and concentrated. Water was added to the residue and MeOH added until a clear solution was obtained. The solution was maintained at a pH of 12-13 by addition of 2M NaOH for 2 h, then was acidified with 2M HCl, shaken with EE, the org. phase washed with sat. NaCl, dried over $MgSO_4$, filtered, concentrated and freeze-dried. Yield 450 mg 2-(18-Fmoc amino-1,4,7,10,13,16-hexaoxaoctadecyl)terephthalic Acid (Compound 2)

240 mg (1 eq) of dimethyl terephthalate and 386 mg (1.1 eq) of 17-azido-1-hydroxy-3,6,9,12,15-pentaoxaheptadecane were dissolved in 5 ml of abs. DMF and evaporated twice with abs. DMF. After addition of 449 mg (1.5 eq) of triphenylphosphine, the mixture was cooled to 0° C., 330 µl of DIAD (1.5 eq) were added and the mixture stirred overnight at RT. After addition of 2 ml of MeOH, the mixture was concentrated, taken up in dichloromethane, washed with water, dried ($MgSO_4$), filtered, concentrated and purified on silica gel (n-hexane>>EE). The residue was dissolved in 5 ml of MeOH and 1 ml of $H_2O$, 20 mg of Pd on carbon (20%) and 0.8 ml of HAc (20%) were added, the mixture hydrogenated for 2 h, filtered, concentrated, dissolved in $H_2O$, acidified with dilute HCl (pH 3) and purified on RP18 ($H_2O$>>EtOH). The product was dissolved in 1 ml of MeOH and 10 ml of $H_2O$ and treated with 0.1 ml of NaOH (2M). After 3 h, the mixture was neutralized with dil. HCl, concentrated, dissolved in 1 ml of $H_2O$ and 6 ml of dioxane and the pH adjusted to 8-9 with TEA. After threefold addition of 70 mg of Fmoc-NHS, the mixture was concentrated and the residue purified on silica gel (EE, then EtOH:$H_2O$ 2:1) and on RP18 ($H_2O$ HCl pH 4>>EtOH) and lyophilized. Yield 98 mg 2-Allyloxyterephthalic Acid (Compound 3)

100 mg of dimethyl 2-hydroxyterephthalate and 662 mg of allyl bromide were dissolved in 1 ml of DMF and 264 mg of $CsCO_3$ were added. The suspension was stirred for 3 h at 60° C., 5 ml of HAc (20%) and 15 ml of $H_2O$ were added and the mixture shaken with dichloromethane. The org. phase was dried ($MgSO_4$), filtered and concentrated. The residue was dissolved in 10 ml of dioxane and 5 ml of $H_2O$ and 1 ml of 2M NaOH were added. After 20 h, the mixture was adjusted to pH 3 with dil. HCl and purified on RP18. Yield 72 mg 2-(3-Acetylthiopropyloxy)terephthalic Acid (Compound 4)

10 mg of compound 3 dissolved in 1 ml of MeOH and 1 ml of $H_2O$ were treated with 137 mg of thioacetic acid and irradiated with UV light for 8 h. The solution was concentrated and purified on RP18 ($H_2O$>>MeOH). Yield 9 mg Compound 5

Prepared according to "J. Carbohydrate Chemistry, 1987, 6 (1), 161-165

Compound 6

To a solution of 4 g of compound 5 and 2.16 g (4 eq) of dry lithium azide in 40 ml abs. DMF were dissolved with stirring and 8.02 g (2.2 eq) of tetrabromomethane. The yellow solution was treated at 0° C. with 3.18 g (1.1 eq) of triphenylphosphine, slowly warmed to RT and stirred for 20 h. After addition of 20 ml of MeOH, the mixture was stirred for 1 h at room temperature, which resulted in minor evolution of gas. The solvent was removed, the residue treated with a little $H_2O$ and washed 3× with toluene. The product was then extracted with EE, dried over $MgSO_4$, filtered and concentrated. Yield: 2.75 g of a slightly yellow substance.

Alternatively, lithium azide was replaced by sodium azide, which does not completely dissolve. After addition of methanol, the mixture was stirred for two days at RT.

Compound 7

2.2 g of compound 6 were dissolved in 100 ml of MeOH, 4.45 g (3 eq) of triphenylphosphine and 6 ml of $H_2O$ were added and the suspension was stirred for 18 h at room temperature. 20 ml of 20% acetic acid and 90 ml of $H_2O$ were added while stirring, the mixture stirred for half an hour, the suspension concentrated to 100 ml and shaken three times with 100 ml of dichloromethane. The aqueous phase was lyophilized. Yield: 2.67 g of solid Alternatively 1 eq of HCl was added instead of 20 ml of 20% HAc.

Compound 8

A solution of 1.0 g of compound 7 in 6 ml of abs. DMF, after addition of 607 ml (1.5 eq) of diisopropylethylamine and 832 mg (1.1 eq) of nitrophenyl 4-biphenylcarboxylate, was stirred for 17 h at RT. The solvent was removed and the residue purified on a silica gel column (EtOH:EE:HAc(20%) 1:8:1). Yield: 1.06 g Compound 9

A solution of 460 mg of compound 8 in 3 ml of MeOH was treated with 193 mg (2 eq) of cysteamine hydrochloride and 3 ml of $H_2O$ and was flushed with nitrogen for 20 min. After addition of a catalytic amount (2-3 mg) of AIBN, the mixture was irradiated with UV light (λ=366 nm) for 24 h, the solvent was removed, the residue dissolved in $H_2O$ and purified on an RP18 column (HCl pH 4>>MeOH/HCl pH 4). The product fractions were neutralized with dil. NaOH, the EtOH removed and lyophilized Yield: 525 mg Compound 10

To a solution of 26 mg (1 eq) of compound 44 and 81 mg (2.2 eq) of compound 9 in 3 ml of abs. DMF were added 47 mg (2.2 eq) of HATU and 58 µl of DIPEA. After 10 min, the mixture was concentrated and purified on RP18 ($H_2O$>>EtOH). Yield: 77 mg Compound 11

30 mg of compound 10 were dissolved in 0.8 ml of abs. DMF. After addition of 0.2 ml of piperidine, the mixture was stirred for 20 min, concentrated, coevaporated with 1 ml of DMF and purified on RP18 ($H_2O$/HAc>>EtOH). Yield: 23 mg; DC-RF: 0.43 in EtOH:EE:HAc(20%) 1:3:1; $^1$H NMR (500 MHz, $CD_3OD$) δ ppm 7.91-7.86 (m, 5H), 7.69-7.64 (m, 4H, Ar), 7.63-7.59 (m, 4H, Ar), 7.50 (d, J=1.03 Hz, 1H, Ar), 7.47-7.41 (m, 5H, Ar), 7.39-7.34 (m, 2H, Ar), 4.24 (t, J=5.75 Hz, 2H, ArOCH$_2$), 4.11-4.05 (m, 2H, H8 H8'), 3.94-3.76 (m, 4H, H9a H9a' OCH$_2$a OCH$_2$a'), 3.82 (s, 3H, OCH$_3$), 3.82 (s, 3H, OCH$_3$'), 3.71-3.44 (m, 18H, H4 H4' H5 H5' H6 H6' H7

H7' H9b H9b' OCH$_2$b OCH$_2$b'CH$_2$NH CH$_2$NH' CH$_2$NH$_2$), 2.72 (t, J=6.78 Hz, 4H, CH$_2$S CH$_2$S'), 2.69-2.58 (m, 6H, H3-e H3-e' SCH$_2$ SCH$_2$'), 1.98 (s, 3H, COCH$_3$), 1.98 (s, 3H, COCH$_3$'), 1.83-1.64 (m, 6H, CH$_2$CH$_2$CH$_2$ CH$_2$CH$_2$CH$_2$' CH$_2$CH$_2$NH$_2$, H3-a H3-a')$^{13}$C NMR (125 MHz, CD$_3$OD) δ ppm 175.1 171.0 170.3 168.9 168.4 157.7 145.6 141.2 139.4 139.3 134.4 134.3 131.4 130.0 129.9 129.1 129.0 128.1 128.0 127.3 122.1 120.7 112.9 100.3 74.8 72.2 71.1 68.5 68.4 63.7 53.9 53.4 45.1 41.7 41.0 40.4 39.5 32.1 32.0 30.9 30.8 29.5 29.2 29.0 22.8; Mass: Maldi-TOFMS m/z [C71H91N7O21S2+Na]$^+$ 1464.6 Found: 1464.1

Compound 12

To a solution of 20 mg of compound 10 in a little EtOH, water was added until turbidity occurred and the pH was adjusted to 12-13 with 2M NaOH. After 2 h, the mixture was neutralized with dil. HCl, concentrated and purified on RP18. Yield: 13 mg Compound 13

Prepared analogously to compound 10. R$_f$ 0.74 (1:3:1 EtOH:EE:HAc20%); $^1$H NMR (500 MHz, CD$_3$OD): 7.96 (d, J=8.12 Hz, 1H, Ar), 7.91-7.87 (m, 4H, Ar), 7.69-7.64 (m, 4H, Ar), 7.63-7.59 (m, 4H, Ar), 7.50 (d, J=1.42 Hz, 1H, Ar), 7.44 (dd, J=8.07, 1.53 Hz, 1H, Ar), 7.45-7.40 (m, 4H, Ar), 7.37-7.33 (m, 2H, Ar), 4.27 (dd, J=5.07, 3.83 Hz, 2H, ArOCH$_2$), 4.10-4.03 (m, 2H, H8 H8'), 3.92-3.76 (m, 14H, H4 H4' H5 H5' H6 H6' OCH$_2$a OCH$_2$a' OCH$_3$ OCH$_3$'), 3.70-3.43 (m, 34H, H7 H7' H9a H9a' H9b H9b' OCH$_2$b OCH$_2$b' CH$_2$NH CH$_2$NH' CH$_2$N3 5× CH$_2$OCH$_2$), 2.72 (t, J=6.79 Hz, 2H, SCH$_2$), 2.72 (t, J=7.10 Hz, 2H, SCH$_2$') 2.68-2.59 (m, 6H, H3-e H3-e' SCH$_2$ CH$_2$SCH$_2$'), 1.98 (s, 6H, COCH$_3$ COCH$_3$'), 1.83-1.77 (m, 4H, CH$_2$CH$_2$CH$_2$ CH$_2$CH$_2$CH$_2$'), 1.74 (t, J=12.33 Hz, 1H, H3-a), 1.73 (t, J=12.37 Hz, 1H, H3-a')$^{13}$C-NMR (125 MHz, CD$_3$OD): δ ppm 175.1 171.0 170.3 170.2 168.8 167.0 158.3 145.6 141.2 139.8 134.4 132.6 130.1 129.1 129.0 128.1 128.0 125.1 120.8 113.6 100.4 74.8 72.3 71.7 71.6 71.5 71.1 70.2 69.8 68.6 63.7 53.9 53.4 51.8 45.1 41.8 41.0 40.8 32.1 31.9 30.8 29.1 22.8; HRMS-ESI (m/z): calcd for C80H107N9O26S2 (M+2H) 837.8457 found 837.8440.

Compound 14

Prepared analogously to compound 10.

Compound 15

Method A: Prepared analogously to compound 11.

Method B: 55 mg of compound 13 were dissolved in 5 ml of MeOH, treated with 0.35 ml of 20% HAc and a spatula tip of Pd on carbon (10%) and the mixture was hydrogenated for 4 h. The suspension was filtered, the solvent was removed, the residue applied to a RP18 column with water, the column rinsed with dil. HCl, the substance eluted with H$_2$O>>EtOH, concentrated and freeze-dried. Yield 40 mg; R$_f$ 0.44 (1:3:1 EtOH:EE:HAc20%); $^1$H-NMR (500 MHz, CD$_3$OD): δ ppm 7.94-7.87 (m, 5H, Ar), 7.70-7.66 (m, 4H, Ar), 7.64-7.60 (m, 4H, Ar), 7.52 (d, J=1.22 Hz, 1H, Ar), 7.49-7.41 (m, 5H, Ar), 7.36 (t, J=7.31, 7.31 Hz, 2H, Ar), 4.58 (s, 2H, CH$_2$CH$_2$NH$_3^+$), 4.29 (dd, J=4.44, 3.94 Hz, 2H, ArOCH$_2$), 4.11-4.04 (m, 2H, H8 H8'), 3.93-3.76 (m, 14H, H5 H5' H6 H6' H9a H9a' OCH$_2$a OCH$_2$a' OCH$_3$ OCH$_3$'), 3.72-3.42 (m, 30H, H4 H4' H7 H7' H9b H9b' OCH$_2$b OCH$_2$b' CH$_2$NH CH$_2$NH' 4×CH$_2$OCH$_2$ OCH$_2$), 3.09-3.05 (m, 2H, CH$_2$NH$_3^+$), 2.74 (t, J=6.70, 6.70 Hz, 2H CH$_2$S), 2.73 (t, J=7.04, 7.04 Hz, 2H, CH$_2$S'), 2.66 (dd, J=13.14, 4.87 Hz, 2H, H3-e H3-e'), 2.67-2.59 (m, 4H SCH$_2$ SCH$_2$'), 1.98 (s, 6H, NHCOCH$_3$ NHCOCH$_3$'), 1.84-1.77 (m, 4H, CH$_2$CH$_2$CH$_2$ CH$_2$CH$_2$'), 1.76-1.69 (m, 2H, H3-a H3-a') $^{13}$C NMR (120 MHz, CD$_3$OD): δ ppm 175.1 171.0 170.3 170.2 168.8 167.4 158.1 145.6 141.2 141.1 139.7 134.4 132.3 130.1 129.2 129.1 129.0 128.1 128.1 126.4 122.1 120.9 113.5 100.3 74.8 72.3 71.1 71.0 68.5 72.2 71.5 71.4 71.3 71.2 71.1 71.0 70.3 69.8 67.9 63.7 53.9 53.5 53.4 45.1 41.8 41.0 40.7 32.1 31.9 30.9 29.2 22.8; Mass: Maldi-TOFMS m/z [C80H109N7O26S2+Na]$^+$ 1670.7 Found: 1670.3

Compound 16

Prepared analogously to compound 12. R$_f$ 0.42 (1:2:1 EtOH:EE:HAc20%); $^1$H-NMR (500 MHz, CD$_3$OD): δ ppm 7.92-7.85 (m, 4H, Ar), 7.68-7.53 (m, 10H, Ar), 7.51-7.39 (m, 5H, Ar), 7.35 (t, J=7.31, 7.31 Hz, 2H, Ar), 4.29-4.25 (m, 2H, ArOCH$_2$), 4.14-4.04 (m, 2H, H8 H8'), 3.95-3.43 (m, 40H, H4 H4' H5 H5' H6 H6' H7 H7' H9a H9a' H9b H9b' OCH$_2$a OCH$_2$a' OCH$_2$b OCH$_2$b' CH$_2$NH CH$_2$NH' 5×CH$_2$ OCH$_2$), 3.05-3.09 (m, 2H, CH$_2$NH$_3^+$), 2.78 (dd, J=12.32, 3.18 Hz, 2H, H3-e H3-e'), 2.73 (t, J=6.33, 6.33 Hz, 4H, SCH$_2$ SCH$_2$'), 2.69-2.60 (m, 4H, CH$_2$S CH$_2$S'), 2.01 (s, 6H, COCH$_3$ COCH$_3$'), 1.86-1.78 (m, 4H, CH$_2$CH$_2$CH$_2$ CH$_2$CH$_2$CH$_2$'), 1.70-1.57 (m, 2H, H3-a H3-a') $^{13}$C-NMR (125 MHz, CD$_3$OD): δ ppm 175.5 173.6 170.1 169.9 168.9 167.3 158.1 145.5 141.1 139.7 134.4 134.3 134.0 133.9 133.2 133.1 132.3 132.2 130.1 130.0 129.2 129.0 128.1 128.0 126.2 120.9 113.5 101.4 101.3 74.5 72.5 71.5 71.4 71.3 71.2 70.9 70.3 69.8 69.3 68.1 67.8 63.9 54.1 44.7 42.4 42.3 41.0 40.9 40.7 32.2 32.0 31.2 29.3 22.8; HRMS-ESI (m/z): calcd for C78H103N7Na2O26S2 (M+H) 1664.6262 found 1664.6324.

Compound 17

Prepared analogously to compound 10. R$_f$ 0.72 (1:3:1 EtOH:EE:HAc20%); $^1$H-NMR (500 MHz, CD$_3$OD): δ ppm 7.93 (d, J=8.41 Hz, 4H, Ar), 7.89 (dd, J=8.37, 3.85 Hz, 1H, Ar), 7.72 (d, J=8.41 Hz, 4H, Ar), 7.67 (dd, J=8.30, 0.96 Hz, 4H, Ar), 7.61 (d, J=7.33 Hz, 1H, Ar), 7.46 (t, J=7.63, 7.63 Hz, 4H, Ar), 7.45-7.41 (m, 1H, Ar), 7.38 (t, J=7.39, 7.39 Hz, 2H, Ar), 4.06 (ddd, J=8.52, 7.36, 3.51 Hz, 2H, H8 H8'), 3.89 (td, J=9.22, 5.80, 5.80 Hz, 2H, OCH$_2$a OCH$_2$a'), 3.86 (dd, J=10.92, 7.51 Hz, 2H, ArOCH$_2$), 3.81 (dd, J=15.64, 9.24 Hz, 2H, H9a H9a'), 3.84-3.81 (m, 8H, CH$_3$ CH$_3$' H5 H5'), 3.68 (dd, J=10.47, 1.39 Hz, 2H, H6 H6'), 3.67-3.48 (m, 10H, CH$_2$NH CH$_2$NH' H4 H4' H9b H9b' OCH$_2$b OCH$_2$b'), 3.46 (dd, J=8.71, 1.19 Hz, 2H, H7 H7'), 2.75-2.56 (m, 12H, CH$_2$SCH$_2$ CH$_2$SCH$_2$' CH$_2$SCO H3-e H3-e'), 1.98 (s, 6H, NHCOCH$_3$ NHCOCH$_3$'), 1.92 (s, 3H, SCOCH$_3$), 1.84-1.70 (m, 8H, CH$_2$CH$_2$CH$_2$ CH$_2$CH$_2$CH$_2$' H3-a H3-a' CH$_2$CH$_2$SCO) $^{13}$C NMR (125 MHz, CD$_3$OD): δ ppm 195.6 175.1 173.3 171.0 170.4 145.7 141.3 134.4 130.1 129.1 129.0 128.2 128.1 128.0 120.5 112.9 100.4 74.8 72.2 71.1 68.8 69.0 63.6 53.9 53.4 45.1 41.8 40.4 32.0 30.9 29.1 30.8 26.0 22.7 22.6; Mass: Maldi-TOFMS m/z [C73H92N6O22S3+Na]$^+$ 1524.6 Found: 1524.6

Compound 18

Prepared analogously to compound 10. Use of compound 3: 23 mg Yield 132 mg; R$_f$: 0.68 in 1:3:1, EtOH:EE: HAC20%;

Compound 19

132 mg of compound 18 were dissolved in 5 ml of pyridine. 340 mg of acetic anhydride and a catalytic amount of DMAP were added at 0° C. The solution was stirred overnight at RT, concentrated and purified on silica gel (EE>>EtOH). Yield 136 mg; R$_f$: 0.55 in 5:1 EE:EtOH; $^1$H-NMR (500 MHz, CD$_3$OD): δ ppm 7.90 (d, J=8.06 Hz, 1H, Ar), 7.82 (d, J=3.29 Hz, 2H, Ar), 7.80 (d, J=3.30 Hz, 2H, Ar), 7.67 (d, J=5.55 Hz, 2H, Ar), 7.65 (d, J=5.64 Hz, 2H, Ar), 7.63-7.59 (m, 4H, Ar), 7.50 (d, J=1.40 Hz, 1H, Ar), 7.47-7.41 (m, 5H, Ar), 7.36 (t, J=7.35, 7.35 Hz, 2H, Ar), 6.11 (tdd, J=16.97, 10.71, 5.41, 5.41 Hz, 1H, CH=CH$_2$), 5.53-5.45 (m, 2H, H4 H4'), 5.42 (ddd, J=17.05, 2.78, 1.36 Hz, 1H, CH=CH$_2$a), 5.31 (ddd, J=10.50, 2.52, 1.29 Hz, 1H, CH=CH$_2$b), 5.27 (dd, J=9.08, 2.11 Hz, 2H, H7 H7'), 4.80 (ddd, J=12.10, 10.61, 4.59 Hz, 2H, H8 H8'), 4.70 (td, J=5.57, 1.37, 1.37 Hz, 1H, ArOC$\underline{H_2}$a), 4.22 (td, J=10.77, 1.88, 1.88 Hz, 1H, ArOC$\underline{H_2}$b), 4.02 (t, J=10.51, 10.51 Hz, 2H, H5 H5'), 3.92-3.86 (m, 4H, OCH$_2$a OCH$_2$a' H9a H9a'), 3.80 (s, 3H, COOCH$_3$), 3.80 (s, 3H, COOCH$_3$'), 3.61-3.53 (m, 4H, CH$_2$NH CH$_2$NH'), 3.44-3.39 (m, 2H, OCH$_2$b OCH$_2$b'), 3.37 (dd, J=14.45, 7.68 Hz, 1H, H9b), 3.37 (dd, J=14.57, 7.45 Hz, 1H, H9b'), 2.77-2.72 (m, 4H, CH$_2$S CH$_2$S'), 2.68-2.60 (m, 6H, SCH$_2$ SCH$_2$' H3-e H3-e'), 2.17 2.12 2.11 1.98 (4×s, 18H, 6×COCH$_3$), 1.86-1.78 (m, 12H, 2×COCH$_3$ CH$_2$C$\underline{H_2}$CH$_2$ CH$_2$C$\underline{H_2}$CH$_2$' H3-a H3-a'); $^{13}$C NMR (125 MHz, CD$_3$OD): δ ppm 173.5 172.7 172.6 172.3 172.2 171.8 170.1 170.0 169.9 169.8 168.8 167.3 157.9 145.7 141.2 139.5 134.3 133.8 132.3 130.1 129.2 128.9 128.2 128.1 126.4 120.6 119.4 113.5 100.1 73.3 70.8 70.6 70.0 69.9 71.2 64.5 53.3 50.2 41.4 41.0 40.4 39.2 32.2 32.0 31.1 31.0 29.1 28.9 22.7 21.5 21.2 20.8; Mass: Maldi-TOFMS m/z [C83H100N6O27S2+H]$^+$ 1677.61 Found: 1677.6

Compound 20

Prepared analogously to compound 10.

Compound 21

Prepared analogously to compound 12. HRMS-ESI (m/z): calcd for C63H81N7Na2O20S2 (M−2Na) 659.7494 found 659.7539.

Compound 22

Prepared analogously to compound 10 using N-(6-Fmo-caminohexanoyl)glutamic acid. Saponified analogously to compound 12. R$_f$ 0.21 in 1:3:1 EtOH:EE:HAc(20%); $^1$H NMR (500 MHz, CD$_3$OD) δ ppm 7.94-7.89 (m, 4H, Ar), 7.73-7.69 (m, 4H, Ar), 7.67-7.65 (m, 4H, Ar), 7.46 (t, J=7.66 Hz, 4H, Ar), 7.37 (t, J=7.39 Hz, 2H, Ar), 4.30 (dd, J=8.87, 5.13 Hz, 1H, CHNH), 4.12-4.07 (m, 2H, H8 H8'), 3.91-3.81 (m, 4H, OCH$_2$a OCH$_2$a' H9a H9a'), 3.73-3.63 (m, 6H, H5 H5' H6 H6' H4 H4'), 3.59-3.49 (m, 4H, H9b H9b' OCH$_2$b OCH$_2$b'), 3.47-3.43 (m, 2H, H7 H7'), 3.39-3.27 (m, 4H, CH$_2$NH CH$_2$NH), 2.94 (t, J=7.53 Hz, 1H, CH$_2$NH$_2$), 2.87-2.81 (m, 2H, H3-e H3-e'), 2.67-2.54 (m, 8H, CH$_2$SCH$_2$ CH$_2$SCH$_2$'), 2.33-2.24 (m, 4H, CH$_2$CO CH$_2$CO'), 2.10-1.88 (m, 2H, C$\underline{H_2}$CH), 2.01 (s, 3H, COCH$_3$), 2.01 (s, 3H, COCH$_3$'), 1.82-1.75 (m, 4H, SCH$_2$C$\underline{H_2}$), 1.70-1.55 (m, 6H, H3-a H3-a' C$\underline{H_2}$CH$_2$CH$_2$ CH$_2$NH$_2$), 1.42-1.34 (m, 2H, C$\underline{H_2}$CH$_2$CH$_2$NH$_2$); $^{13}$C NMR (125 MHz, CD$_3$OD): δ ppm 175.9 175.5 175.1 174.5 174.0 170.0 145.6 141.3 134.5 130.1 129.1 129.0 128.2 128.1 102.0 74.3 72.7 71.5 71.4 69.7 69.6 63.9 54.7 54.3 44.7 44.6 42.8 40.7 40.3 39.9 36.3 33.4 32.2 31.3 29.3 29.2 28.3 26.8 26.0 22.7; HRMS-ESI (m/z): calcd for C69H92N8Na2O21S2 (M−2Na) 716.2915 found 716.2900.

Compound 23

91 mg of adipic acid were dissolved in 2 ml of abs. DMF and 14 mg of HATU and 173 mg of DIPEA were added. After 30 s, 45 mg of compound 11 were added and after 5 min the mixture was concentrated and purified on RP18. Yield: 27 mg; R$_f$ 0.58 in 1:3:1 EtOH:EE:HAc(20%); $^1$H-NMR (500 MHz, CD$_3$OD): δ ppm 7.90 (d, J=2.32 Hz, 2H, Ar), 7.89 (d, J=2.67 Hz, 2H, Ar), 7.86 (d, J=8.05 Hz, 1H, Ar), 7.66 (d, J=7.83 Hz, 4H, Ar), 7.61 (dd, J=7.25, 1.07 Hz, 4H, Ar), 7.49 (d, J=1.29 Hz, 1H, Ar), 7.46-7.40 (m, 5H, Ar), 7.37-7.33 (m, 2H, Ar), 4.15 (t, J=5.99, 5.99 Hz, 2H, ArOCH$_2$), 4.08 (ddd, J=11.25, 7.26, 3.46 Hz, 2H, H8 H8'), 3.92-3.78 (m, 12H, H9a H9a' H5 H5' OCH$_2$a OCH$_2$a' OCH$_3$ OCH$_3$'), 3.69 (dd, J=10.45, 1.34 Hz, 2H, H6 H6'), 3.68-3.44 (m, 12H, H4 H4' H7 H7' H9b H9b' OCH$_2$b OCH$_2$b' C$\underline{H_2}$NHCOArCONHC$\underline{H_2}$), 3.36 (t, J=6.60, 6.60 Hz, 2H, CH$_2$NH), 2.73 (dd, J=12.64, 6.85 Hz, 4H, CH$_2$S CH$_2$S'), 2.69-2.59 (m, 6H, SCH$_2$ SCH$_2$' H3-e H3-e'), 2.21-2.12 (m, 4H, CH$_2$CO CH$_2$COO), 2.04-2.00 (m, 2H, ArOCH$_2$C$\underline{H_2}$), 1.98 (s, 6H, NHCOCH$_3$ NHCOCH$_3$'), 1.85-1.77 (m, 4H, CH$_2$C$\underline{H_2}$CH$_2$ CH$_2$C$\underline{H_2}$CH$_2$'), 1.73 (t, J=12.38, 12.38 Hz, 2H, H3-a H3-a'), 1.63-1.56 (m, 4H, CH$_2$C$\underline{H_2}$CH$_2$CH$_2$) $^{13}$C NMR (75 MHz, CD$_3$OD): δ ppm 182.4 176.4 175.1 171.0 170.3 169.0 167.5 158.3 145.6 141.2 139.6 134.4 132.2 130.1 129.1 129.0 128.1 128.0 126.4 120.6 112.8 100.4 74.8 72.3 71.1 68.5 67.7 63.7 53.9 53.4 45.1 41.8 41.7 41.0 40.5 38.7 37.2 37.1 32.1 31.9 30.8 30.1 29.2 29.0 27.2 27.1 22.8

Compound 24

Prepared analogously to compound 23 using 3,3'-dithiopropionic acid. R$_f$ 0.63 in 1:3:1 EtOH:EE:HAc(20%);

Compound 25

13 mg of compound 23 were dissolved in water, the solution adjusted to pH 12-13 with 2 M NaOH, neutralized after 2 h and purified on RP18. Yield: 10 mg; R$_f$ 0.31 in 1:3:1 EtOH:EE:HAc(20%); $^1$H-NMR (500 MHz, CD$_3$OD): δ ppm 7.90-7.87 (m, 4H, Ar), 7.84 (dd, J=8.01, 0.75 Hz, 1H, Ar), 7.68-7.63 (m, 4H, Ar), 7.63-7.59 (m, 4H, Ar), 7.48 (d, J=1.08 Hz, 1H, Ar), 7.45-7.40 (m, 5H, Ar), 7.37-7.33 (m, 2H, Ar), 4.15 (t, J=6.40, 6.40 Hz, 2H, CH$_2$OAr), 4.13-4.07 (m, 2H, H8 H8'), 3.90 (td, J=9.67, 6.23, 6.23 Hz, 2H, OCH$_2$a OCH$_2$a'), 3.85 (dd, J=13.37, 2.41 Hz, 2H, H9a H9a'), 3.73-3.41 (m, 20H, H4 H4' H5 H5' H6 H6' H7 H7' H9b H9b' OCH$_2$b OCH$_2$b' CH$_2$NH CH$_2$NH'), 3.37 (t, J=6.76, 6.76 Hz, 2H, C$\underline{H_2}$NHCOCH$_3$), 2.86-2.80 (m, 2H, H3-e H3-e), 2.76-2.72 (m, 4H, CH$_2$S CH$_2$S'), 2.69-2.61 (m, 4H, SCH$_2$ SCH$_2$'), 2.26-2.18 (m, 4H, CH$_2$CO CH$_2$COO), 2.06-2.02 (m, 2H, OCH$_2$C$\underline{H_2}$), 2.00 (s, 6H, COCH$_3$ COCH$_3$'), 1.86-1.79 (m, 4H, CH$_2$C$\underline{H_2}$CH$_2$ CH$_2$C$\underline{H_2}$CH$_2$'), 1.66-1.54 (m, 6H, H3-a H3-a' CH$_2$C$\underline{H_2}$CH$_2$CH$_2$) $^{13}$C NMR (75 MHz, CD$_3$OD): δ ppm 176.2 175.5 174.5 174.4 170.0 169.9 169.0 167.7 158.0 145.5 141.3 139.6 134.5 132.1 130.0 129.1 129.0 128.1 128.0 126.5 120.6 112.8 102.0 (2C, C2 C2'), 74.3 71.5 71.4 69.7 67.8 64.0 63.9 54.2 44.6 42.8 41.1 40.5 37.3 36.9 32.2 31.9 31.5 31.4 30.1 29.4 29.3 26.8 26.3 22.7

Compound 26

9 mg of compound 16 were dissolved in 1 ml of abs. DMF and 53 mg of adipic acid-diNHS and 46 μl of DIPEA were added. The mixture was concentrated after 1 h, treated with a little water and shaken three times with EE. The aqueous phase was filtered and purified on RP18 (H$_2$O>>CH$_3$CN). The acetonitrile was removed at RT under reduced pressure. The aqueous residue was frozen with liquid nitrogen and lyophilized. The entire aqueous work-up was carried out in max. 2 h. Yield: 7 mg Compound 27

2 mg of 6-maleimidohexanoic acid-NHS were dissolved in 1 ml of DMF and, after addition of 3.5 mg of HATU and 3.5 mg of DIPEA, were added to 15 mg of compound 16. After 5 min, the solution was concentrated and purified on RP18. Yield: 14 mg; R$_f$ 0.29 in 1:3:1 EtOH:EE:HAc(20%); $^1$H-NMR (500 MHz, CD$_3$OD): δ ppm 7.93-7.87 (m, 5H, Ar), 7.69-7.65 (m, 4H, Ar), 7.61 (d, J=7.21 Hz, 4H, Ar), 7.52 (d, J=1.10 Hz, 1H, Ar), 7.47-7.40 (m, 5H, Ar), 7.37-7.33 (m, 2H, Ar), 6.77 (s, 2H, CH=CH), 4.30-4.27 (m, 2H, ArOCH$_2$), 4.13-4.05 (m, 2H, H8 H8'), 3.94-3.40 (m, 44H, H4 H4' H5 H5' H6 H6' H7 H7' H9a H9a' H9b H9b' OCH$_2$a OCH$_2$a' OCH$_2$b OCH$_2$b' CH$_2$NH CH$_2$NH' CH$_2$NH'' CH$_2$N 5×CH$_2$OCH$_2$), 2.87-2.80 (m, 2H, H3-e H3-e'), 2.76-2.72 (m, 4H, CH$_2$S CH$_2$S'), 2.69-2.62 (m, 4H, SCH$_2$ SCH$_2$'), 2.15 (t, J=7.45, 7.45 Hz, 2H, CH$_2$CO CH$_2$CO'), 2.00 (s, 6H, COCH$_3$ COCH$_3$'), 1.86-1.79 (m, 4H, CH$_2$C$\underline{H_2}$CH$_2$ CH$_2$C$\underline{H_2}$CH$_2$'), 1.63-1.50 (m, 6H, H3-a H3-a' CH$_2$C$\underline{H_2}$CH$_2$ CH$_2$C$\underline{H_2}$CH$_2$), 1.38-1.22 (m, 2H, CH$_2$C$\underline{H_2}$CH$_2$CH$_2$CH$_2$) $^{13}$C NMR (125 MHz, CD$_3$OD): δ ppm 179.3 176.1 175.8 175.5 172.6 169.9 169.8 168.8 167.2 158.2 145.5 141.3 141.2 139.8 135.4 134.5 132.3 130.1 129.1 129.0 128.1 128.0 126.2 120.9 113.5

102.0 74.3 72.7 71.6 71.5 71.4 71.2 70.8 70.2 69.9 69.7 69.6 64.0 63.9 54.2 44.7 42.8 41.0 40.8 40.3 38.5 36.8 32.2 32.0 31.5 29.5 29.4 29.3 27.4 26.5 22.7

Compound 28

50 mg of compound 15 and 16 mg of Fmoc-protected monohydrazinosuccinic acid were dissolved in 1 ml of DMF. 15 mg of HATU and 39 µl of DIPEA were added and after 5 min the solution was concentrated and purified on RP18. The product was dissolved in a little EtOH, diluted with water until turbidity appeared and the solution adjusted to pH 12-13 with dil. NaOH. The solution was neutralized after 3 h and purified on RP18. Yield 16 mg; $R_f$ 0.33 in 1:3:1 EtOH:EE:HAc(20%); $^1$H NMR (500 MHz, CD$_3$OD) δ ppm 7.93-7.86 (m, 5H, Ar), 7.68-7.64 (m, 4H, Ar), 7.62-7.59 (m, 4H, Ar), 7.51 (d, J=1.34 Hz, 1H, Ar), 7.47-7.40 (m, 5H, Ar), 7.37-7.32 (m, 2H, Ar), 4.28 (dd, J=4.63, 4.03 Hz, 2H, ArOCH$_2$), 4.13-4.05 (m, 2H, H8 H8'), 3.93-3.81 (m, 6H, OCH$_2$a OCH$_2$a' H9a H9a' ArOCH$_2$CH$_2$), 3.72-3.40 (m, 32H, H4 H4' H5 H5' H6 H6' H7 H7' H9b H9b' OCH$_2$b OCH$_2$b' 5×OCH$_2$CH$_2$), 3.32-3.28 (m, 4H, 2×CH$_2$NH), 2.85-2.80 (m, 2H, H3-e H3-e'), 2.74 (t, J=6.87 Hz, 4H, CH$_2$S CH$_2$S'), 2.69-2.61 (m, 4H, SCH$_2$ SCH$_2$'), 2.51-2.44 (m, 2H, COCH$_2$), 2.43-2.39 (m, 2H, COCH$_2$), 2.00 (s, 6H, COCH$_3$ COCH$_3$'), 1.86-1.78 (m, 4H, CH$_2$CH$_2$CH$_2$ CH$_2$CH$_2$CH$_2$'), 1.62-1.52 (m, 2H, H3-a H3-a'))$^{13}$C-NMR (125 MHz, CD$_3$OD): δ ppm 175.5 174.6 174.5 174.4 174.0 169.9 169.8 168.9 167.3 158.2 145.5 141.2 139.8 134.5 132.3 130.1 130.0 129.1 129.0 128.1 128.0 126.2 120.9 113.5 102.0 101.3 74.3 72.7 71.6 71.4 71.3 71.2 70.8 70.3 69.8 69.7 64.0 63.9 54.2 44.7 42.9 42.8 41.0 40.8 40.4 32.2 32.0 31.5 30.5 29.5 29.4 22.7; HRMS-ESI (m/z): calcd for C82H109N9Na2O28S2 (M−2Na) 865.8417 found 865.8499.

Compound 29

Prepared using 2-(9-Fmoc-amino)terephthalic acid analogously to compound 10. Saponified analogously to compound 12. $R_f$ 0.32 (1:3:1 EtOH:EE:HAc20%); $^1$H NMR (300 MHz, CD$_3$OD): δ ppm 7.88 (d, J=8.37 Hz, 4H, Ar), 7.66 (d, J=8.36 Hz, 4H, Ar), 7.61 (d, J=7.08 Hz, 4H, Ar), 7.39-7.49 (m, 5H, Ar), 7.35 (t, J=7.24, 7.24 Hz, 2H, Ar), 7.13 (d, J=1.59 Hz, 1H, Ar), 6.97 (dd, J=8.16, 1.70 Hz, 1H, Ar), 4.10 (dt, J=8.65, 8.39, 3.23 Hz, 2H, H8 H8'), 3.94-3.43 (m, 20H, H4 H4' H5 H5' H6 H6' H7 H7' H9a H9a' H9b H9b' OCH$_2$a OCH$_2$a' OCH$_2$b OCH$_2$b' CH$_2$NH CH$_2$NH'), 2.75-2.58 (m, 10H, H3-e H3-e' CH$_2$SCH$_2$SCH$_2$'), 1.86-1.76 (m, 4H, CH$_2$CH$_2$CH$_2$ CH$_2$CH$_2$CH$_2$'), 1.72 (t, J=11.29, 11.29 Hz, 2H, H3-a H3-a')$^{13}$C-NMR (75 MHz, CD$_3$OD): δ ppm 175.3 172.2 171.1 170.3 170.0 145.6 141.3 140.0 134.4 130.0 129.1 129.0 128.1 128.0 120.0 116.9 115.6 100.2 74.8 72.3 71.4 68.9 63.7 53.9 44.9 41.9 40.9 40.5 32.1 32.0 31.0 29.3 22.8; HRMS-ESI (m/z): calcd for C66H78Na2N6O20S2 [M−2Na] 676.7416 found 676.7445.

Compound 30

Prepared analogously to compound 8.

Compound 31

Prepared analogously to compound 9.

Compound 32

Prepared analogously to compound 13.

Compound 33

Prepared from compound 32 analogously to compound 10. Saponified analogously to compound 12. HRMS-ESI (m/z): calcd for C78H101N9Na2O28S2 (M−2Na) 837.8104 found 837.8132.

Compound 34

Prepared using 2-hydroxyterephthalic acid analogously to compound 29. $R_f$ 0.34 (1:3:1 EtOH:EE:HAc20%); $^1$H NMR (300 MHz, CD$_3$OD): δ ppm 7.93-7.88 (m, 4H, Ar), 7.85 (d, J=8.22 Hz, 1H, Ar), 7.67 (d, J=8.48 Hz, 4H, Ar), 7.62 (d, J=7.14 Hz, 4H, Ar), 7.47-7.39 (m, 4H, Ar), 7.35 (t, J=7.23, 7.23 Hz, 2H, Ar), 7.11 (d, J=1.51 Hz, 1H, Ar), 6.92 (d, J=7.99 Hz, 1H, Ar), 4.13-4.04 (m, 2H, H8 H8'), 3.94-3.39 (m, 20H, H4 H4' H5 H5' H6 H6' H7 H7' H9a H9a' H9b H9b' OCH$_2$a OCH$_2$a' CH$_2$COArCONHCH$_2$ OCH$_2$b OCH$_2$b'), 2.88-2.80 (m, 2H, H3-e H3-e'), 2.75-2.60 (m, 8H, CH$_2$SCH$_2$ CH$_2$SCH$_2$'), 1.997 (s, 3H, COCH$_3$), 1.995 (s, 3H, COCH$_3$), 1.88-1.76 (m, 4H, CH$_2$CH$_2$CH$_2$ CH$_2$CH$_2$CH$_2$'), 1.65-1.54 (m, 2H, H3-a H3-a')$^{13}$C-NMR (75 MHz, CD$_3$OD): δ ppm 175.5 174.5 170.7 170.4 170.1 145.6 141.3 134.5 130.0 129.1 129.0 139.5 128.1 128.0 102.0 74.3 72.6 71.6 69.7 64.0 54.2 44.5 42.8 40.9 40.2 32.4 31.9 31.5 31.4 29.4 29.3 22.7; HRMS-ESI (m/z): calcd for C66H78Na2N6O21S2 [M−2Na] 677.2336 found 677.2319.

Compound 41

240 mg of HO(O)CCH$_2$CH$_2$C(O)NH—[CH$_2$CH$_2$O]$_n$ CH$_2$CH$_2$—NHC(O)CH$_2$CH$_2$C(O)OH (Iris Biotec GmbH, alpha,omega-biscarboxy poly(ethylene glycol), PEG MW 2000 Dalton) were dissolved in 0.5 ml of abs. DMF and 4.9 mg of HATU and 46.7 µl of DIPEA were added. The solution was directly added to 22 mg of compound 15 dissolved in 0.5 ml of DMF. After removal of the solvent, the substance was purified on RP18 (firstly dil. NaHCO$_3$ pH 9, then 5 column volumes of dil. NaHCO$_3$ pH 9:EtOH 7:3, then 1 column volume of water:EtOH 7:3, then water>>EtOH) and freeze-dried. Yield 43 mg (99%); $R_f$ 0.21 (1:1:1:2 EtOH:EE:HAc20%:dioxane); the Maldi-Tof spectrum revealed molar masses of 3412 to 4163 with a mean molar mass of 3806 (n=35 to 51).

2-(3-Fmoc amino)propyloxyterephthalic Acid (Compound 44)

Prepared analogously to compound 2.

Compound 45

Compound 5 was irradiated and purified analogously to the preparation of compound 9 with cysteamine. The product was then reacted with terephthalic acid analogously to the preparation of compound 10 and saponified analogously to compound 12. HRMS-ESI (m/z): calcd for C40H60Na2N4O20S2 [M−2Na] 490.1627 found 490.1617.

Compound 46

Prepared analogously to compound 10. Saponified analogously to compound 12. HRMS-ESI (m/z): calcd for C66H78Na2N6O20S2 [M−2Na] 669.2362 found 669.2353.

The prepared sialic acid derivatives of the formula (I) are listed in Table 1.

TABLE I

| No. | Structure |
|---|---|
| 11 | 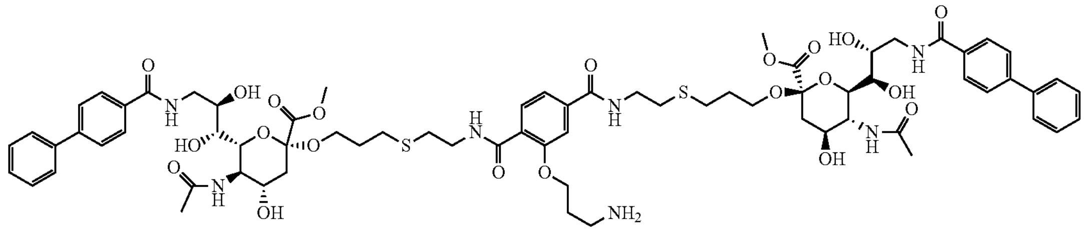 [SMILES: COC(=O)[C@@]1(OCCCSCCNC(=O)c2ccc(C(=O)NCCSCCCO[C@]3(C(=O)OC)C[C@H](O)[C@@H](NC(C)=O)[C@H]([C@H](O)[C@H](O)CNC(=O)c4ccc(-c5ccccc5)cc4)O3)c(OCCCN)c2)C[C@H](O)[C@@H](NC(C)=O)[C@H]([C@H](O)[C@H](O)CNC(=O)c2ccc(-c3ccccc3)cc2)O1] |
| 12 | 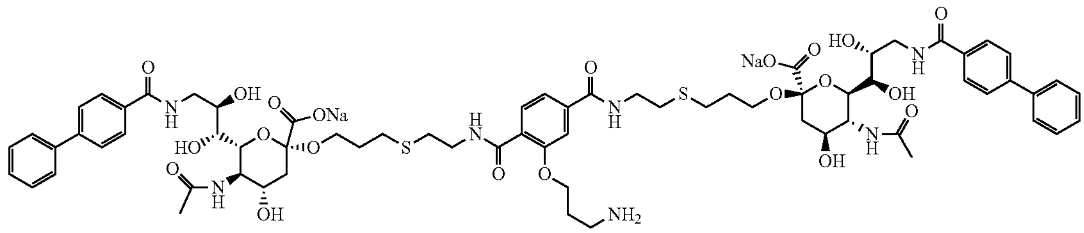 |
| 13 | 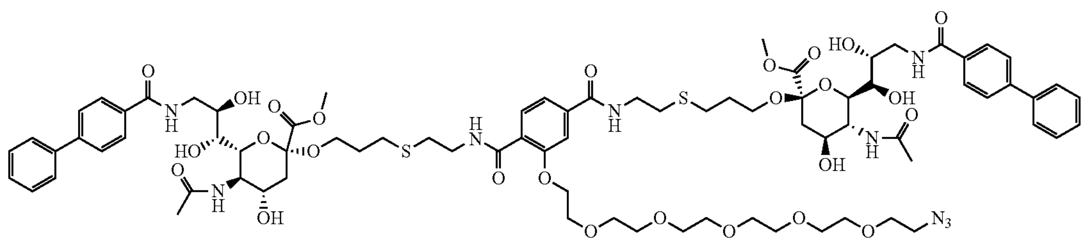 [SMILES: COC(=O)[C@@]1(OCCCSCCNC(=O)c2ccc(C(=O)NCCSCCCO[C@]3(C(=O)OC)C[C@H](O)[C@@H](NC(C)=O)[C@H]([C@H](O)[C@H](O)CNC(=O)c4ccc(-c5ccccc5)cc4)O3)c(OCCOCCOCCOCCOCCOCCN=[N+]=[N-])c2)C[C@H](O)[C@@H](NC(C)=O)[C@H]([C@H](O)[C@H](O)CNC(=O)c2ccc(-c3ccccc3)cc2)O1] |
| 15 | 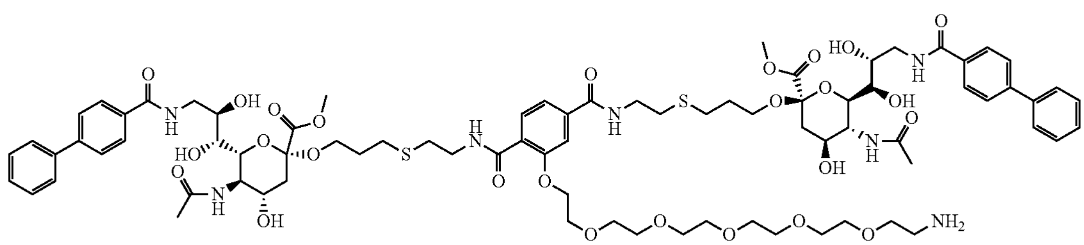 [SMILES: COC(=O)[C@@]1(OCCCSCCNC(=O)c2ccc(C(=O)NCCSCCCO[C@]3(C(=O)OC)C[C@H](O)[C@@H](NC(C)=O)[C@H]([C@H](O)[C@H](O)CNC(=O)c4ccc(-c5ccccc5)cc4)O3)c(OCCOCCOCCOCCOCCOCCN)c2)C[C@H](O)[C@@H](NC(C)=O)[C@H]([C@H](O)[C@H](O)CNC(=O)c2ccc(-c3ccccc3)cc2)O1] |
| 16 | 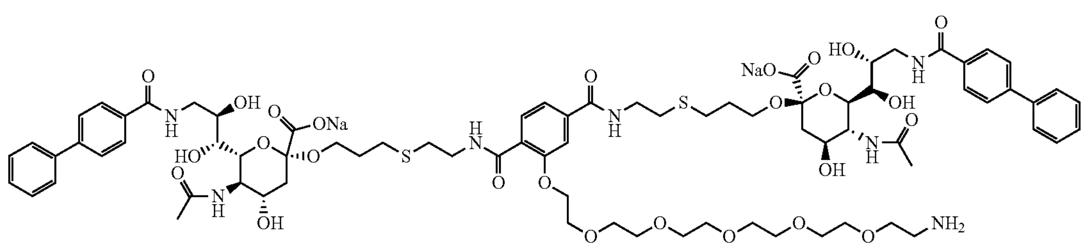 |
| 17 | 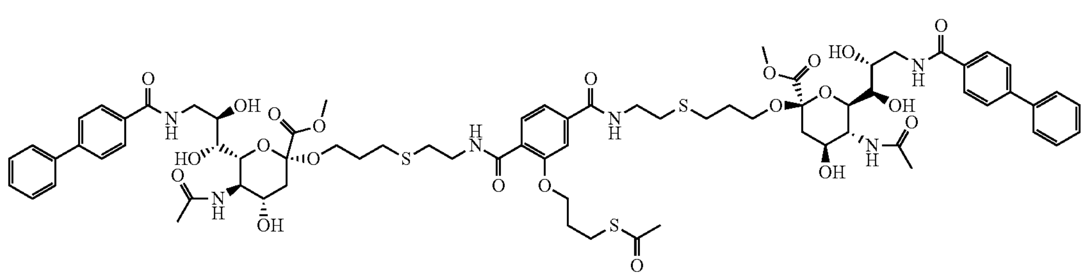 [SMILES: COC(=O)[C@@]1(OCCCSCCNC(=O)c2ccc(C(=O)NCCSCCCO[C@]3(C(=O)OC)C[C@H](O)[C@@H](NC(C)=O)[C@H]([C@H](O)[C@H](O)CNC(=O)c4ccc(-c5ccccc5)cc4)O3)c(OCCCSC(C)=O)c2)C[C@H](O)[C@@H](NC(C)=O)[C@H]([C@H](O)[C@H](O)CNC(=O)c2ccc(-c3ccccc3)cc2)O1] |

TABLE I-continued

| No. | Structure |
|-----|-----------|
| 18 | 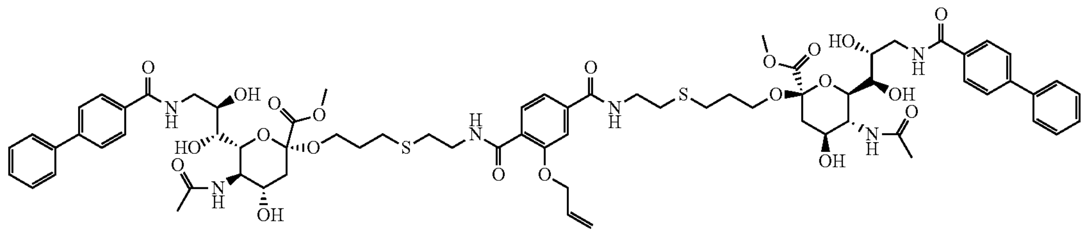 [SMILES: C=CCOc1cc(C(=O)NCCSCCCO[C@]2(C(=O)OC)C[C@H](O)[C@@H](NC(C)=O)[C@H]([C@H](O)[C@H](O)CNC(=O)c3ccc(-c4ccccc4)cc3)O2)ccc1C(=O)NCCSCCCO[C@]1(C(=O)OC)C[C@H](O)[C@@H](NC(C)=O)[C@H]([C@H](O)[C@H](O)CNC(=O)c2ccc(-c3ccccc3)cc2)O1] |
| 19 | 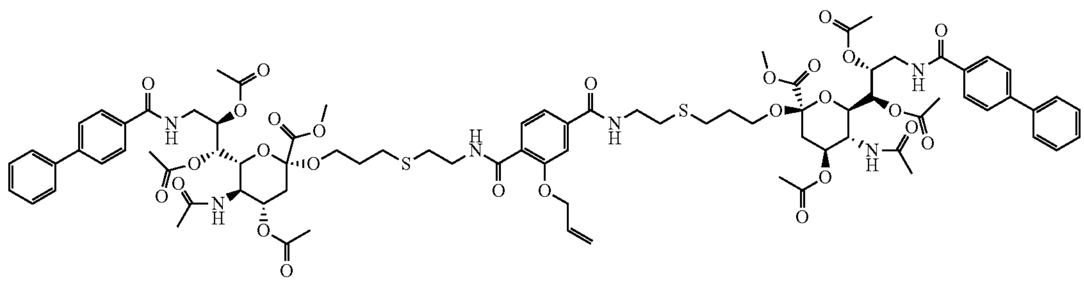 [SMILES: C=CCOc1cc(C(=O)NCCSCCCO[C@]2(C(=O)OC)C[C@H](OC(C)=O)[C@@H](NC(C)=O)[C@H]([C@H](OC(C)=O)[C@@H](CNC(=O)c3ccc(-c4ccccc4)cc3)OC(C)=O)O2)ccc1C(=O)NCCSCCCO[C@]1(C(=O)OC)C[C@H](OC(C)=O)[C@@H](NC(C)=O)[C@H]([C@H](OC(C)=O)[C@@H](CNC(=O)c2ccc(-c3ccccc3)cc2)OC(C)=O)O1] |
| 21 | 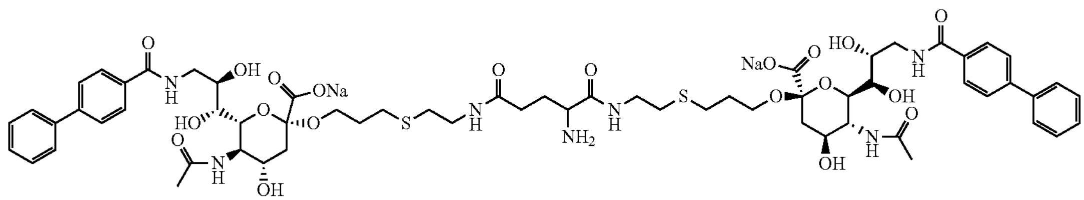 |
| 22 | 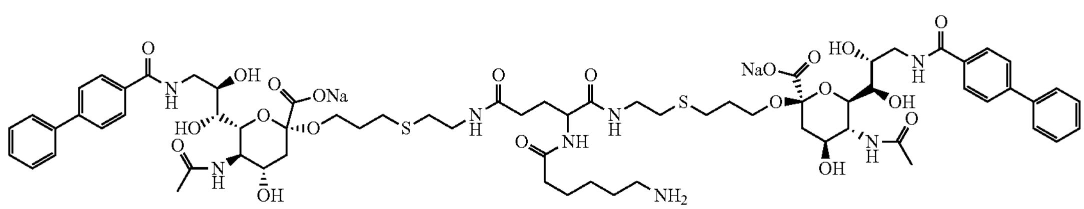 |
| 23 | 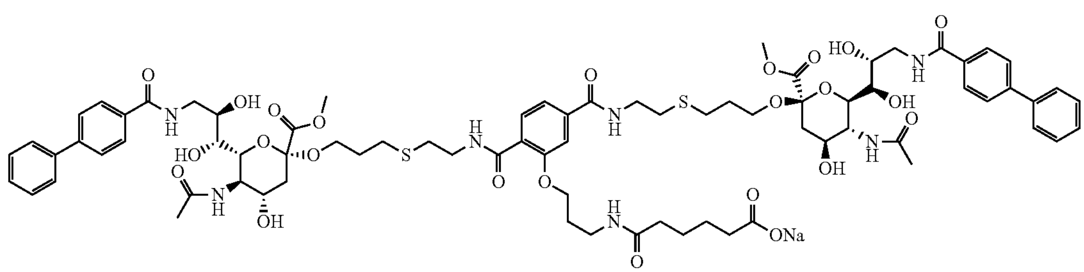 |
| 24 | 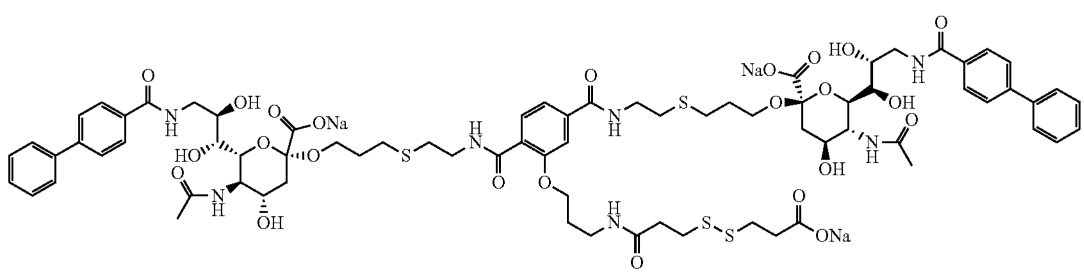 |

TABLE I-continued

| No. | Structure |
|---|---|
| 25 | 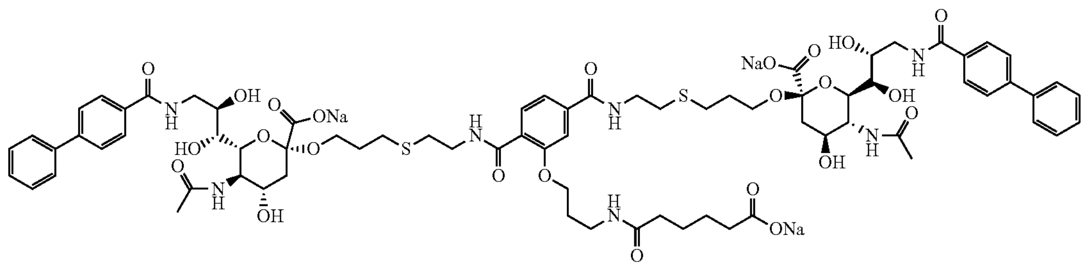 |
| 26 | 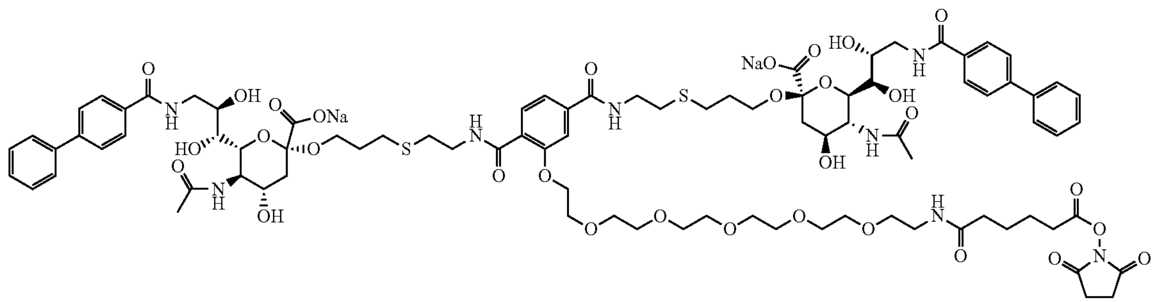 |
| 27 | 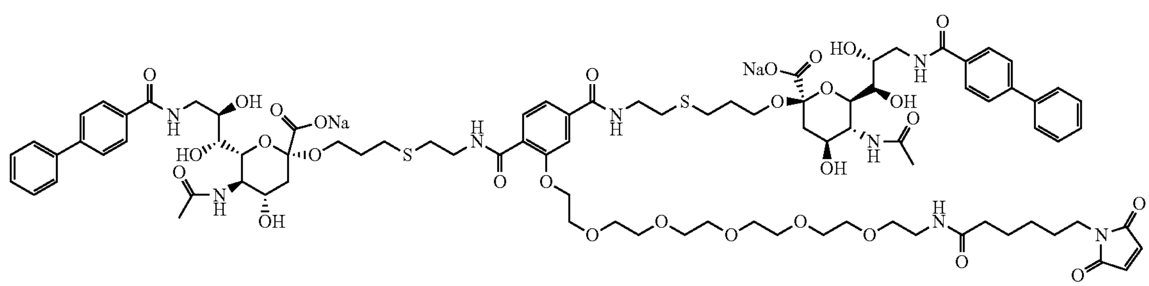 |
| 28 | 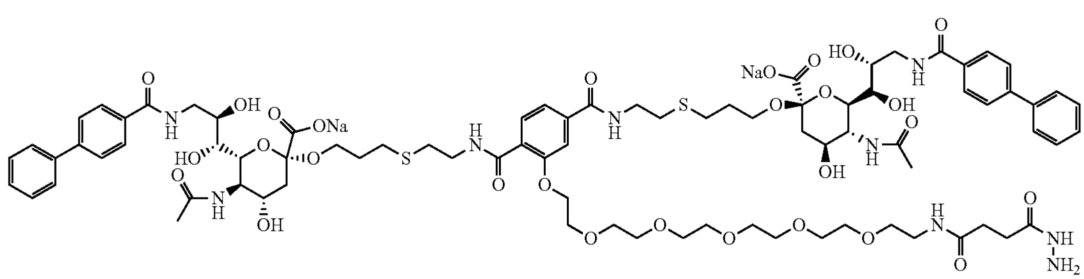 |
| 29 | 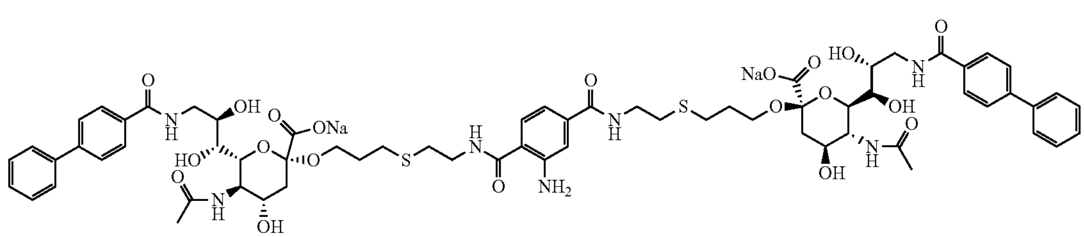 |
| 32 | 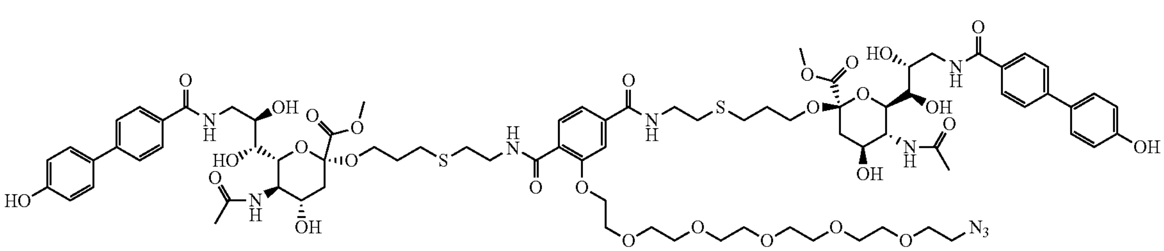 [SMILES: COC(=O)[C@@]1(OCCCSCCNC(=O)c2ccc(C(=O)NCCSCCCO[C@]3(C(=O)OC)C[C@H](O)[C@@H](NC(C)=O)[C@H]([C@H](O)[C@H](O)CNC(=O)c4ccc(-c5ccc(O)cc5)cc4)O3)c(OCCOCCOCCOCCOCCOCCN=[N+]=[N-])c2)C[C@H](O)[C@@H](NC(C)=O)[C@H]([C@H](O)[C@H](O)CNC(=O)c2ccc(-c3ccc(O)cc3)cc2)O1] |

TABLE I-continued

| No. | Structure |
|---|---|
| 33 | 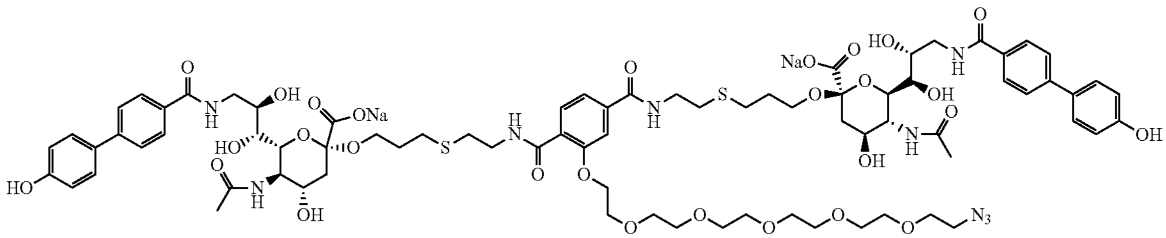 |
| 34 | 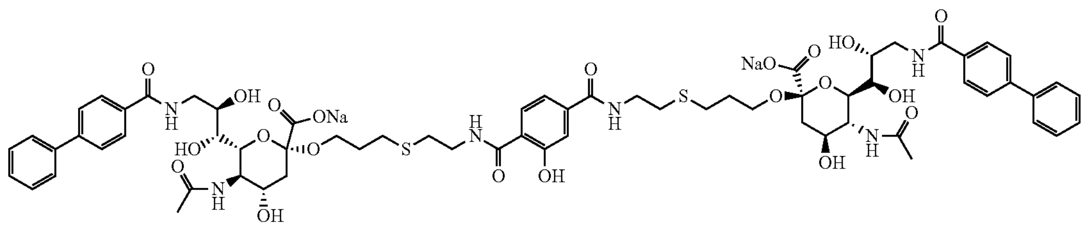 |
| 41 | | n = 35-51

Preparation of Low Molecular Weight Conjugates

Compound 35

4.7 mg of biotin were dissolved in 1 ml of abs. DMF, and after addition of 7.3 mg of HATU and 6.2 mg of DIPEA, 28 mg of compound 16 were added. The solution was stirred for 10 min, concentrated and the residue purified on RP18. Yield 28 mg; $R_f$ 0.14 (1:3:1 EtOH:EE:HAc20%); $^1$H NMR (500 MHz, CD$_3$OD): δ ppm 7.92-7.87 (m, 4H, Ar), 7.94 (d, J=8.08 Hz, 1H, Ar), 7.69-7.65 (m, 4H, Ar), 7.63-7.60 (m, 4H, Ar), 7.52 (d, J=1.37 Hz, 1H, Ar), 7.46 (dd, J=8.19, 1.55 Hz, 1H, Ar), 7.46-7.40 (m, 4H, Ar), 7.38-7.33 (m, 2H, Ar), 4.46 (ddd, J=7.86, 5.05, 0.66 Hz, 1H, CH-biotin), 4.30-4.25 (m, 3H, ArOCH$_2$ CH-biotin), 4.13-4.06 (m, 2H, H8 H8'), 3.94-3.83 (m, 6H, H9a H9a' OCH$_2$a OCH$_2$a' ArOCH$_2$CH$_2$), 3.75-3.42 (m, 34H, H4 H4' H5 H5' H6 H6' H7 H7' H9b H9b' OCH$_2$b OCH$_2$b' CH$_2$NH CH$_2$NH' 4×OCH$_2$CH$_2$ CH$_2$CH$_2$NH), 3.33-3.31 (m, 2H, CH$_2$NH), 3.15 (ddd, J=8.76, 5.64, 4.59 Hz, 1H, biotin-SCH), 2.89 (dd, J=12.75, 5.00 Hz, 1H, biotin-SCH$_2$b), 2.86-2.81 (m, 2H, H3-e H3-e'), 2.77-2.72 (m, 4H, CH$_2$S CH$_2$S'), 2.71-2.61 (m, 5H, SCH$_2$ SCH$_2$' biotin-SCH$_2$a), 2.19 (t, J=7.37 Hz, 2H, CH$_2$CO), 2.01 (s, 6H, COCH$_3$ COCH$_3$'), 1.87-1.79 (m, 4H, SCH$_2$CH$_2$ SCH$_2$CH$_2$'), 1.75-1.51 (m, 6H, H3-a H3-a' CHCH$_2$CH$_2$CH$_2$), 1.44-1.32 (2H, m, CHCH$_2$CH$_2$CH$_2$) $^{13}$C-NMR (125 MHz, CD$_3$OD): δ ppm 175.5 173.7 170.0 169.3 145.5 141.3 138.4 134.5 130.0 129.1 129.0 128.6 128.1 128.0 101.4 74.5 72.5 71.5 69.4 63.8 54.1 44.7 42.5 41.0 32.0 31.3 29.4 22.7; HRMS-ESI (m/z): calcd for C88H117N9Na2O28S3 (M−2Na+H) 1844.7254 found 1844.7362.

Compound 36

15 mg of compound 28 and 10 mg of doxorubicin were dissolved in 2 ml of abs. MeOH and the mixture was stirred for 17 h. The solution was concentrated and purified on silica gel (eluent EtOH:dioxane:NH$_4$OH 25% 1:4:1, then 1:2:1). Yield: 12 mg; $R_f$ 0.50 (1-butanol:HAc100%:H$_2$O 5:2:3); HRMS-ESI (m/z): calcd for C109H136N10Na2O38S2 (M−2Na) 865.8417 found 865.8408.

Compound 37

11 mg of compound 15 and 7.9 mg of N-succinylcolchicine were dissolved in 1 ml of abs. DMF, 3.77 mg of HATU and 6.8 μl of DIPEA were added and the mixture concentrated after 10 min. The reaction mixture was purified on RP18 and the product saponified analogously to compound 12.

DC-RF: 0.22 (1:3:1 EtOH:EE:HAc20%); HRMS-ESI (m/z): calcd for C102H128N8Na2O33S2 (M−2Na) 1028.4018 found 1028.4022.

N-(7-Carboxy-5,4-dithiaheptanyol)colchicine Sodium Salt 44.6 mg of 3,3'-dithiodipropionic acid in 1 ml of abs. DMF were treated with 8.9 mg of HATU and 14.5 μl of DIPEA and, after 10 s, 10 mg of deacetyl colchicine were added, the reaction mixture concentrated and the residue purified on silica gel (EtOH:EE:HAc20% 1:8:1). The residue was dissolved in dil. NaHCO$_3$ and freed from 3,3'-dithiodipropionic acid residues on RP18.

Compound 38

8.6 mg of N-(7-carboxy-5,4-dithiaheptanyol)colchicine sodium salt in 1 ml of abs. DMF were treated with 3.4 mg of HATU and 4.6 μl of DIPEA and, after 10 s, 10 mg of compound 16 in 0.5 ml of abs. DMF were added, the mixture concentrated and purified on RP18. DC-RF: 0.72 (EtOH: dioxane:NH$_4$OH25%); HRMS-ESI (m/z): calcd for C104H132N8Na2O33S4 (M−2Na) 1074.3895 found 1074.3908.

Compound 39

15 mg of compound 28 and 9.5 mg of 2-(4-acetylphenoxy)-N-acetamidocolchicine were dissolved in 1 ml of abs. MeOH. After 24 h, the mixture was concentrated and purified on silica gel (EtOH:dioxane:NH$_4$OH25%). DC-RF: 0.69 ((EtOH:dioxane:NH$_4$OH25%); HRMS-ESI (m/z): calcd for C112H138N10Na2O35S2 (M−2Na) 1123.4389 found 1123.4375.

The structures of the low molecular weight conjugates are listed in Table X.

TABLE X

| No. | Structure |
|---|---|
| 35 | 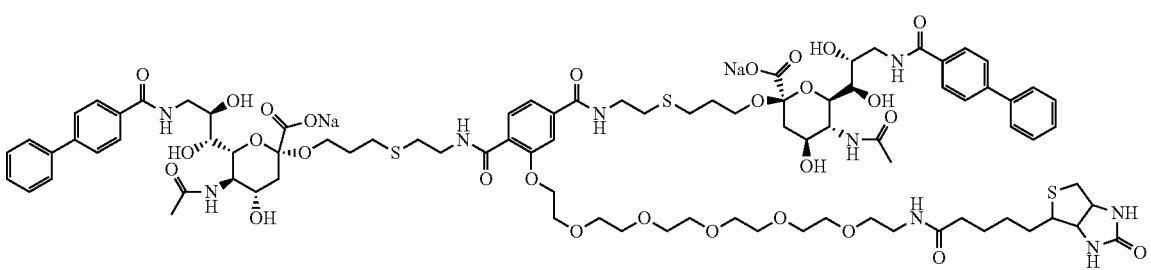 |
| 36 | 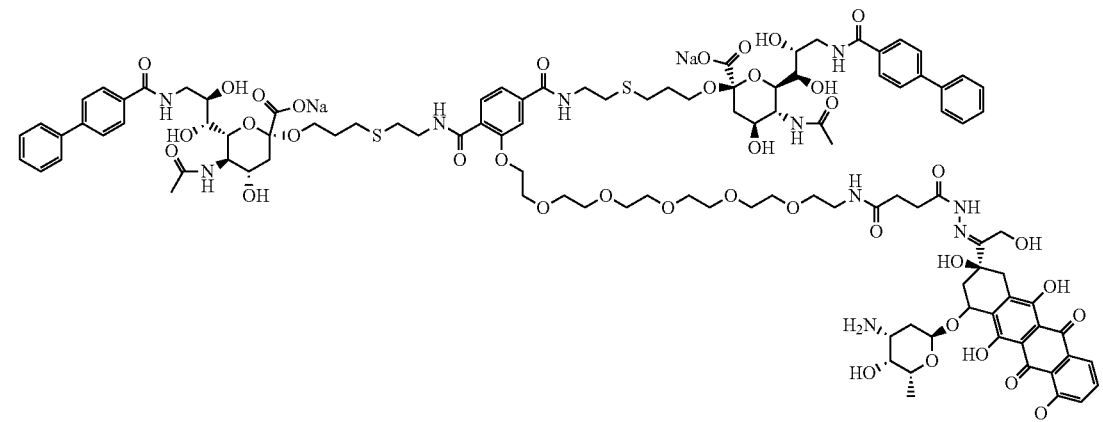 |
| 37 | 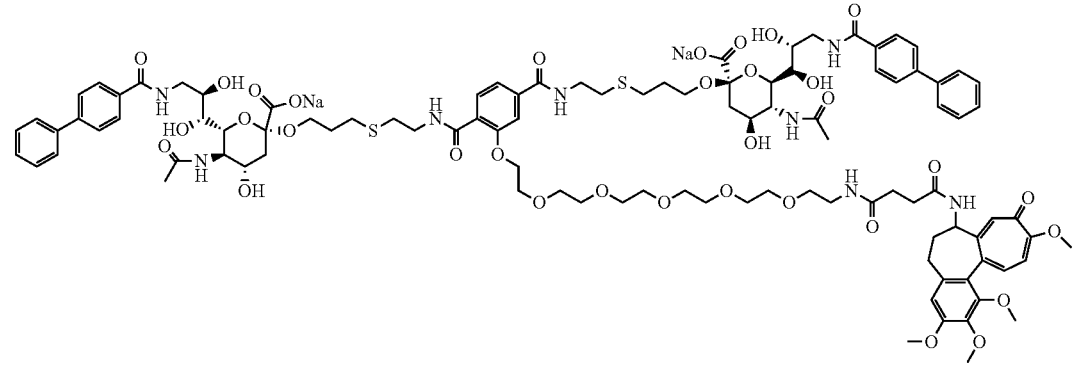 |

| No. | Structure |
|---|---|
| 38 | 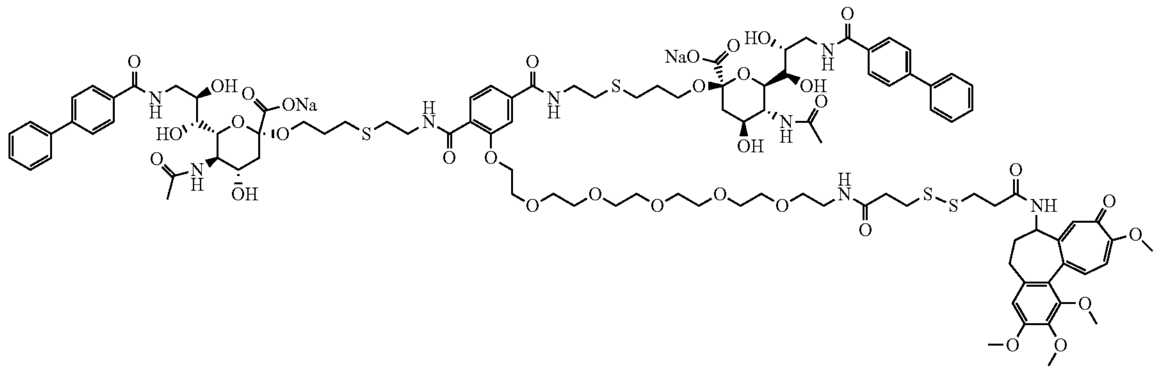 |
| 39 | 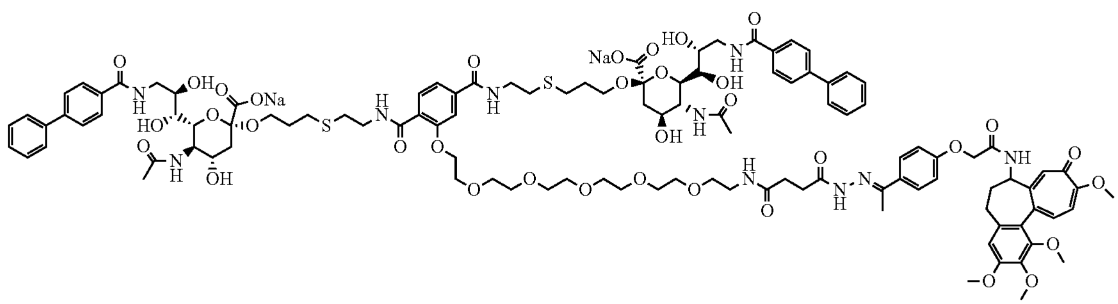 |
Preparation of Protein Conjugates
Preparation of a Conjugate with Albumin (Compound 40)
500 µg of albumin were dissolved in 200 µl of 1 mM phosphate buffer pH 8. 24 h after addition of 1.2 mg of compound 26, the mixture was dialyzed.
Preparation of Polymeric Conjugates
Examples are presented in Schemes 7 and 8.
Scheme 7
Compound 41
↓
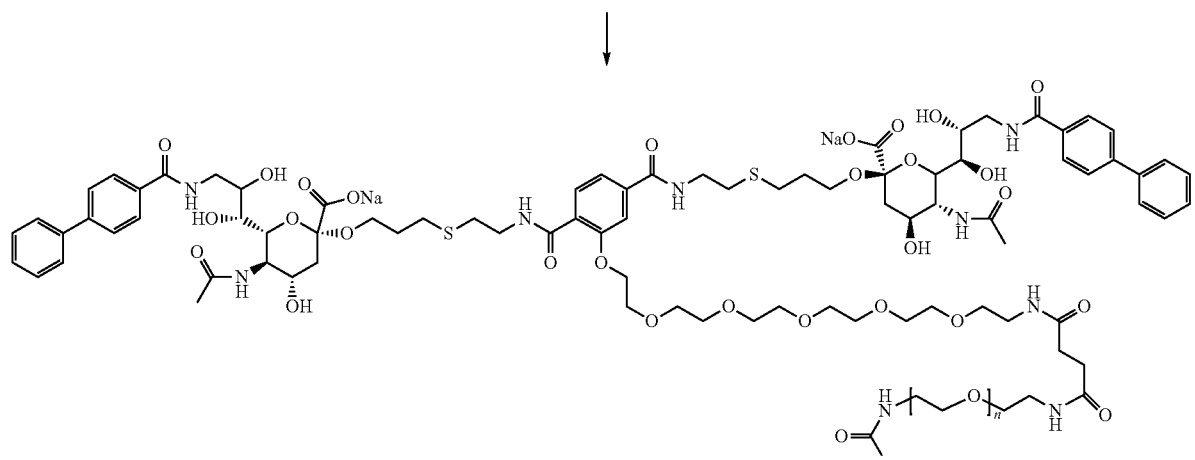

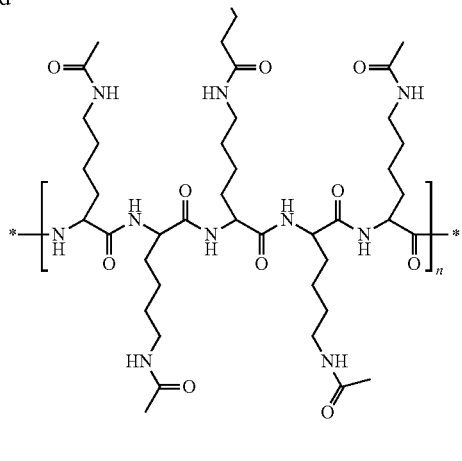

42
n = 35-51

Scheme 8

Compound 41

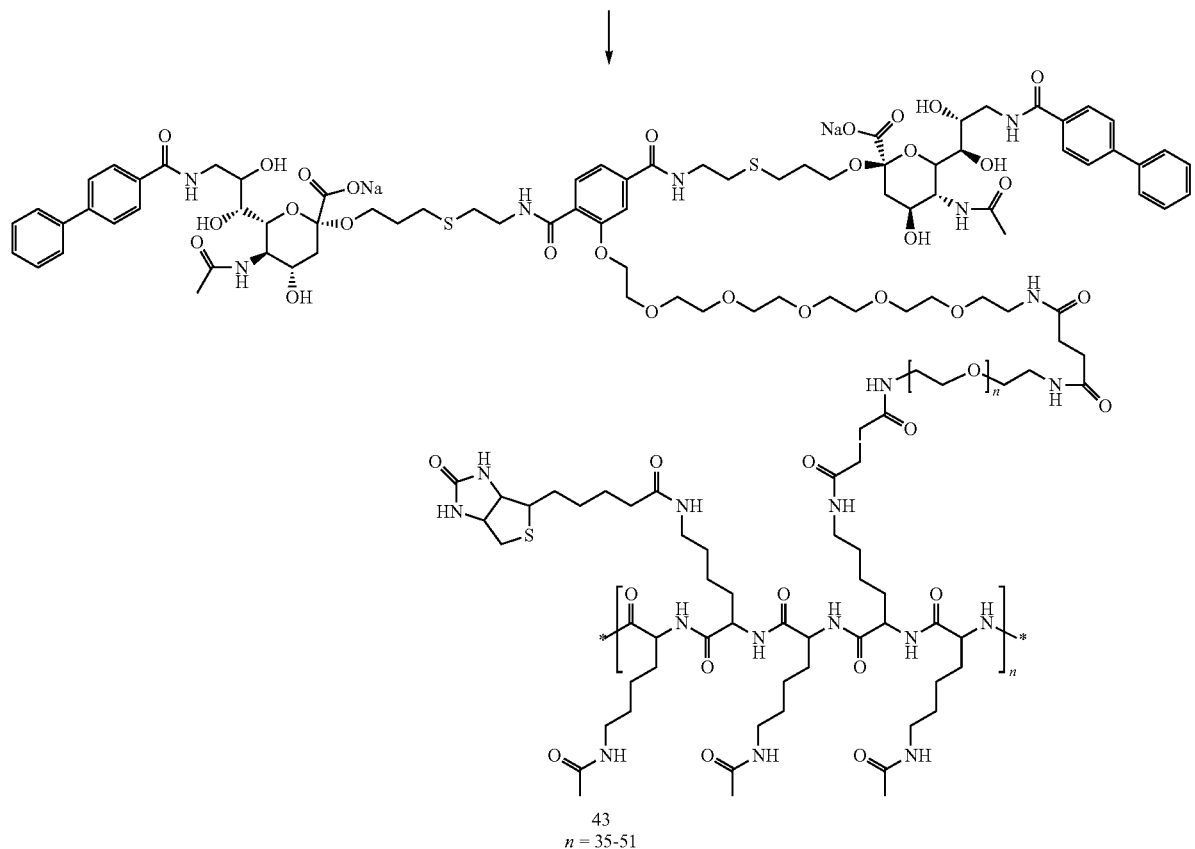

43
n = 35-51

Compound 42

22 mg of compound 41 were dissolved in 1 ml of abs. DMF, 2.52 mg of HATU and 3.1 µl of DIPEA were added and the solution was added directly to a solution of 4.8 mg of poly-L-lysine hydrobromide (MW 300-5000) and 0.1 ml of TEA in 0.5 ml of DMSO. After 5 min, 12.5 mg of acetic anhydride were added. After a further 30 min, the solvent was removed, the residue dissolved in an ethanol-water mixture and adjusted to pH 12-13 with 2M NaOH. After 17 h, the solution was neutralized with dil. HCl to pH 7-8 and lyophilized Water was added to the residue which was filtered through cotton wool, purified from salts on Sephadex G25 and lyophilized Yield 11 mg (41%)

Compound 43

8 mg of compound 41 were dissolved in 0.25 ml of abs. DMF, 0.46 mg of HATU and 1.26 µl of DIPEA were added and the solution was added directly to a solution of 2.3 mg of poly-L-lysine hydrobromide (MW 300-5000) and 0.05 ml of TEA in 0.5 ml of DMSO. 0.52 mg of biotin in 0.5 ml of abs. DMF was treated with 0.90 mg of HATU and 2.2 µl of DIPEA and added to the solution. After 5 min, 12.5 mg of acetic anhydride were added. After a further 30 min, the mixture was diluted with water and adjusted to pH 12-13 with 2 M of NaOH. After 17 h, the solution was neutralized with dil. HAc to pH 7-8 and purified from salts on Sephadex G25 and lyophilized Yield 7 mg (70%).

Biological Tests

In order to be able to determine the affinity of the novel derivatives to CD22, a new assay was developed. For this assay, compound 35 (conjugate of a sialic acid derivative of the formula (I) and biotin) was prepared.

with Streptavidin-PE in the dark, then washed and the amount of substance 35 bound via Streptavadin-PE was measured by FACS. For the determination of 0% displacement of substance 35, cells without inhibitor were measured. For the determination of 100% displacement, cells were measured without substance 35 and without inhibitor. 4 substances and one reference substance were measured per assay. The IC50 values determined in each assay were subsequently converted into rIP values. For this purpose, substance 46 served as reference.

The literature shows, in comparison to the momomers "BPC-Neu5Ac" (J. Exp. Med. 2002, 195, 1207-1213), two ligands "BPC-NeuAc-LN" and "BPA-NeuGc-LN", which have a reactive group for coupling to a cargo or a carrier (J. of Immunology 2006, 177, 2994-3003). A direct comparison of the known substances with the compounds of the formula (I) was not possible since the IC50 values of the two substance classes behave independently from assay to assay.

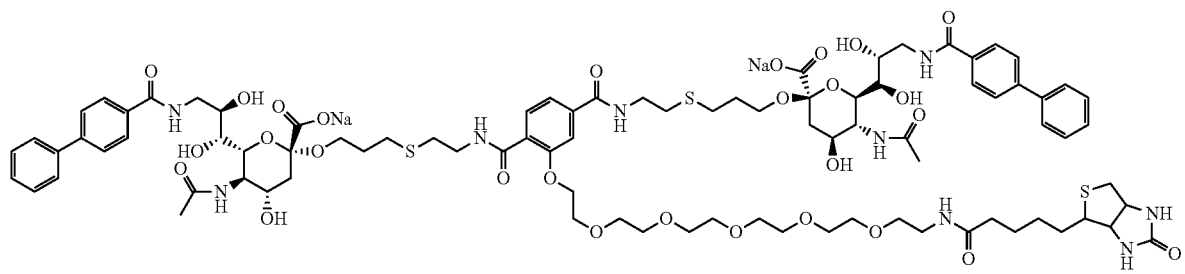

35

To determine the affinity of the compound of the formula (I), approximately $2\times10^8$ cells of the human B cell lymphoma line "Daudi" were incubated with sialidase (*A. ureafaciens*) for 1 h at 37° C. Subsequently, the enzyme was blocked with 1.5 mM 2,3-dehydroNeu5Ac and the cells were washed twice with PBS. Batches of $1\text{-}2\times10^6$ cells were transferred to sample vials and incubated on ice for 15 min with serial concentrations (10-fold dilutions) of the substance to be measured (inhibitor) and then for 20 min with 2 µmolar substance 35. The reaction volume was 50 µl. After washing with PBS, the sample was incubated for 15 min The reason for the different behaviour of the two substance classes lies in the different properties, particularly the valency. A reference substance with the same valency was therefore introduced; the IC50 values for the compounds fluctuated from assay to assay, but it was possible to form stable rIP values. Table II shows the affinities of the reference compounds 45, 46 and also of the compounds BPC-Neu5Ac, BPC-NeuAc-LN, BPA-NeuGc-LN and of a sialic acid derivative of the formula (I) (compound 16) to CD22 (Siglec-2).

TABLE II

| | Structure | rIP (Literature assay) | rIP (New assay) |
|---|---|---|---|
| BPC NeuAc | 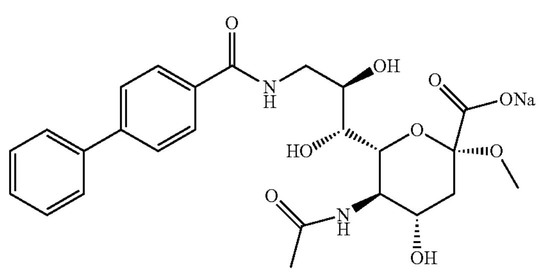 | 1 | 1 |

TABLE II-continued

| | Structure | rIP (Literature assay) | rIP (New assay) |
|---|---|---|---|
| BPC NeuAc-LN | [structure] | 15.9 | — |
| BPA NeuGc-LN | [structure] | 15.9 | — |
| 45 | [structure] | — | ~1-3 |
| 46 | [structure] | — | >2000 |
| 16 | [structure] | — | >1000 |

The rIP values of all sialic acid derivatives of the formula (I), for which the affinity could be determined, are shown in Table III. Affinity was not determined for some sialic acid derivatives of the formula (I) since groups essential for the affinity are not deprotected until after the reaction with a cargo. The values are relative to compound 45.

TABLE III

| No. | rIP |
|---|---|
| 45 | 1 |
| 34 | 953 |

TABLE III-continued

| No. | rIP |
| --- | --- |
| 29 | 327 |
| 12 | 244 |
| 16 | 774 |
| 33 | 500 |
| 21 | 780 |
| 22 | 1847 |
| 25 | 864 |

The rIP values of some conjugates of sialic acid derivatives of the formula (I) and a carrier molecule are described in Table (V). The values are relative to compound 45.

TABLE V

| No. | rIP |
| --- | --- |
| 45 | 1 |
| 40 | $4.5 \times 10^5$ |
| 42 | $2.1 \times 10^6$ |

The sialic acid derivatives of the formula (I) may be coupled to a polymeric carrier and may transport a cargo, coupled to this carrier, into cells expressing CD22. The conjugate 43, for example, was prepared with polylysine as polymeric carrier and biotin as cargo.

The CD22 positive cell line Nalm-6 and the CD22 negative cell line HL-60 were harvested and incubated with compound 43 for 1 h at 0° C. The cells were subsequently washed and the cells suspended in RPMI medium with 10% FCS at 37° C. At various time points, cells were removed and washed with a low pH buffer (0.2M glycine HCl, pH 2.4), in order to remove residues on the cell surface-bound conjugate. After fixing with paraformaldehyde, the cells were permeabilized with 70% MeOH. After washing twice with FACS buffer, the internalized conjugate was stained with streptavidin phycoerythrin and determined by FACS.

An uptake of compound 43 in CD22 positive cells was noted while in the CD22 negative cell line no compound was taken up.

The invention claimed is:

1. Sialic acid derivative of the formula (I),

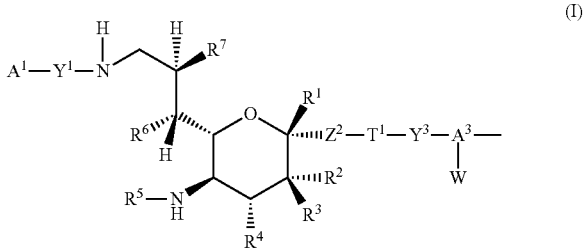

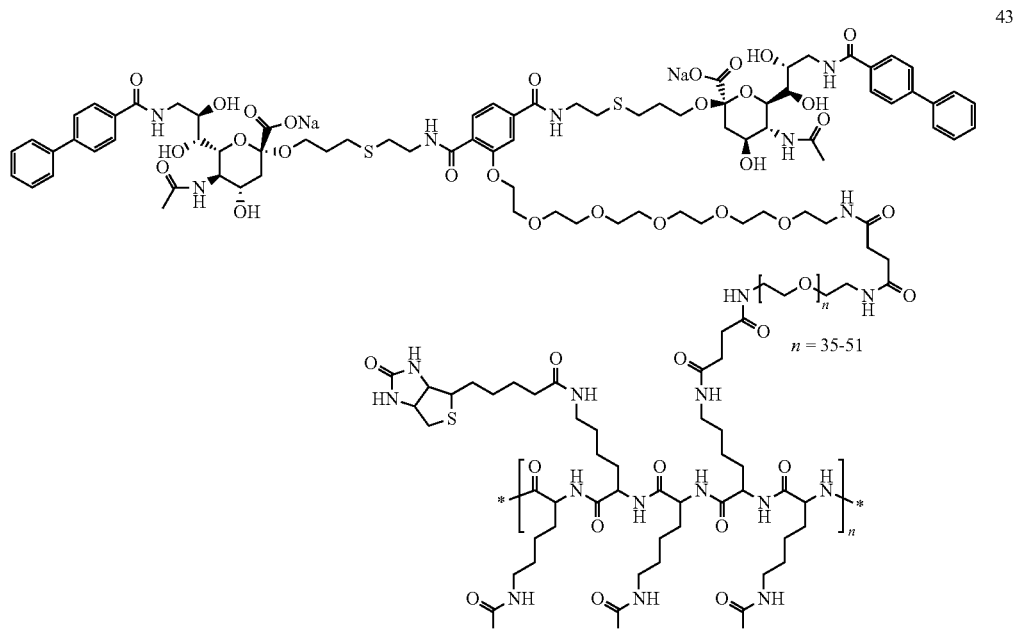

43

-continued

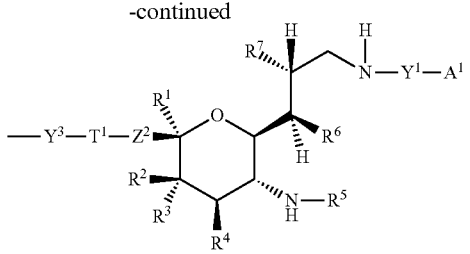

where the symbols are defined as follows:

$A^1$ is equal to 4-biphenyl, 4-(2-thienyl)benzoyl, 4-(3-thienyl)benzoyl, 1-naphthyl and 2-naphthyl, in which the residues mentioned are unsubstituted or mono- or polysubstituted by a group $X^1$;

$X^1$ is identically or differently fluorine, chlorine, hydroxyl, carboxy, $SO_3M$, $OSO_3M$, $SO_2NH_2$, $SO_2CF_3$, alkyl, cycloalkyl, haloalkyl, alkyloxy, haloalkyloxy, alkylcarbonyloxy, alkylcyclocarbonyloxy, aminocarbonyl, alkylaminocarbonyl, cycloalkylaminocarbonyl, alkylcarbonylamino, cycloalkylcarbonylamino, alkylamino, cycloalkylamino, dialkylamino, dicycloalkylamino or alkylcycloalkylamino, in which the alkyl groups in these residues comprise 1 to 4, and the cycloalkyl groups 3 or 4, carbon atoms;

$Y^1$ is equal to ~($C_1$-$C_2$-alkyl)-, ~C(O)— or ~$CH_2$C(O)—, in which ~ denotes the bond to the group $A^1$;

$Z^2$ is equal to —O—, —S— or —$CH_2$—;

$T^1$ is equal to a straight-chain or branched alkanediyl group having 3 to 10 C atoms, in which
  (i) optionally one or more non-terminal $CH_2$ groups are replaced by —O— and/or —S— and/or
  (iv) optionally one or more H atoms are replaced by F and/or Cl and/or
  (v) optionally one non-terminal —$CH_2CH_2$— group is replaced by —NHCO—;

$Y^3$ is equal to —C(O)—, ~C(O)—NH— or ~NH—C(O)—, in which ~ denotes the bond to group $A^3$;

$A^3$ is
  a) a $C_1$-$C_8$-alkanetriyl, in which optionally more than one non-terminal $CH_2$ groups are replaced by O, S, S(O), $S(O)_2$, $NR^x$ and/or C(O) and wherein optionally one or more H atoms in the groups mentioned are replaced by a group $X^2$,
  b) a saturated, partially unsaturated or aromatic, mono- or polycyclic hydrocarbon residue having 3 to 14 C atoms or one three- to eight-membered, aromatic, partially unsaturated or saturated mono- or polycyclic heterocyclic residue, in which the groups mentioned are optionally substituted in each case by one or more groups $X^2$,
  c) a tertiary nitrogen;

$X^2$ is equal to fluorine, chlorine, alkyl, haloalkyl or alkyloxy, in which the alkyl groups in these residues comprise 1 to 2 carbon atoms;

W is —$Y^5$-$T^2$-V or —V;

V is ~C(O)O-4-nitrophenyl, ~C(O)O-pentafluorophenyl, maleic-2-yl anhydride, ~C(O)-1-azetidin-2-one, ~4-O-phenyl-C(O)-1-azetidin-2-one, ~N=C=O, ~N=S=O, ~C(O)$N_2$, ~$S(O)_2$Cl, ~C($NH_2$)$OR^y$, ~P($CH_2OH$)$_3$, ~SH, ~SC(O)$CH_3$, ~$NH_2$, ~OH, ~CH=$CH_2$, ~C≡CH, ~COOM, ~C(O)H, ~C(O)$CH_3$, ~C(O)C(O)H, ~I, ~$N_3$, ethyl-2-(3-indol)amine-1~, ~$S(O)_2N_3$, phenyl-CH=CH—C($N_2$)—C(O)O~, ~CH=CHCH$_2$OC(O)$R^y$, ~CH=CHCH$_2$OC(O)NH$R^y$, ~OC(O)$OR^y$, ~C(O)NHNH$_2$, ~N-maleimide, aziridine-2~, pyridine-2-S—S~, phenyl-1-carboxy-2-nitro-5-S—S~, ~$S(O)_2$CH=$CH_2$, ~C(O)—S-phenyl, ~C(O)CH=$N_2$, ~C(O)O—N-succinimidyl, or C(O)O—N-sulphosuccinimidyl;

$Y^5$ is a bond, —O—, —S—, —$NR^x$—, —C(O)—, ~C(O)—$NR^x$— or ~$NR^x$—C(O)—, in which ~ denotes the bond to group $A^3$;

$T^2$ is a straight-chain or branched alkanediyl group having 1 to 200 C atoms, in which
  (i) optionally one or more non-terminal $CH_2$ groups are replaced by —O—, NH and/or —S— and/or
  (iv) optionally one or more non-terminal H atoms are replaced by F, Cl, (=O), $NR^z$ and/or $NR^y$ and/or
  (v) optionally one or more non-terminal —$CH_2CH_2$— group is replaced by —NHCO— or —S—S—;

$R^1$ is equal to C(O)OM;

$R^2$, $R^3$ are equal to H;

$R^4$, $R^6$, $R^7$ are identically or differently OH or $OR^z$;

$R^5$ is equal to C(O)$CH_3$ or C(O)$CH_2$OH;

M is equal to a $C_1$-$C_4$-alkyl, $C_3$-$C_4$-cycloalkyl or a cation;

$R^x$ is identically or differently H, $R^y$ or $R^z$;

$R^y$ is identically or differently $C_1$-$C_4$-alkyl, $C_3$-$C_4$-cycloalkyl, phenyl or benzyl and $R^z$ is identically or differently —C(O)—$C_1$-$C_4$-alkyl, —C(O)—$C_3$-$C_4$-cycloalkyl, —C(O)-phenyl or C(O)—$CH_2$-phenyl.

2. Sialic acid derivative of the formula (I) according to claim 1, where the symbols in the formula (I) are defined as follows:

$A^1$ is equal to a group 4-biphenyl, 1-naphthyl and 2-naphthyl, in which the groups mentioned are unsubstituted or are substituted by one or more groups $X^1$;

$X^1$ is identically or differently fluorine, chlorine, hydroxyl, alkyl, haloalkyl, alkyloxy, haloalkyloxy, alkylcarbonyloxy, in which the alkyl groups in these residues comprise 1 to 2 carbon atoms;

$Y^1$ is equal to —C(O)— or ~$CH_2$C(O)—, in which ~ denotes the bond to group $A^1$;

$Z^2$ is equal to —O—;

$T^1$ is equal to a straight-chain or branched alkanediyl group having 4 to 8 C atoms, in which
  (i) optionally one or more non-terminal $CH_2$ groups are replaced by —O— and/or —S— and/or
  (ii) optionally one non-terminal —$CH_2CH_2$— group is replaced by —NHCO—;

$Y^3$ is equal to a bond, ~C(O)—NH— or ~NH—C(O)—, in which ~ denotes the bond to group $A^3$;

$A^3$ is a
  a) $C_1$-$C_5$-alkanetriyl, in which optionally one or more non-terminal $CH_2$ groups are replaced by O, S, $NR^x$ and/or C(O) and wherein optionally one or more H atoms in the groups mentioned are replaced by a group $X^2$,
  b) phenylene-1,2,4-triyl or 1H(1,2,3)triazole-1,4,5-triyl, in which the groups mentioned are in each case optionally substituted by one or more groups $X^2$,
  c) tertiary nitrogen;

$X^2$ is equal to fluorine, chlorine, methyl, methyloxy;

W is —$Y^5$-$T^2$-V or —V;

V is ~C(O)O-4-nitrophenyl, ~C(O)O-pentafluorophenyl, maleic-2-yl anhydride, ~N=C=O, ~N=S=O, ~C(O)$N_2$, ~P($CH_2OH$)$_3$, ~SH, ~$NH_2$, ~OH, ~CH=$CH_2$, ~C≡CH, ~COOM, ~C(O)H, ~C(O)$CH_3$, ~C(O)C(O)H, ~I, ~$N_3$, ~C(O)NHNH$_2$, ~N-maleimide, aziridine-2~, pyridine-2-S—S~, phenyl-1-carboxy-2-nitro-5-S—S~, ~C(O)O—N-succinimidyl;

$Y^5$ is a bond, —O—, —NH—, —C(O)—, ~C(O)—NH— or ~NH—C(O)—, in which ~ denotes the bond to group $A^3$;

$T^2$ is a straight-chain or branched alkanediyl group having 1 to 200 C atoms, in which
  (i) optionally one or more non-terminal $CH_2$ groups are replaced by —O— or —NH— and/or
  (ii) optionally one or more non-terminal H atoms are replaced by F or (=O) and/or
  (iii) optionally one or more non-terminal —$CH_2CH_2$— group is replaced by —NHCO— or —S—S—;

R[1] is equal to C(O)OM;
R[2], R[3] are equal to H;
R[4], R[6], R[7] are identically or differently OH or OR[z];
R[5] is equal to C(O)CH$_3$;
M is equal to a C$_1$-C$_2$-alkyl or a cation;
R[x] is identically or differently H, R[y] or R[z];
R[y] is identically or differently C$_1$-C$_3$-alkyl, cyclopropyl, phenyl or benzyl and
R[z] is identically or differently —C(O)—C$_1$-C$_4$-alkyl, —C(O)-phenyl or —C(O)—CH$_2$-phenyl.

3. Sialic acid derivative according to claim 1, where the symbols in the formula (I) are defined as follows:
A[1] is equal to 4-biphenyl, in which the group mentioned is unsubstituted or is substituted by one or more hydroxyl groups;
Y[1] is equal to —C(O)—, in which ~ denotes the bond to group A[1];
Z[2] is equal to —O—;
T[1] is equal to hexane-1,6-diyl, in which optionally one non-terminal CH$_2$ group is replaced by —S—;
Y[3] is equal to —C(O)—NH—, in which ~ denotes the bond to group A[3];
A[3] is propane-1,1,3-triyl or phenyl-1,2,4-triyl;
W is —Y[5]-T[2]-V or —V;
V is ~SH, ~NH$_2$, ~CH=CH$_2$, ~C≡CH, ~COOM, ~I, ~N$_3$, ~C(O)NHNH$_2$, ~N-maleimide, ~C(O)O—N-succinimidyl;
Y[5] is a bond, —O— or ~NHCO—, in which ~ denotes the bond to group A[3];
T[2] is a straight-chain or branched alkanediyl group having 1 to 200 C atoms, in which
  (i) optionally one or more non-terminal CH$_2$ groups are replaced by ~O— and/or
  (ii) optionally one or more non-terminal —CH$_2$CH$_2$— groups are replaced by —NHCO— or —S—S—;
R[1] is equal to C(O)OM;
R[2], R[3] are equal to H;
R[4], R[6], R[7] are equal to OH or OC(O)CH$_3$;
R[5] is equal to C(O)CH$_3$;
M is CH$_3$ or sodium.

4. Sialic acid derivative of the formula (I) according to claim 1 having the formula (Ia) or (Ib), in which the symbols are as defined in the formula (I):

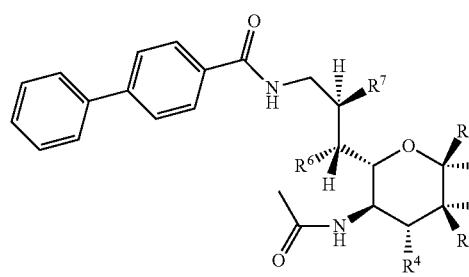
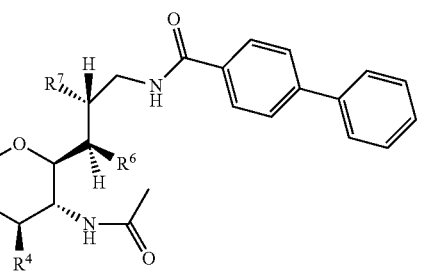

Ia

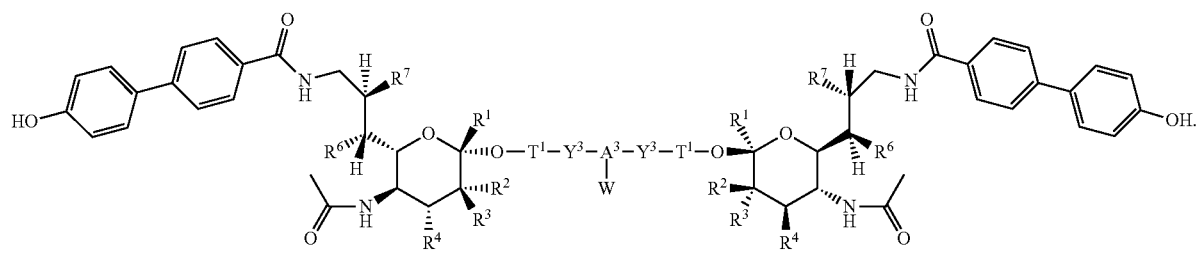

Ib

5. Sialic acid derivative of the formula (I) according to claim 1, selected from the group consisting of:

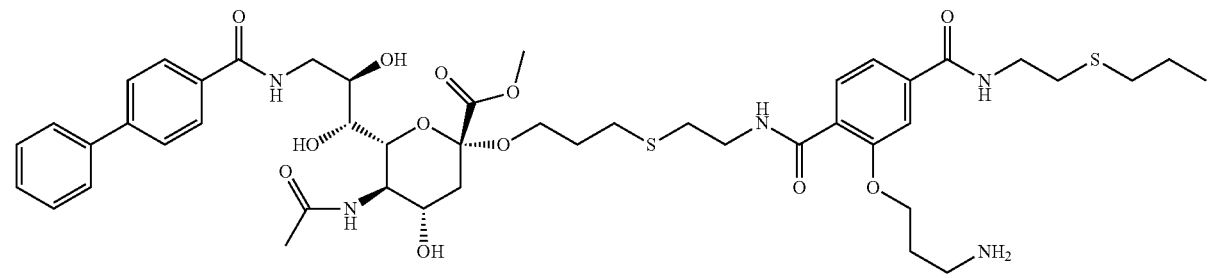

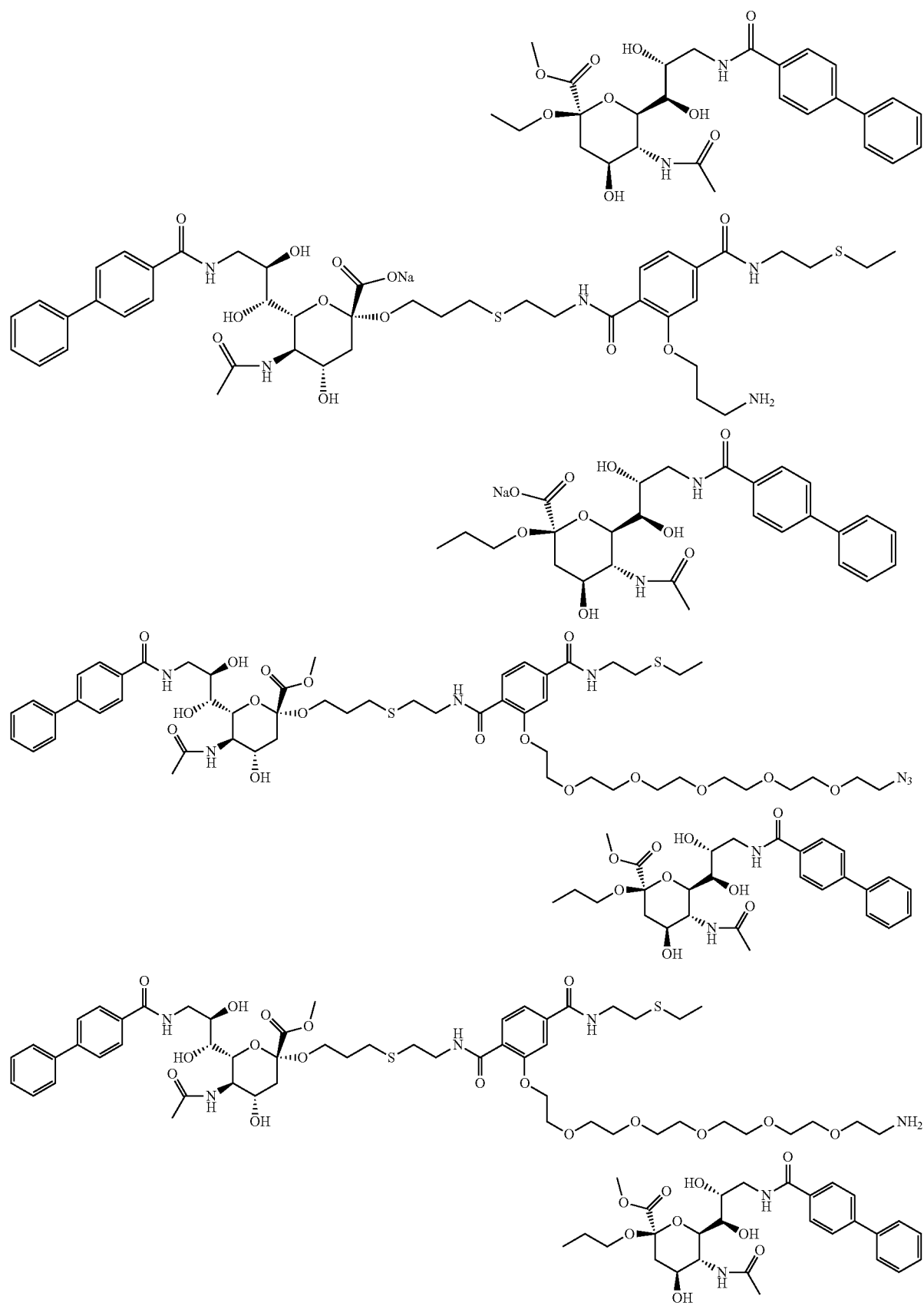

71
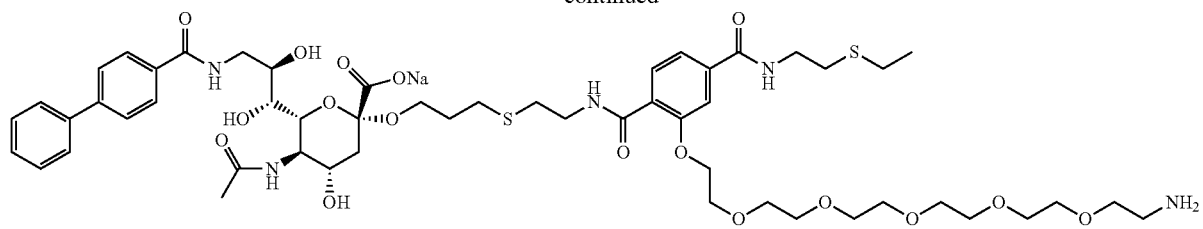
72
-continued
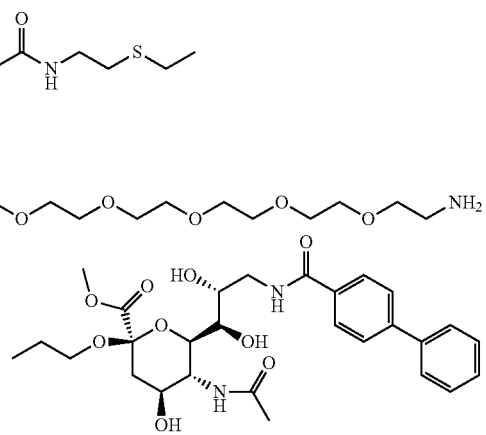
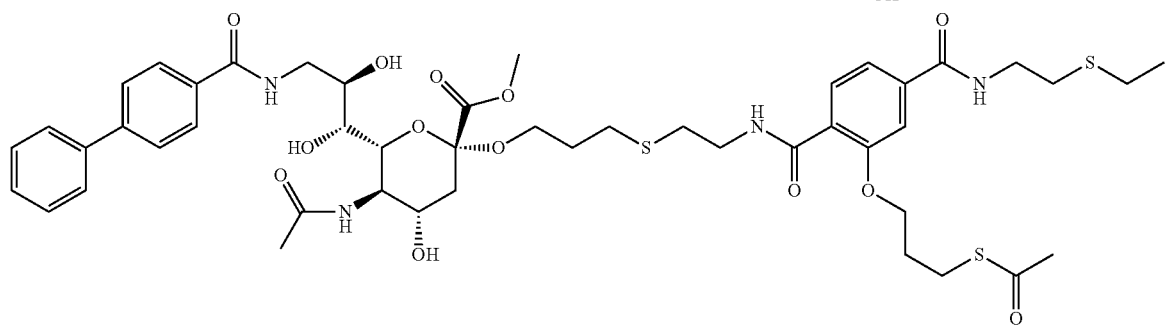
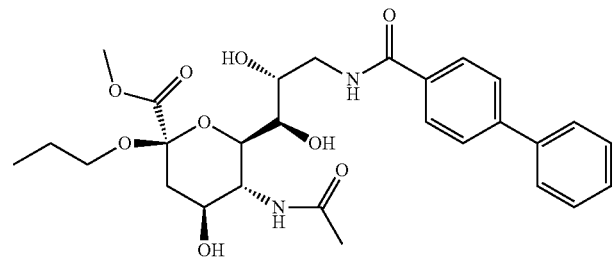
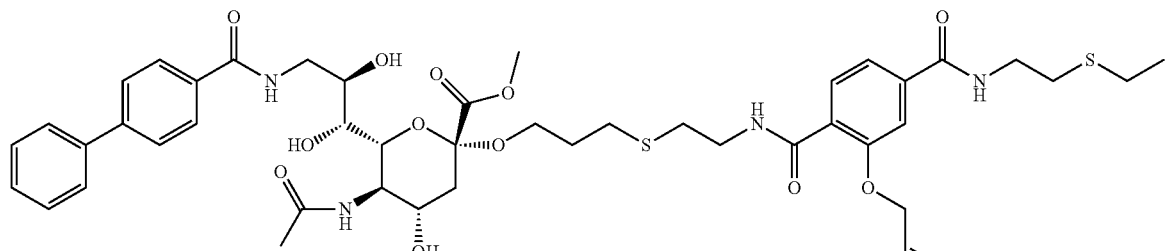
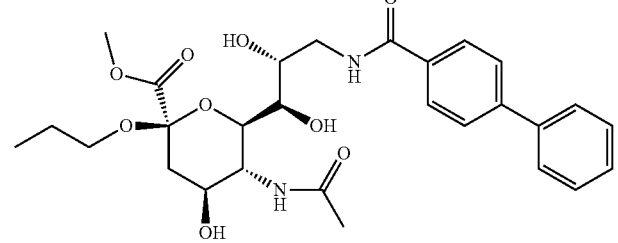

73
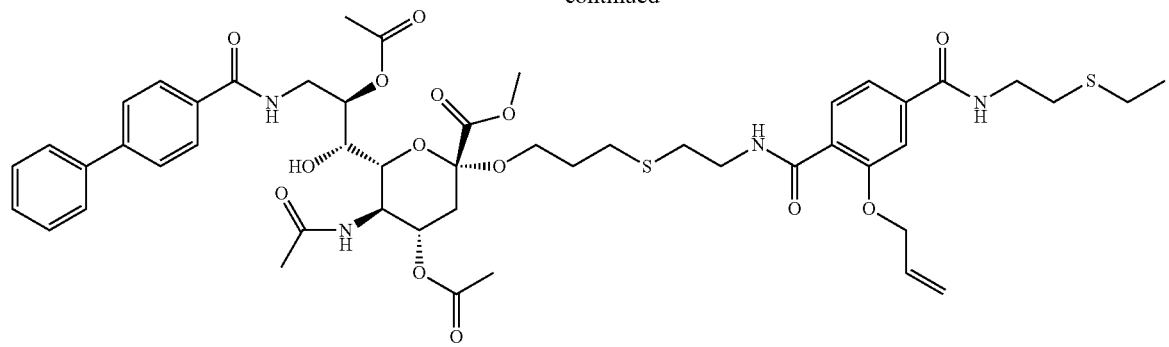
74
-continued
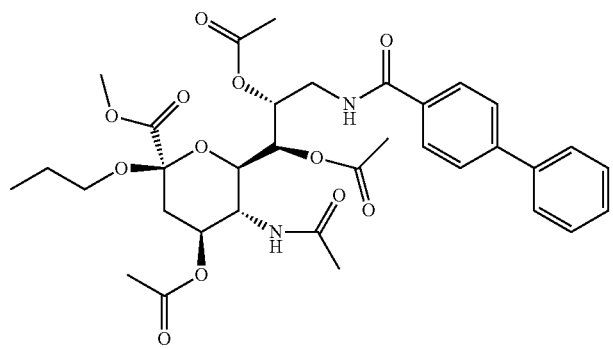
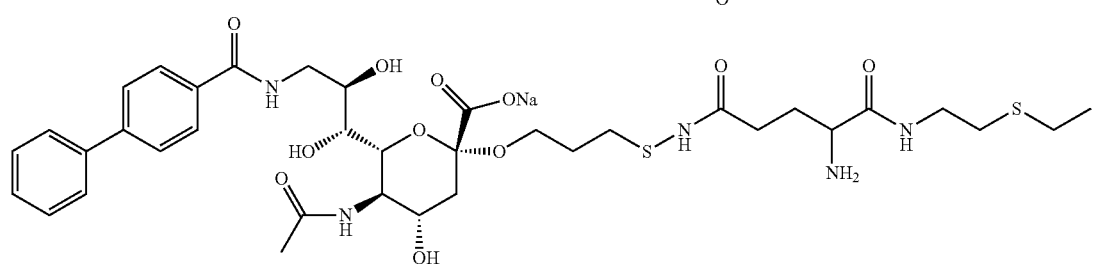
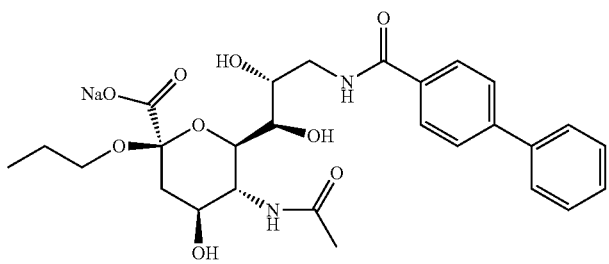
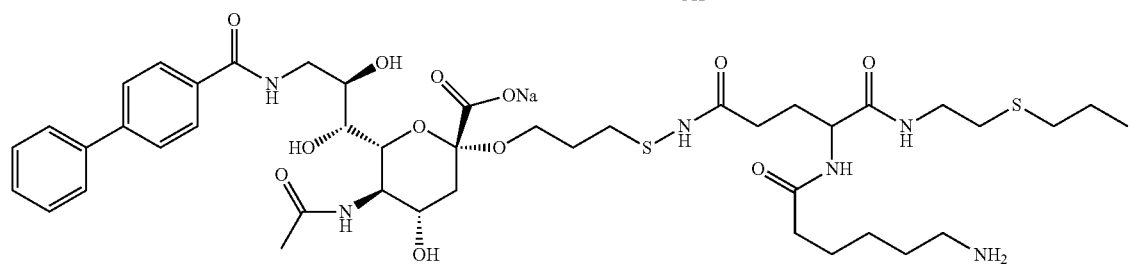
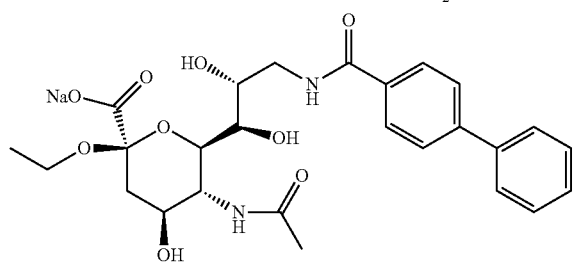

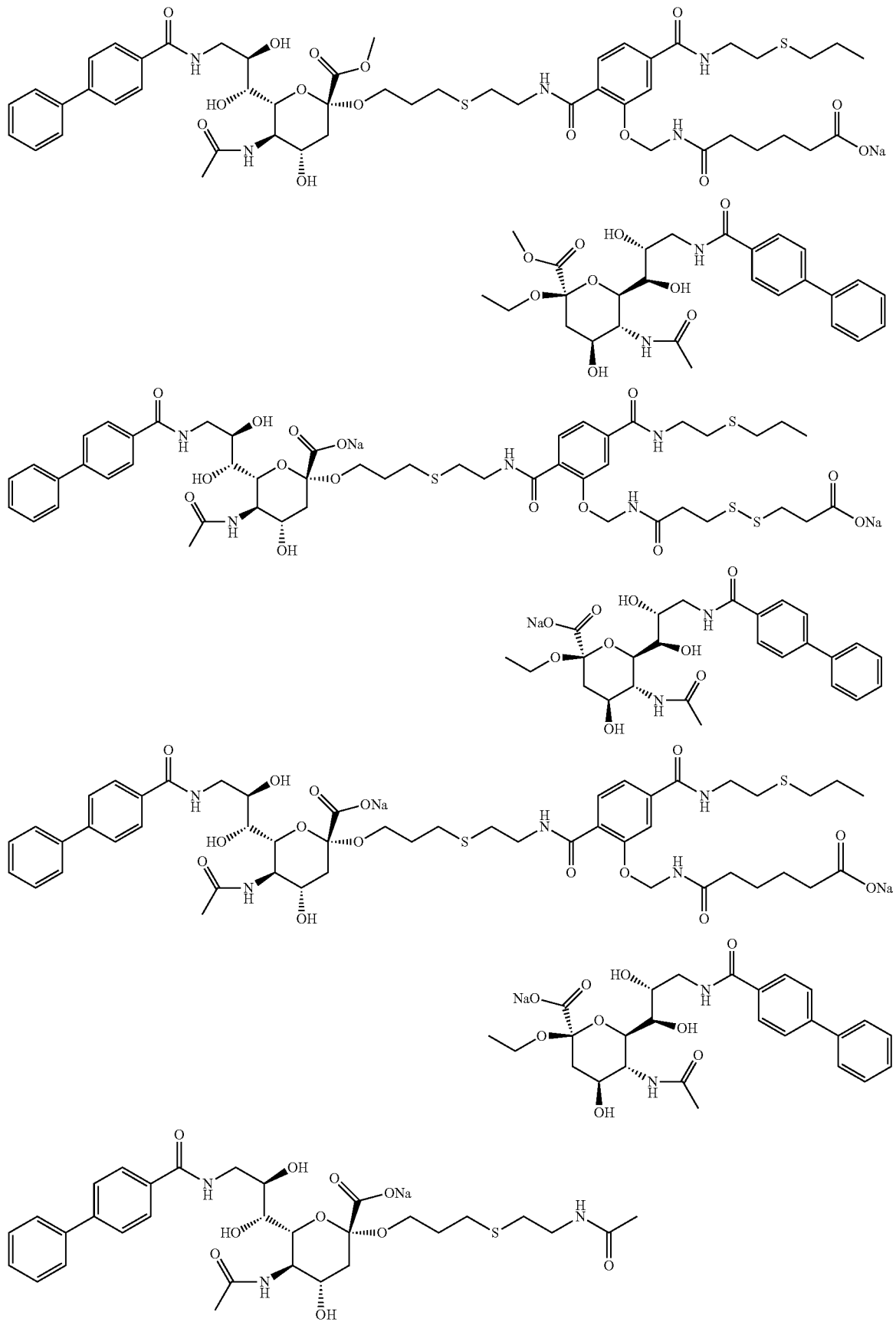

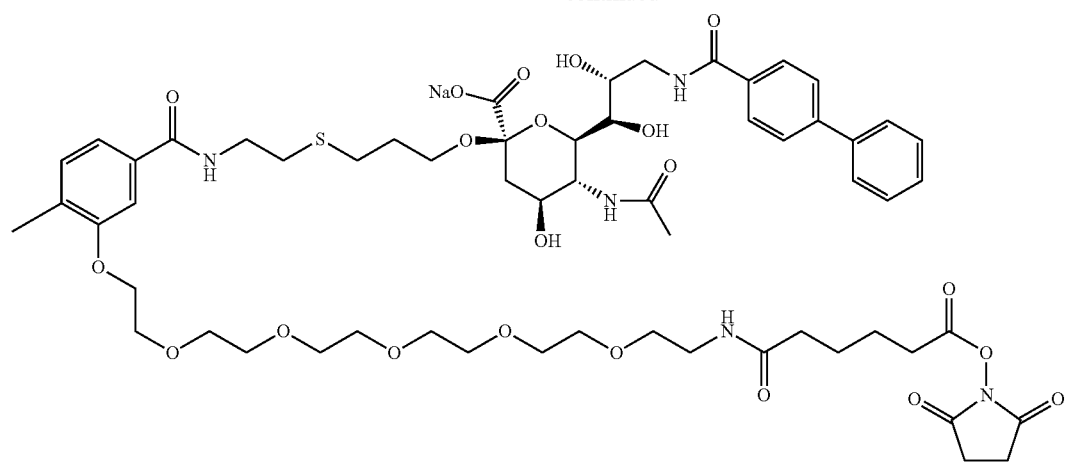
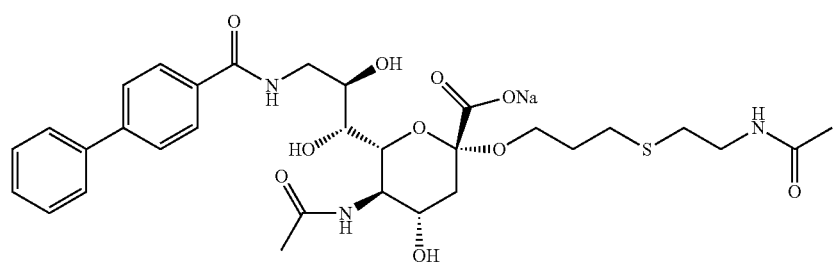
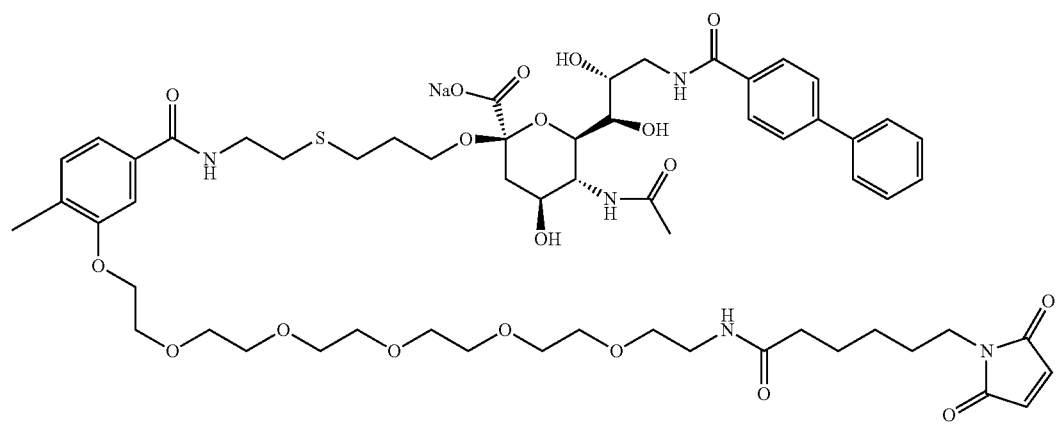
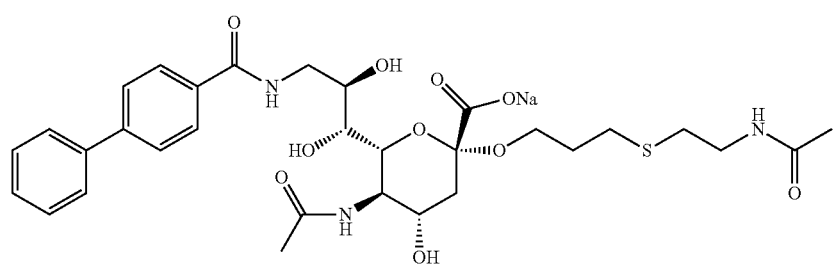

-continued
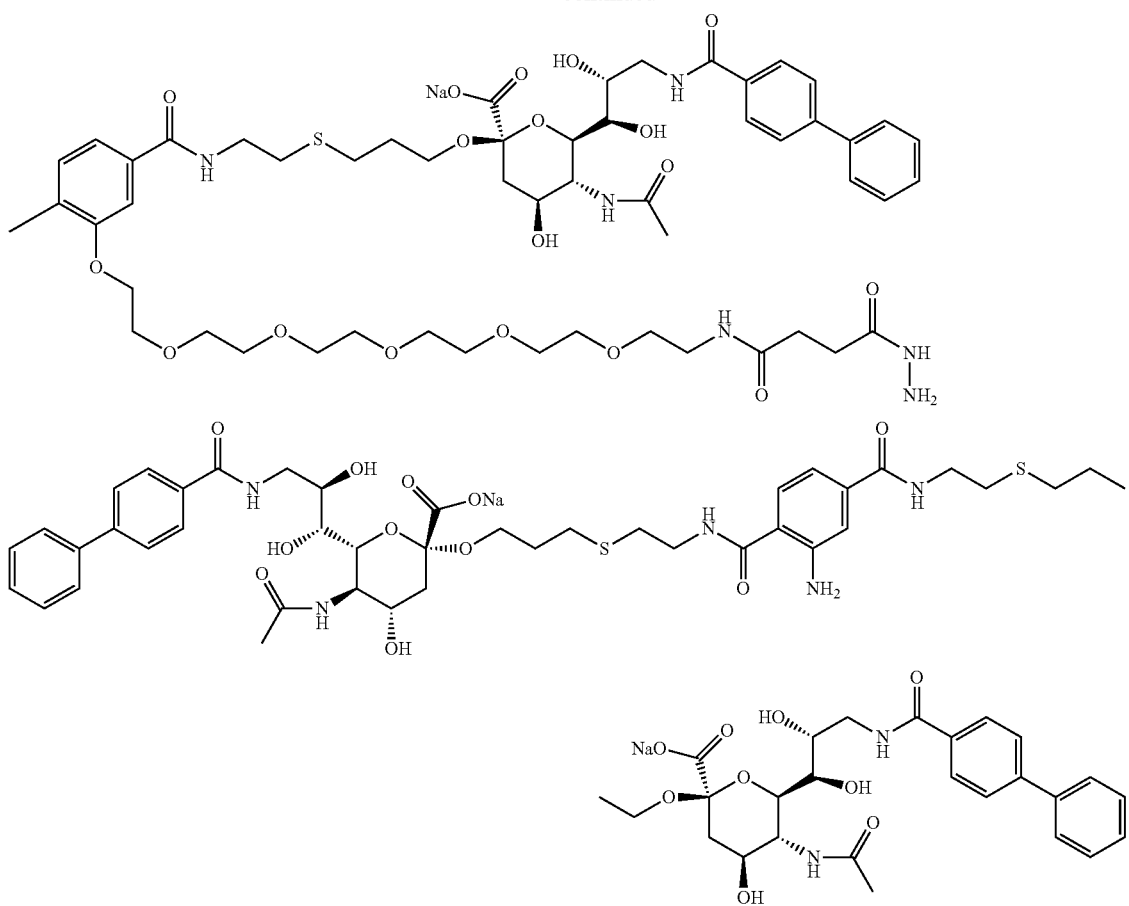
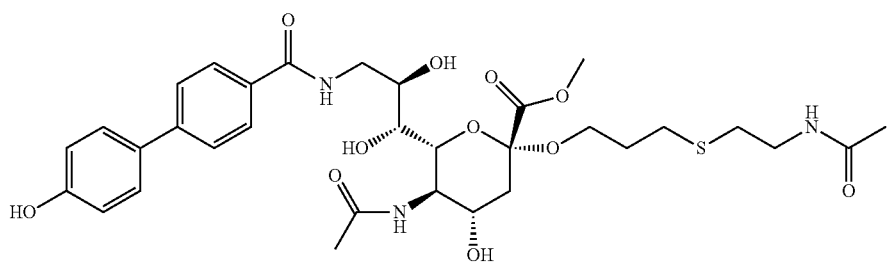
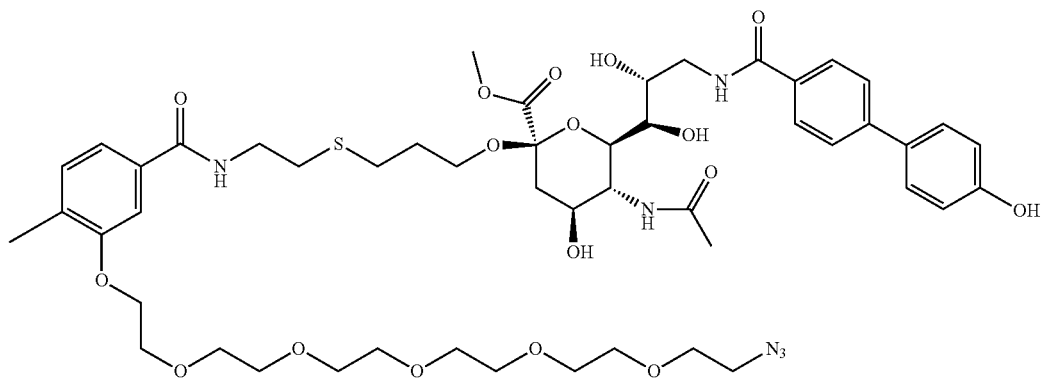

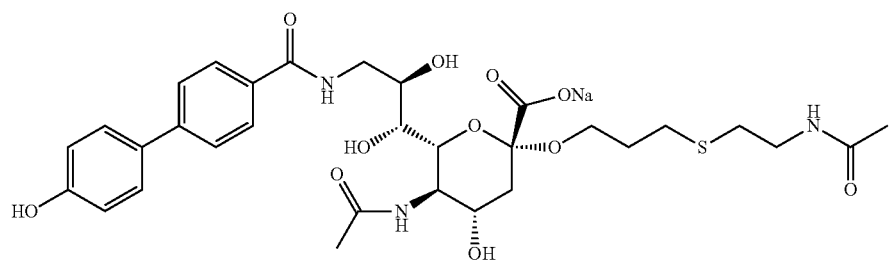
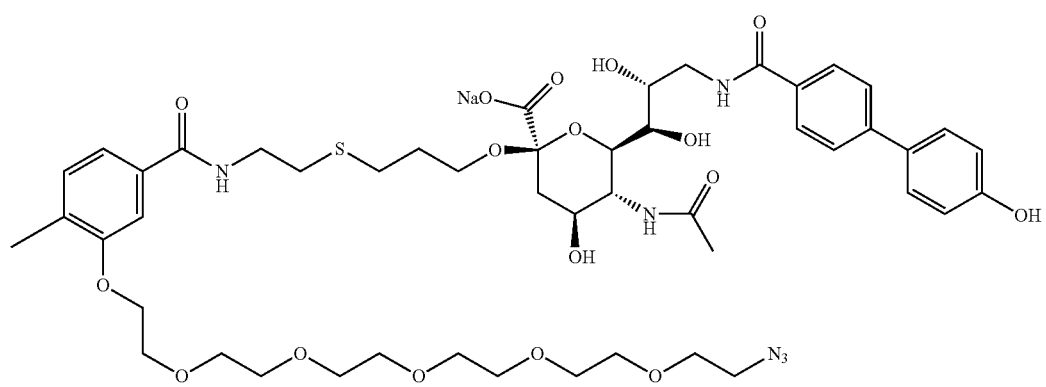
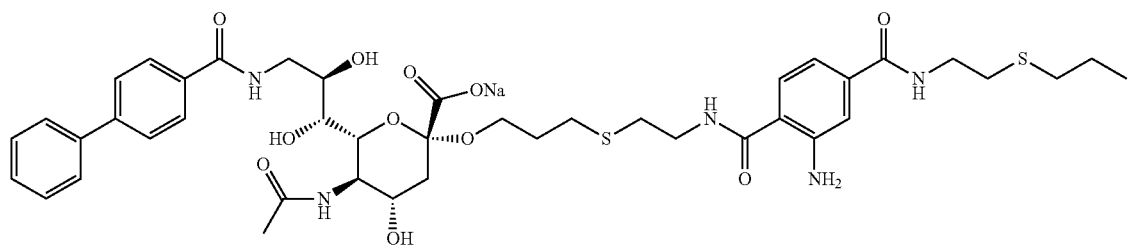
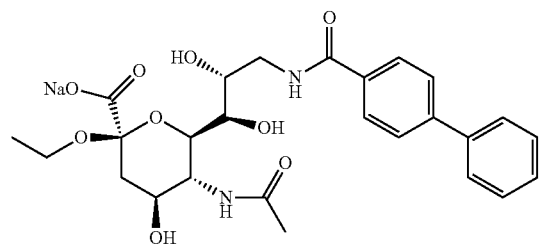
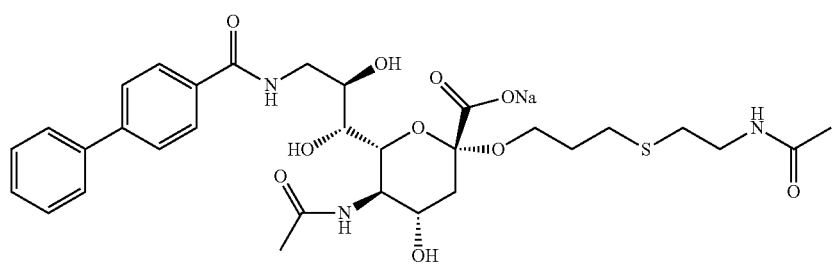

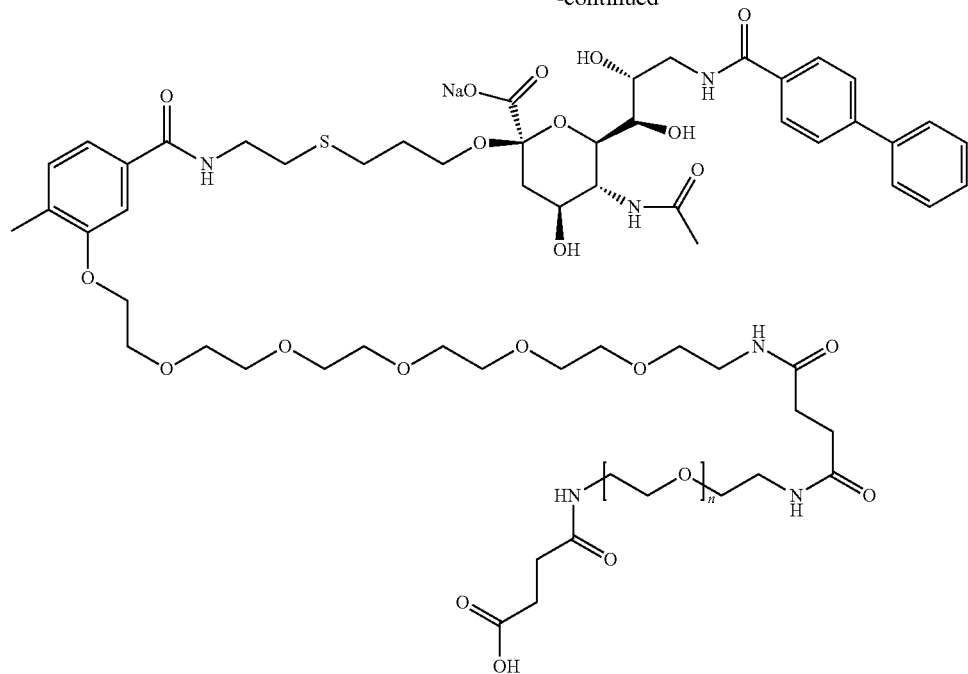
n = 35-51
6. A conjugate of a sialic acid derivative of the formula (I) according to claim 1, selected from the group consisting of:
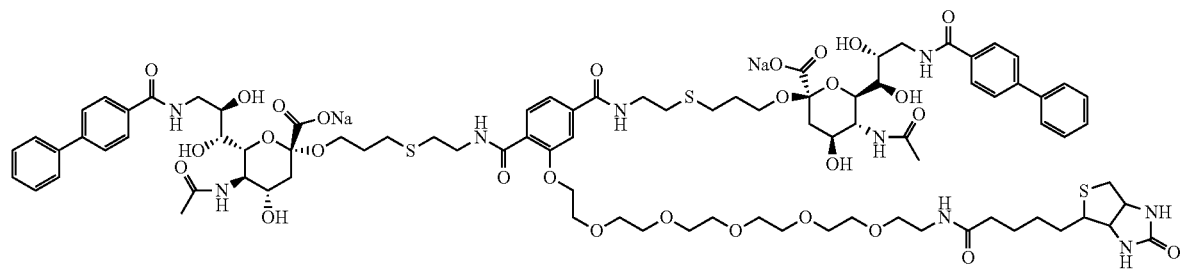
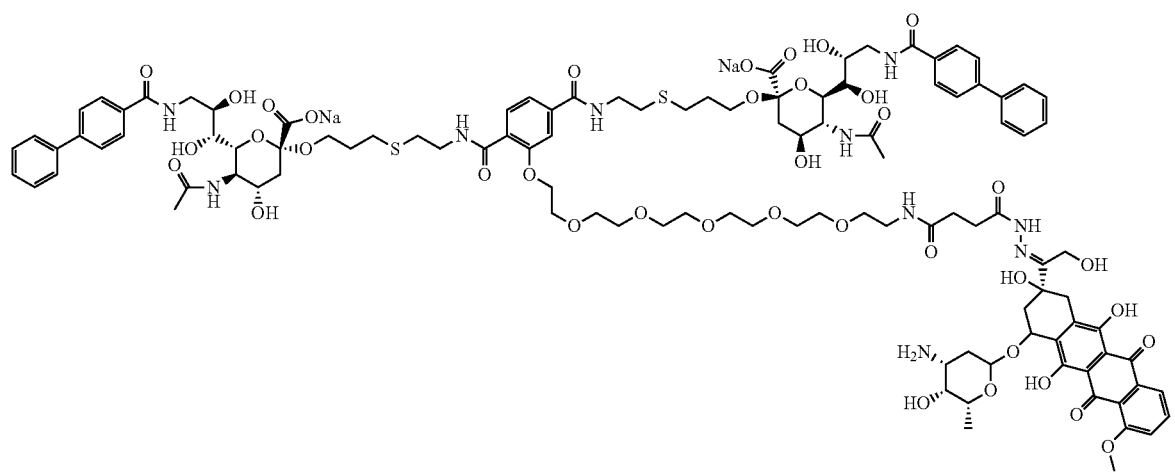

-continued

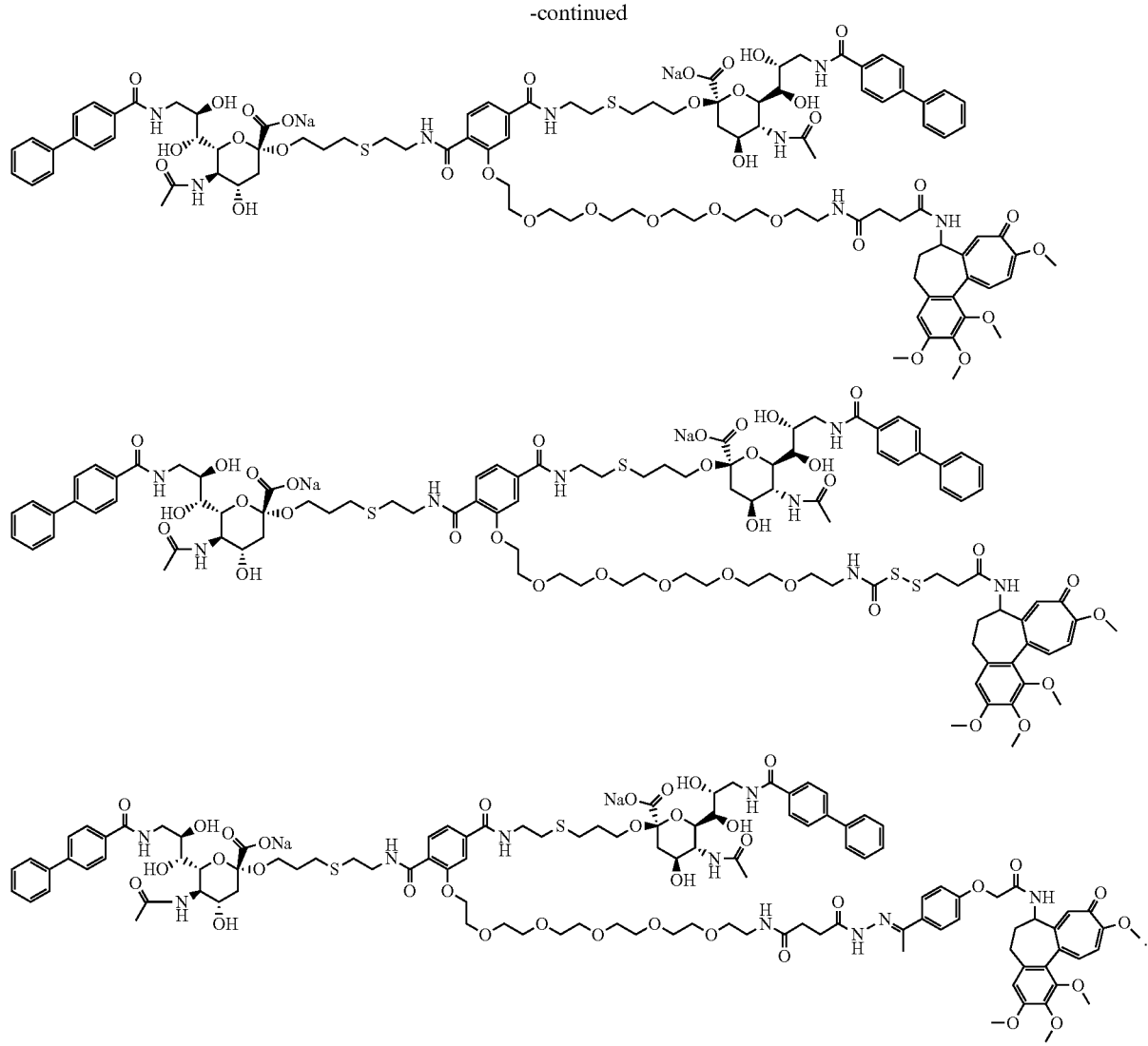

7. Pharmaceutical formulation comprising at least one sialic acid derivative of the formula (I) according to claim 1 or a pharmacologically acceptable salt thereof and a pharmacologically acceptable carrier.

8. Sialic acid derivative of the formula (I) according to claim 1 for use in the preparation of a medicament for the treatment of bacterial, viral, parasitic, tumour autoimmune and immunodeficiency diseases.

9. Sialic acid derivative of the formula (I) according to claim 1 for use in the preparation of a conjugate with a cargo, selected from the group consisting of RNA, DNA, peptides, low molecular weight antigens, antigenic proteins, enzymes and low molecular weight pharmacologically active substances, for regulating metabolic processes, immune reactions, immunizations or desensitizations of the target organism.

10. Pharmacologically active conjugate of a acid derivative of the formula (I) according to claim 1 and a cargo, selected from the group consisting of RNA, DNA, peptides, cytostatics, enzymes, organometallic complexes and low molecular weight pharmacologically active substances, for use in a method for the treatment of infections, tumours or allergies.

11. Sialic acid derivative of the formula (I) according to claim 1 for use in the preparation of a conjugate with liposomes, nanoparticles, organometallic complexes, metal nanoparticles, micromicelles and carbon nanotubules.

12. Sialic acid derivative of the formula (I) according to claim 1 for use in the preparation of liposomes, nanoparticles, micromicelles and carbon nanotubules.

13. Sialic acid derivative of the formula (I) according to claim 1 for use in the preparation of a conjugate with molecules for diagnostic purposes.

14. Sialic acid derivative of the formula (I) according to claim 1 for use in the preparation of polyvalent ligands.

15. Sialic acid derivative of the formula (I) according to claim 1 for use in the preparation of a conjugate with a cargo-bearing polymer, wherein the cargo is selected from the group consisting of RNA, DNA, cytostatics, peptides, low molecular weight antigens, antigenic proteins, enzymes, organometallic complexes and low molecular weight pharmacologically active substances.

* * * * *